United States Patent
Martin

(10) Patent No.: US 10,973,440 B1
(45) Date of Patent: Apr. 13, 2021

(54) MOBILE CONTROL USING GAIT VELOCITY

(71) Applicant: David Martin, San Francisco, CA (US)

(72) Inventor: David Martin, San Francisco, CA (US)

( * ) Notice: Subject to any disclaimer, the term of this patent is extended or adjusted under 35 U.S.C. 154(b) by 0 days.

(21) Appl. No.: 16/275,323

(22) Filed: Feb. 14, 2019

Related U.S. Application Data

(63) Continuation-in-part of application No. 14/922,174, filed on Oct. 25, 2015, now Pat. No. 10,342,462, and a continuation-in-part of application No. 14/932,591, filed on Nov. 4, 2015, now abandoned, and a continuation-in-part of application No. 15/296,868, filed on Oct. 18, 2016, now Pat. No. 10,488,222, and
(Continued)

(51) Int. Cl.
| | |
|---|---|
| *A61B 5/11* | (2006.01) |
| *A61B 5/00* | (2006.01) |
| *G06T 19/20* | (2011.01) |
| *G06K 9/00* | (2006.01) |
| *A63F 13/212* | (2014.01) |
| *G06T 13/40* | (2011.01) |
| *A63F 13/211* | (2014.01) |
| *G01C 22/00* | (2006.01) |
| *G01C 21/14* | (2006.01) |

(52) U.S. Cl.
CPC ............ *A61B 5/112* (2013.01); *A61B 5/6898* (2013.01); *A61B 5/742* (2013.01); *A63F 13/211* (2014.09); *A63F 13/212* (2014.09); *G06K 9/00348* (2013.01); *G06T 13/40* (2013.01); *G06T 19/20* (2013.01); *A61B 5/1112* (2013.01); *G01C 21/14* (2013.01); *G01C 22/006* (2013.01); *G06T 2215/16* (2013.01)

(58) Field of Classification Search
CPC ......... G06T 13/40; G06T 13/80; G06T 19/20; G06T 19/00; G06T 2215/16; G06T 13/20; G06T 7/20; G06F 3/011; G06K 9/00348; A63F 13/21; A63F 13/211; A63F 13/212; A63F 13/213; A61B 5/744
See application file for complete search history.

(56) References Cited

U.S. PATENT DOCUMENTS 5,404,426 A * 4/1995 Usami .................... G06T 13/40
345/420
5,819,206 A * 10/1998 Horton .................... G06F 3/011
702/150
(Continued)

FOREIGN PATENT DOCUMENTS

WO    WO-2010001109 A2 *  1/2010  ............. G06T 13/40

OTHER PUBLICATIONS

"Real-time Computing"; Apr. 2019; Wikipedia article; <https://en.wikipedia.org/wiki/Real-time_computing> (Year: 2019).*
(Continued)

*Primary Examiner* — John Villecco

(57) ABSTRACT

Methods for controlling a mobile or wearable device user's representation in real time are described, where the user is performing a gait activity with a gait velocity, and the gait velocity is used for control. Additional user's mobility characteristics leveraged for control may include cadence and stride length, and the sensors utilized to obtain any contextual information may be accelerometers.

354 Claims, 18 Drawing Sheets

Related U.S. Application Data a continuation-in-part of application No. 16/044,833, filed on Jul. 25, 2018.

(60) Provisional application No. 62/651,409, filed on Apr. 2, 2018, provisional application No. 62/654,536, filed on Apr. 9, 2018, provisional application No. 62/702,998, filed on Jul. 25, 2018, provisional application No. 62/750,292, filed on Oct. 25, 2018, provisional application No. 62/068,685, filed on Oct. 26, 2014, provisional application No. 62/090,698, filed on Dec. 11, 2014, provisional application No. 62/249,371, filed on Nov. 2, 2015, provisional application No. 62/068,685, filed on Oct. 26, 2014.

(56) References Cited

U.S. PATENT DOCUMENTS

| | | | | |
|---|---|---|---|---|
| 6,144,385 | A * | 11/2000 | Girard | G06T 13/40 345/424 |
| 6,356,856 | B1 * | 3/2002 | Damen | A43B 3/00 482/3 |
| 7,647,196 | B2 * | 1/2010 | Kahn | G01C 22/006 702/149 |
| 7,934,983 | B1 * | 5/2011 | Eisner | A63K 1/00 340/7.48 |
| 8,243,078 | B2 * | 8/2012 | Perlin | G06T 13/40 345/473 |
| 8,253,746 | B2 * | 8/2012 | Geisner | G06F 3/011 345/474 |
| 8,475,284 | B1 * | 7/2013 | Rudi | A63F 13/5258 463/42 |
| 8,766,977 | B2 * | 7/2014 | Kim | G06T 7/20 345/420 |
| 8,803,889 | B2 * | 8/2014 | Perez | G06T 7/251 345/474 |
| 8,845,494 | B2 * | 9/2014 | Whitall | A63B 71/0686 482/8 |
| 8,944,928 | B2 * | 2/2015 | Kaps | G06T 13/40 473/199 |
| 8,947,441 | B2 * | 2/2015 | Hodgins | G06T 13/40 345/473 |
| 8,988,437 | B2 * | 3/2015 | Geisner | G06T 13/00 345/474 |
| 9,067,097 | B2 * | 6/2015 | Lane | G06K 9/00342 |
| 9,114,296 | B2 * | 8/2015 | Reynolds, III | A63B 69/0028 |
| 9,142,024 | B2 * | 9/2015 | Sullivan | G06K 9/3216 |
| 9,235,765 | B2 * | 1/2016 | Bentley | G06K 9/00711 |
| 9,411,780 | B1 * | 8/2016 | Awad | G06Q 50/01 |
| 9,533,228 | B2 * | 1/2017 | Dugan | A63F 13/211 |
| 9,610,506 | B2 * | 4/2017 | Dugan | A63F 13/31 |
| 9,652,992 | B2 * | 5/2017 | Kaleal, III | G06T 19/00 |
| 9,700,802 | B2 * | 7/2017 | Dugan | A63B 71/0622 |
| 9,799,136 | B2 * | 10/2017 | Griffith | G06T 15/20 |
| 9,873,054 | B2 * | 1/2018 | Dugan | A63F 13/816 |
| 9,914,053 | B2 * | 3/2018 | Dugan | A63F 13/816 |
| 9,993,182 | B2 * | 6/2018 | Xu | G06K 9/00362 |
| 9,996,739 | B2 * | 6/2018 | Wu | A61B 5/117 |
| 10,065,074 | B1 * | 9/2018 | Hoang | A63B 24/0003 |
| 10,108,855 | B2 * | 10/2018 | Lim | G06K 9/00342 |
| 10,118,100 | B2 * | 11/2018 | Dugan | A63B 71/0622 |
| 10,132,645 | B1 * | 11/2018 | Yuen | A61B 5/1118 |
| 10,157,488 | B2 * | 12/2018 | Chamdani | G06T 13/40 |
| 10,219,726 | B2 * | 3/2019 | Wei | A61B 5/1071 |
| 10,271,790 | B2 * | 4/2019 | Lee | A61B 5/6802 |
| 10,359,839 | B2 * | 7/2019 | Kato | G02B 27/017 |
| 10,376,739 | B2 * | 8/2019 | Cook | A63B 24/0075 |
| 10,709,382 | B2 * | 7/2020 | Karavirta | G16H 40/67 |
| 2002/0057278 | A1 * | 5/2002 | Bruderlin | G06T 13/40 345/582 |
| 2004/0012594 | A1 * | 1/2004 | Gauthier | G06T 13/40 345/473 |
| 2004/0167420 | A1 * | 8/2004 | Song | A61B 5/053 600/547 |
| 2006/0262120 | A1 * | 11/2006 | Rosenberg | G06F 3/011 345/473 |
| 2007/0273705 | A1 * | 11/2007 | Bruderlin | G06T 13/40 345/581 |
| 2008/0278497 | A1 * | 11/2008 | Jammes | B25J 9/1664 345/474 |
| 2009/0043531 | A1 * | 2/2009 | Kahn | A61B 5/1112 702/149 |
| 2009/0135187 | A1 * | 5/2009 | Lee | G06T 13/40 345/473 |
| 2010/0156912 | A1 * | 6/2010 | Sung | G06T 13/40 345/474 |
| 2010/0295771 | A1 * | 11/2010 | Burton | G06F 3/011 345/156 |
| 2010/0302253 | A1 * | 12/2010 | Kipman | G06T 13/40 345/473 |
| 2011/0009241 | A1 * | 1/2011 | Lane | A63B 24/0087 482/8 |
| 2011/0119332 | A1 * | 5/2011 | Marshall | A63F 13/10 709/203 |
| 2011/0184225 | A1 * | 7/2011 | Whitall | A63B 24/0003 600/28 |
| 2012/0083705 | A1 * | 4/2012 | Yuen | A61B 5/0002 600/508 |
| 2012/0252580 | A1 * | 10/2012 | Dugan | A63F 13/31 463/42 |
| 2012/0253487 | A1 * | 10/2012 | Dugan | A63B 71/0622 700/91 |
| 2012/0253489 | A1 * | 10/2012 | Dugan | A63B 71/0622 700/91 |
| 2012/0254934 | A1 * | 10/2012 | McBrearty | G06F 19/3481 725/118 |
| 2012/0315986 | A1 * | 12/2012 | Walling | A63F 13/332 463/31 |
| 2013/0038601 | A1 * | 2/2013 | Han | G06T 13/40 345/419 |
| 2013/0041590 | A1 * | 2/2013 | Burich | G06F 19/3418 702/19 |
| 2013/0063418 | A1 * | 3/2013 | Kaschalk | G06T 13/20 345/419 |
| 2013/0127873 | A1 * | 5/2013 | Popovic | G06T 13/40 345/473 |
| 2014/0031703 | A1 * | 1/2014 | Rayner | A61B 5/02055 600/484 |
| 2014/0078144 | A1 * | 3/2014 | Berriman | A63F 13/10 345/426 |
| 2014/0093249 | A1 * | 4/2014 | Roberts | G01C 21/165 398/127 |
| 2014/0160122 | A1 * | 6/2014 | Chou | G06T 13/40 345/420 |
| 2014/0276130 | A1 * | 9/2014 | Mirelman | A61B 5/744 600/483 |
| 2014/0303758 | A1 * | 10/2014 | Reynolds, III | A63B 69/0028 700/91 |
| 2015/0002518 | A1 * | 1/2015 | Nakajima | G06T 13/40 345/474 |
| 2015/0032033 | A1 * | 1/2015 | Kaufman | A61B 5/726 600/595 |
| 2015/0066174 | A1 * | 3/2015 | Dugan | A63B 71/0622 700/91 |
| 2015/0112603 | A1 * | 4/2015 | Zhong | G06K 9/46 702/19 |
| 2015/0127298 | A1 * | 5/2015 | Gangumalla | G01C 22/006 702/160 |
| 2015/0154452 | A1 * | 6/2015 | Bentley | G06K 9/00711 386/201 |
| 2015/0285659 | A1 * | 10/2015 | Curtis | G01C 22/006 702/97 |
| 2015/0352441 | A1 * | 12/2015 | Lin | A63F 13/428 463/36 |
| 2015/0362330 | A1 * | 12/2015 | Omr | G01C 21/14 702/160 |
| 2015/0362520 | A1 * | 12/2015 | Wells | G01C 19/00 702/141 |
| 2015/0375108 | A1 * | 12/2015 | Pathirana | G01S 5/0221 463/39 |

(56) References Cited

U.S. PATENT DOCUMENTS

| | | | | |
|---|---|---|---|---|
| 2016/0000373 A1* | 1/2016 | Karavirta | ............. | A61B 5/6801 702/19 |
| 2016/0007158 A1* | 1/2016 | Venkatraman | ........ | H04W 4/023 455/456.2 |
| 2016/0078635 A1* | 3/2016 | Kanevsky | ............... | G06F 16/51 345/474 |
| 2016/0086500 A1* | 3/2016 | Kaleal, III | ............. | G06T 19/00 434/257 |
| 2016/0114213 A1* | 4/2016 | Lee | ...................... | A61B 5/6802 434/255 |
| 2016/0171377 A1* | 6/2016 | Caritu | ................ | G06K 9/00536 706/14 |
| 2016/0235363 A9* | 8/2016 | Karavirta | ............. | G01P 15/00 |
| 2016/0262685 A1* | 9/2016 | Wagner | ................ | A61B 5/1101 |
| 2016/0263482 A1* | 9/2016 | Dugan | .................... | A63F 13/31 |
| 2016/0267699 A1* | 9/2016 | Borke | .................... | G02B 27/2292 |
| 2016/0367879 A1* | 12/2016 | Reynolds, III | ......... | G16H 20/30 |
| 2017/0018110 A1* | 1/2017 | Raschke | ............ | G06K 9/00348 |
| 2017/0080340 A1* | 3/2017 | Dugan | .................. | A63F 13/816 |
| 2017/0095181 A1* | 4/2017 | Hauenstein | ........... | A61B 5/1118 |
| 2017/0095732 A1* | 4/2017 | Ghaffari | ................ | A63F 13/211 |
| 2017/0192496 A1* | 7/2017 | Balslev | ..................... | G06F 3/011 |
| 2017/0231532 A1* | 8/2017 | Chakravarty | .......... | A61B 5/112 600/595 |
| 2017/0238845 A1* | 8/2017 | Wei | ...................... | A61B 5/6829 |
| 2017/0238846 A1* | 8/2017 | Xu | ........................ | G06K 9/6202 |
| 2017/0243057 A1* | 8/2017 | Wu | ..................... | A61B 5/7275 |
| 2017/0281085 A1* | 10/2017 | Lee | ...................... | A61B 5/6802 |
| 2017/0286641 A1* | 10/2017 | Dugan | ............... | A63B 71/0622 |
| 2017/0322031 A1* | 11/2017 | Eastman | ............... | G01C 21/165 |
| 2018/0117475 A1* | 5/2018 | Dugan | .................. | A63F 13/816 |
| 2018/0156920 A1* | 6/2018 | Diggelen | ................ | G01S 19/19 |
| 2018/0185754 A1* | 7/2018 | Dugan | .................. | A63F 13/816 |
| 2018/0224930 A1* | 8/2018 | Folmer | ................. | A63F 13/211 |
| 2018/0236352 A1* | 8/2018 | El-Sheimy | ................ | B81B 7/02 |
| 2018/0268589 A1* | 9/2018 | Grant | ..................... | G06T 13/40 |
| 2018/0315133 A1* | 11/2018 | Brody | ..................... | H04L 51/20 |
| 2018/0341982 A1* | 11/2018 | Gotoh | ..................... | H04S 3/008 |
| 2018/0342106 A1* | 11/2018 | Rosado | .................. | A63F 13/86 |
| 2019/0070511 A1* | 3/2019 | Dugan | ............... | A63B 71/0622 |
| 2019/0150796 A1* | 5/2019 | Fukushi | ................... | A61B 5/11 |
| 2020/0053501 A1* | 2/2020 | Mochizuki | ............. | H04S 7/303 |
| 2020/0221245 A1* | 7/2020 | Mochizuki | ............. | H04S 7/303 |
| 2020/0230494 A1* | 7/2020 | Gotoh | .................... | G01C 21/26 |
| 2020/0289027 A1* | 9/2020 | Naveh | .................. | A61B 5/7264 |

OTHER PUBLICATIONS

Kider et al. "A data-driven appearance model for human fatigue", SCA '11: Proceedings of the 2011 ACM SIGGRAPH/Eurographics Symposium on Computer Animation; Aug. 2011; pp. 119-128 <https://doi.org/10.1145/2019406.2019423> (Year: 2011).*

* cited by examiner

```
class AnimationView extends SurfaceView implements SurfaceHolder.Callback {
    class AnimationThread extends Thread implements SensorEventListener, OnTouchListener {
        Bitmap imagesStrip;
        long frame_0_StartTime;
        boolean beginning_manageCurrentFrame=true;
        long timeIntoCompleteAnimation;
        int frameCount=26;
        int completeAnimationPeriod=1000;// To be programmatically changed.
        int currentFrame=0;
        int frameWidth=300, frameHeight=360;
        Rect frameToDraw=new Rect(0,0,frameWidth,frameHeight);
        float personXPos=0, personYPos=0;
        RectF whereToDraw=new
            RectF(personXPos,personYPos,personXPos+frameWidth,personYPos+frameHeight);

//Additional code not included for clarity purposes.

public void manageCurrentFrame() {
            long time=System.currentTimeMillis();
            if (beginning_manageCurrentFrame && currentFrame==0) {
                frame_0_StartTime=time;
                beginning_manageCurrentFrame=false;
            }
            timeIntoCompleteAnimation=time-frame_0_StartTime;
            currentFrame=
   (int)(timeIntoCompleteAnimation*frameCount/completeAnimationPeriod)%frameCount;
            frameToDraw.left=currentFrame*frameWidth;
            frameToDraw.right=frameToDraw.left+frameWidth;
        }
```

FIG. 11A

```
private void doDraw(Canvas canvas) {
    manageCurrentFrame();
    canvas.drawBitmap(imagesStrip,frameToDraw,whereToDraw,null);
} public void setAnimationImagesStrip(int stripResource) {
    imagesStrip.recycle();
    imagesStrip=null;
    AssetManager assets=getResources().getAssets();
    InputStream buffer;
    String myFilename="";
    if (stripResource==0) {
        myFilename="firstImagesStripFile.png";
    } else if (stripResource==1) {
        myFilename="secondImagesStripFile.png";
    } else if (stripResource==2) {
        myFilename="thirdImagesStripFile.png";
    }
    try {
        buffer=new BufferedInputStream(assets.open(myFilename));
        imagesStrip=BitmapFactory.decodeStream(buffer);
    } catch (IOException e) {e.printStackTrace();}
    imagesStrip=
    Bitmap.createScaledBitmap(imagesStrip,frameWidth*frameCount,frameHeight,true);
    }
  }
}
```

FIG. 11B

```
public void onSensorChanged(SensorEvent event) {
    if(event.sensor.getType() == Sensor.TYPE_ACCELEROMETER) {
        double x_acceleration=(double)event.values[0];
        double y_acceleration=(double)event.values[1];
        double z_acceleration=(double)event.values[2];
        double signal_vector_module_acceleration=
            Math.sqrt((x_acceleration*x_acceleration)+
            (y_acceleration*y_acceleration)+(z_acceleration*z_acceleration));

double[] array_returned_from_determine_gait_parameters=
            determine_gait_parameters(x_acceleration,y_acceleration,
            z_acceleration,signal_vector_module_acceleration);
        double velocity=array_returned_from_determine_gait_parameters[0];
        double calories=array_returned_from_determine_gait_parameters[1];
        double cadence=array_returned_from_determine_gait_parameters[2];
        double activity= array_returned_from_determine_gait_parameters[3];

int previous_completeAnimationPeriodInMsec=completeAnimationPeriod;
        int new_completeAnimationPeriodInMsec=(int) (1000*2/cadence);
        if (new_completeAnimationPeriodInMsec!=previous_completeAnimationPeriodInMsec){
            long time_now = System.currentTimeMillis();
            frame_0_StartTime=time_now-(int)( new_completeAnimationPeriodInMsec *
            (timeIntoCompleteAnimation%previous_completeAnimationPeriodInMsec) /
            (double)previous_completeAnimationPeriodInMsec );
            completeAnimationPeriod=new_completeAnimationPeriodInMsec;
        }
    }
}
```

FIG. 13

MOBILE CONTROL USING GAIT VELOCITY

CROSS REFERENCE TO RELATED APPLICATIONS

This application claims the benefits of U.S. provisional patent application No. 62/651,409, by David Martin, entitled "Control Strategies For Mobile Using Gait Analysis", filed Apr. 2, 2018, and U.S. provisional patent application No. 62/654,536, by David Martin, entitled "Control For Health Care In Mobile Leveraging Gait Analysis", filed Apr. 9, 2018, and U.S. provisional patent application No. 62/702,998, by David Martin, entitled "Leveraging mobility features for precise control", filed Jul. 25, 2018, and U.S. provisional patent application No. 62/750,292, by David Martin, entitled "Gait analysis applied for control", filed Oct. 25, 2018.

This application is a continuation-in-part of co-pending U.S. application Ser. No. 14/922,174, by David Martin, entitled "Application of Gait Characteristics for Mobile", filed Oct. 25, 2015, which claims the benefits of U.S. provisional patent application No. 62/068,685, by David Martin, entitled "Application of Gait Characteristics for Mobile", filed Oct. 26, 2014.

This application is also a continuation-in-part of co-pending U.S. application Ser. No. 14/932,591, by David Martin, entitled "Enhanced Real Time Frailty Assessment for Mobile", filed Nov. 4, 2015, which claims the benefits of U.S. provisional patent application No. 62/090,698, by David Martin, entitled "Enhanced Real Time Frailty Assessment for Mobile", filed Dec. 11, 2014.

This application is also a continuation-in-part of co-pending U.S. application Ser. No. 15/296,868, by David Martin, entitled "Mobile device control leveraging user kinematics", filed Oct. 18, 2016, which claims the benefits of U.S. provisional patent application No. 62/249,371, by David Martin, entitled "Mobile device control leveraging user kinematics", filed Nov. 2, 2015.

This application is also a continuation-in-part of co-pending U.S. application Ser. No. 16/044,833, by David Martin, entitled "Refined Control Leveraging Mobile Characteristics for health care", filed Jul. 25, 2018, which claims the benefits of at least U.S. provisional patent application No. 62/068,685, by David Martin, entitled "Application of Gait Characteristics for Mobile", filed Oct. 26, 2014.

All of these applications are hereby incorporated by reference in their entireties for all purposes.

BACKGROUND

Field

This application relates to mobile and wearable devices, specifically to methodologies to leverage user's gait characteristics for control, focusing on velocity.

Discussion of Related Art

Common methods to obtain cadence by means of sensors embedded within mobile or wearable devices make use of thresholds, and detect steps when the value of a sensor signal reaches said thresholds. In order to achieve an accuracy improvement, the use of adaptable thresholds has also been proposed. Nevertheless, most of those approaches focus their analysis on the time domain, and although some methods make use of frequency analysis (e.g. using FFT to obtain the fundamental frequency of the signal), their algorithms still rely on thresholding in the time domain, making them prone to errors, especially with weak or noisy motion signals typical of walking. Recent studies with commercially available devices show large errors in the determination of the user's cadence, and those errors increase as the walking velocity decreases. In fact, considerable inaccuracies at low speeds may have important implications in health care applications. Consequently, there is a need for an enhanced methodology to accurately determine the cadence and other gait attributes (e.g. velocity, stride length, calories burned per time unit, activity) of mobile or wearable device users, and enable a new field of applications not possible with existing methodology. Among those applications, the control of a representation of the device user on the device screen, leveraging gait attributes such as velocity.

BRIEF DESCRIPTION OF THE DRAWINGS

FIG. 11A, 11B present schematic code to describe the control of elements displayed on the device screen to control the user's representation, according to one embodiment.

FIG. 13 presents schematic code to describe the implementation of the onSensorChanged method in a mobile application, according to one embodiment.

DETAILED DESCRIPTION OF EMBODIMENTS OF THE INVENTION

Although the following text sets forth a detailed description of numerous different embodiments, it should be understood that the legal scope of the description is defined by the words of the claims set forth at the end of this disclosure. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent using the sentence "As used herein, the term ' ' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning.

Some inventive functionality and inventive principles may be implemented with or in software programs or instructions and integrated circuits (ICs) such as application specific ICs. In the interest of brevity and minimization of any risk of obscuring the principles and concepts according to the present invention, discussion of such software and ICs, if any, is limited to the essentials with respect to the principles and concepts within some of the embodiments.

Figure 1A:
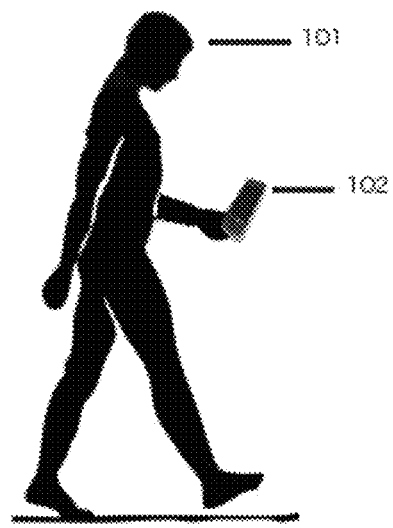
FIG. 1A represents an example of mobile device user walking with the device.
Figure 1B:
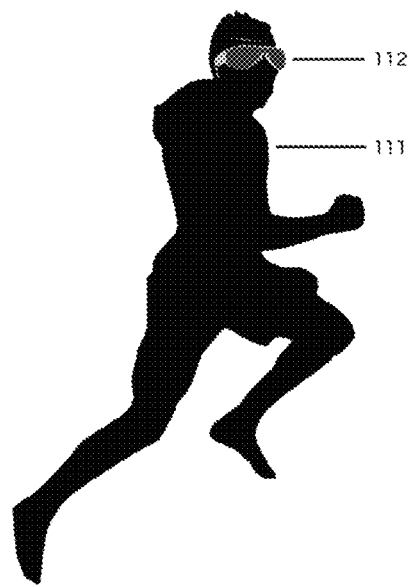
FIG. 1B represents an example of wearable device user running with the device.

FIG. 1A represents an individual, (101), walking with a mobile device, (102). In some embodiments, individual (101) may be performing any kind of walking, jogging, running, sprinting, or any other type of gait activity (including household activities. This Figure and its elements (510), (520), (530), (540), (550), (560), (570), and (580) are further described in U.S. application Ser. No. 14/922,174, by David Martin, entitled "Application of Gait Characteristics for Mobile", filed Oct. 25, 2015, and U.S. application Ser. No. 16/044,833, by David Martin, entitled "Refined Control Leveraging Mobile Characteristics for Health Care", filed Jul. 25, 2018, which are hereby incorporated by reference for all purposes. FIG. 1B represents an example of one embodiment in which individual (111) is running while wearing a device in the form of glasses (112). In some embodiments (112) may represent any type of virtual reality device, eyewear, glasses or any other type of wearable or mobile device that individual (111) is wearing in any way attached or positioned on his/her face, head, or any other place of his/her body. This Figure and its elements are further described in application Ser. No. 14/922,174 and application Ser. No. 16/044,833.

Figure 1C:
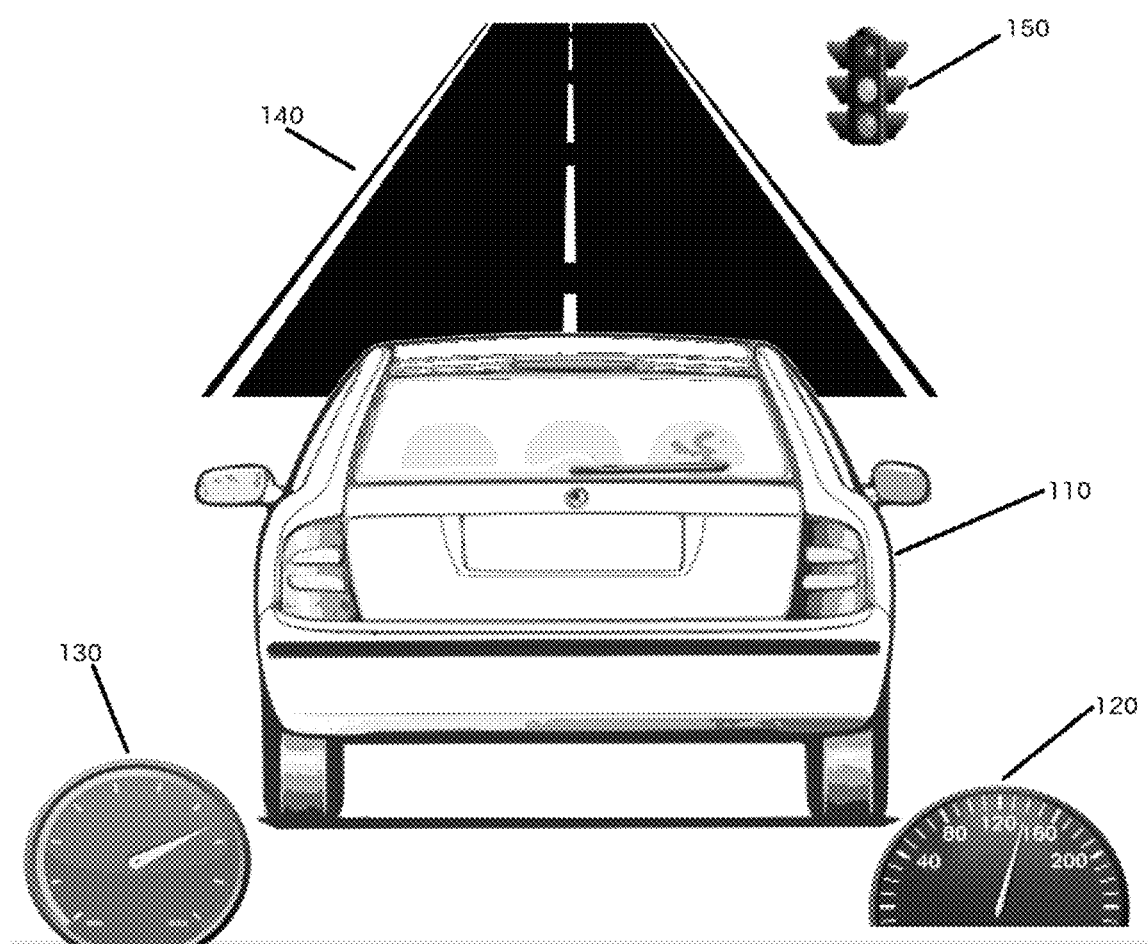
FIG. 1C illustrates an example of virtual environment displayed on the mobile or wearable device according to one embodiment.

In some embodiments, FIG. 1C may illustrate an example of screenshot of the display of devices (102) or (112), representing a virtual environment with which the individual (101) or (111) may interact. By way of example, and not limitation, the display may show a car (110) moving along a road (140) with some elements such as traffic lights (150). Moreover, the display may also show some dashboarb elements such as (120) or (130) to indicate certain magnitudes, variables or metrics of any kind. This Figure and its elements are further described in application Ser. No. 14/922,174 and application Ser. No. 16/044,833.

Figure 2A:
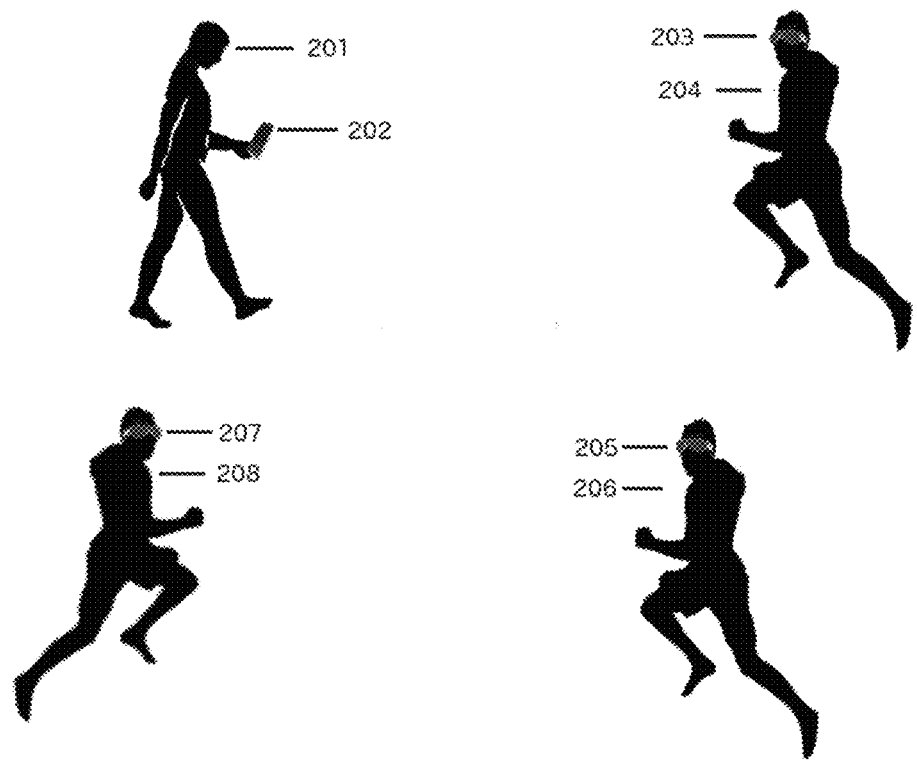
FIG. 2A represents an example of mobile and/or wearable device users performing some gait activity with their devices in a networking environment.

FIG. 2A represents an example of an embodiment in which four individuals (201), (204), (206), (208) participate in a networking environment; in this particular embodiment, each individual has one device: individual (201) is walking and has device (202), which may represent a smartphone, phablet, tablet, or any other type of device. Individual (204) is running and has device (203). In a similar way, individuals (206) and (208) are running and wearing their own devices (205) and (207) respectively. This Figure and its elements are further described in application Ser. No. 14/922,174 and application Ser. No. 16/044,833.

Figure 2B:
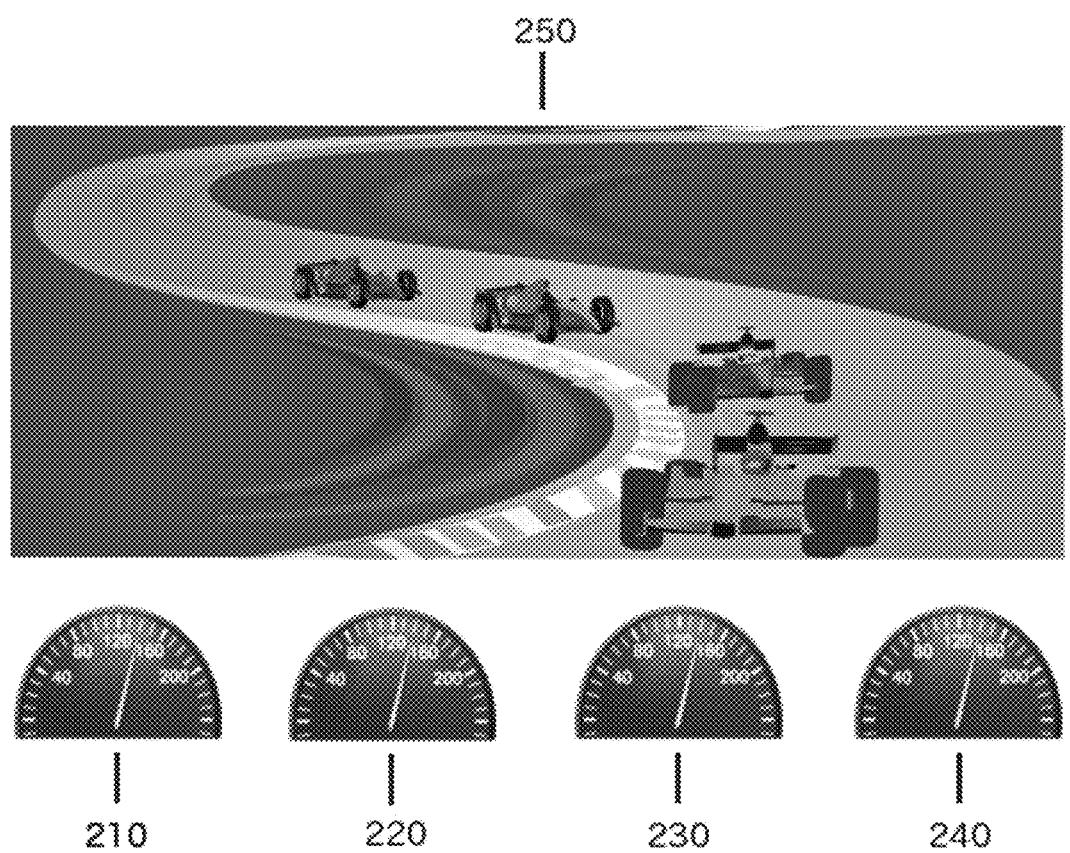
FIG. 2B illustrates an example of virtual environment displayed on the mobile and/or wearable devices in a networking environment according to one embodiment.

FIG. 2B represents an example of an embodiment illustrating an example of screenshot of the display of any or all of the devices (202), (203), (207) or (205). In a particular embodiment corresponding to a networking environment such as the one represented in FIG. 2A, FIG. 2B may represent an example of screenshot seen by individuals (201), (204), (206) and (208) in the display of any or all of their devices. This Figure and its elements (210), (220), (230), (240), and (250) are further described in application Ser. No. 14/922,174 and application Ser. No. 16/044,833.

Figure 3:
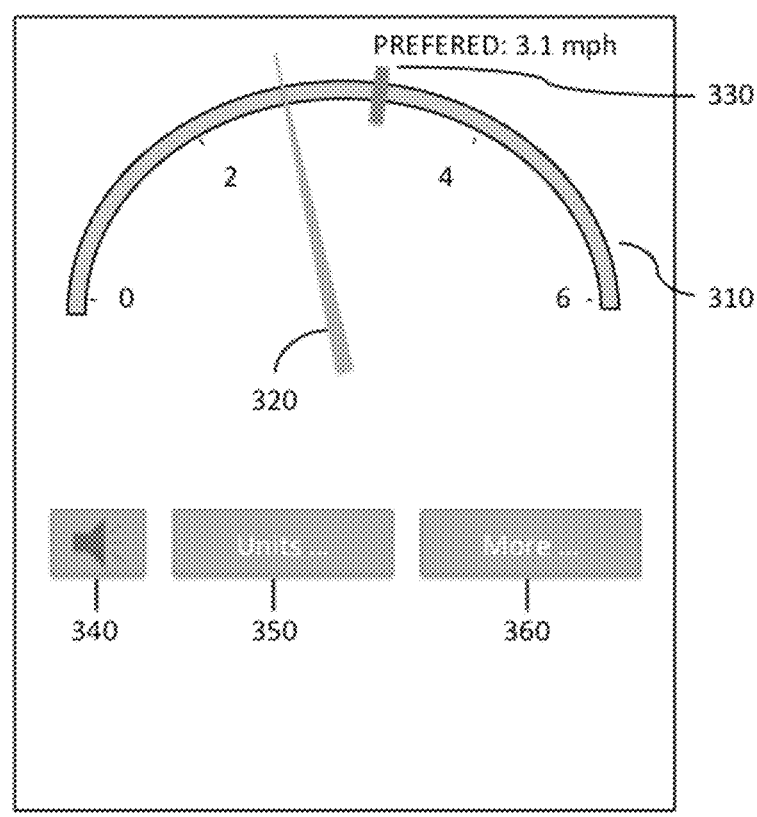
FIG. 3 shows an example of an embodiment of the presentation of contextual information on a mobile and/or wearable device.

In some embodiments, any contextual information may be displayed directly on the user's device display. By way of example and not limitation, the velocity of the user may be displayed in real time (typically, fractions of a second) on the mobile device display as shown in FIG. 3, which illustrates an example of the many possibilities. This Figure and its elements (310), (320), (330), (340), (350), and (360) are further described in application Ser. No. 14/922,174.

Figure 4:
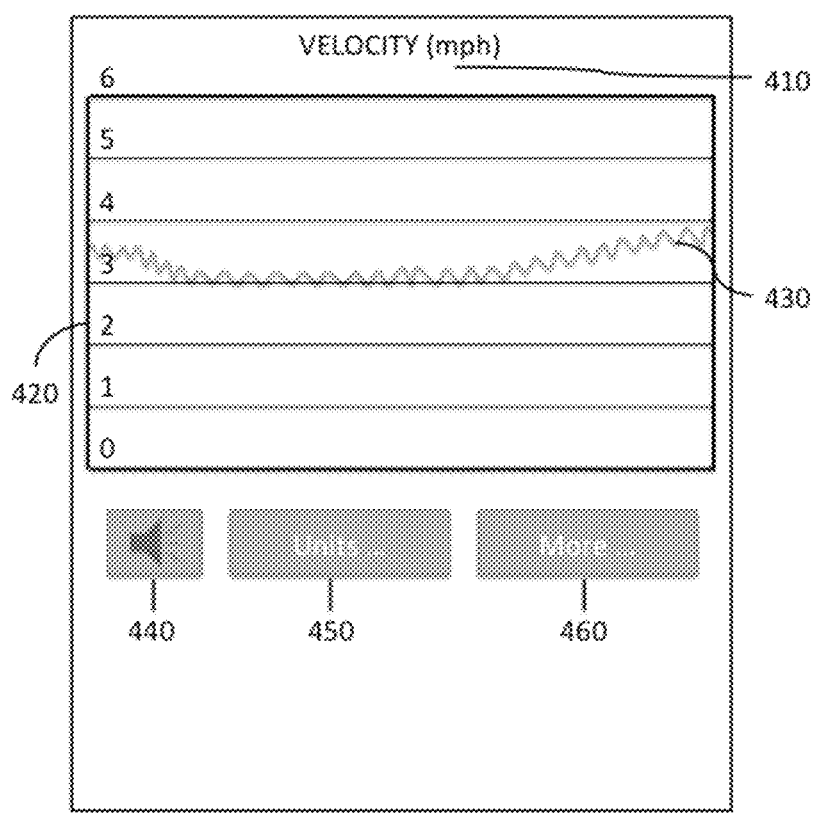
FIG. 4 shows an example of another embodiment of the presentation of contextual information on a mobile and/or wearable device.

FIG. 4 represents an embodiment of a representation of the user's velocity; in other embodiments, any other contextual information and/or gait characteristic or attribute (e.g. stride length, cadence, calories burned, etc. and combinations thereof) or related information may be represented. This Figure and its elements (410), (420), (430), (440), (450), and (460) are further described in application Ser. No. 14/922,174 and application Ser. No. 16/044,833.

Figure 5A:
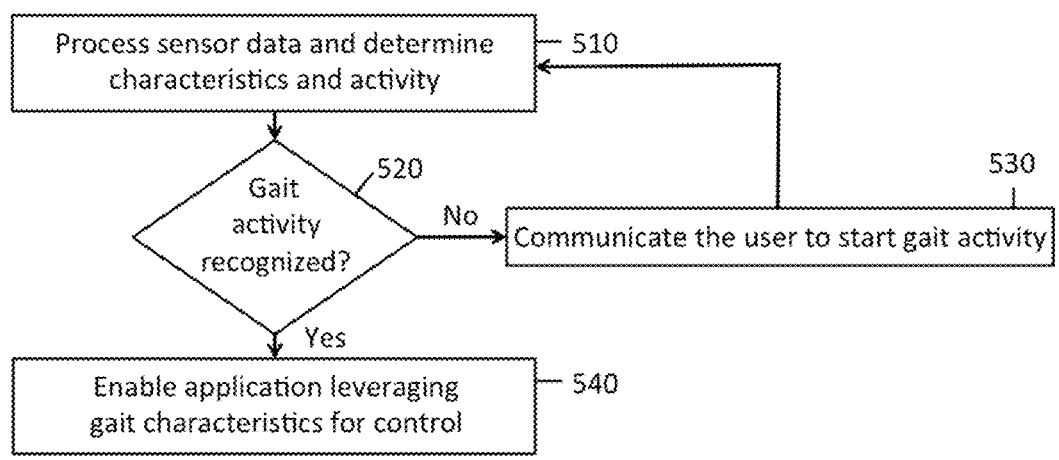
FIG. 5A presents a process flow diagram of an embodiment enabling and controlling an application with the user's gait characteristics.

FIG. 5A represents a flow diagram of possible basic steps of some embodiments enabling and controlling an application with the user's gait characteristics (including cadence, stride length, velocity, calories burned per time unit, activity, device position and/or any other and/or any variations and/or combinations thereof). This Figure and its elements (510), (520), (530), and (540) are further described in application Ser. No. 14/922,174 and application Ser. No. 16/044,833.

Figure 5B:
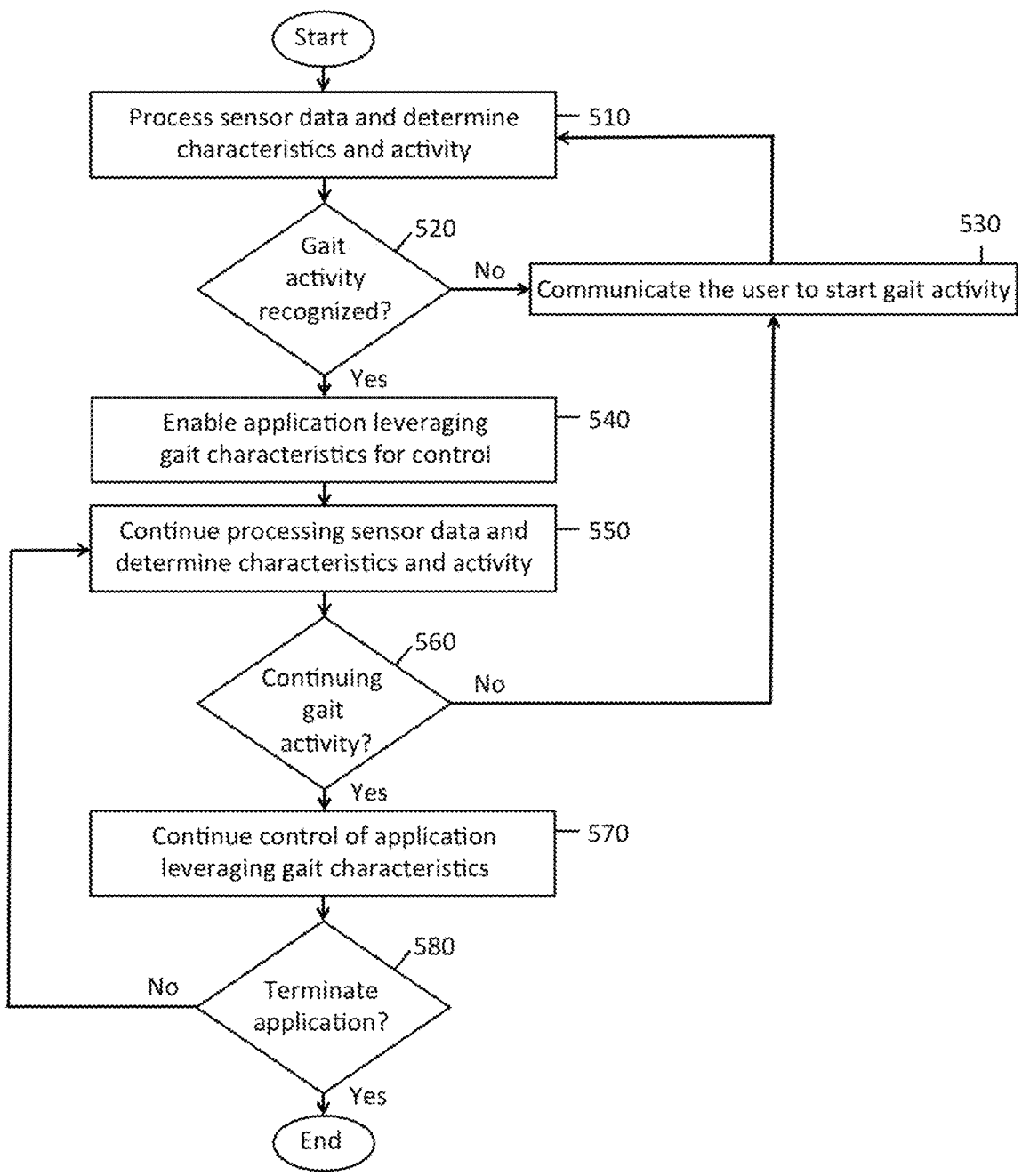
FIG. 5B presents a process flow diagram of another embodiment enabling and controlling an application with the user's gait characteristics.

FIG. 5B represents an extension of the flow diagram of possible basic steps from FIG. 5A that may be applicable to other embodiments. This Figure and its elements (510), (520), (530), (540), (550), (560), (570), and (580) are further described in application Ser. No. 14/922,174 and application Ser. No. 16/044,833.

Figure 6:
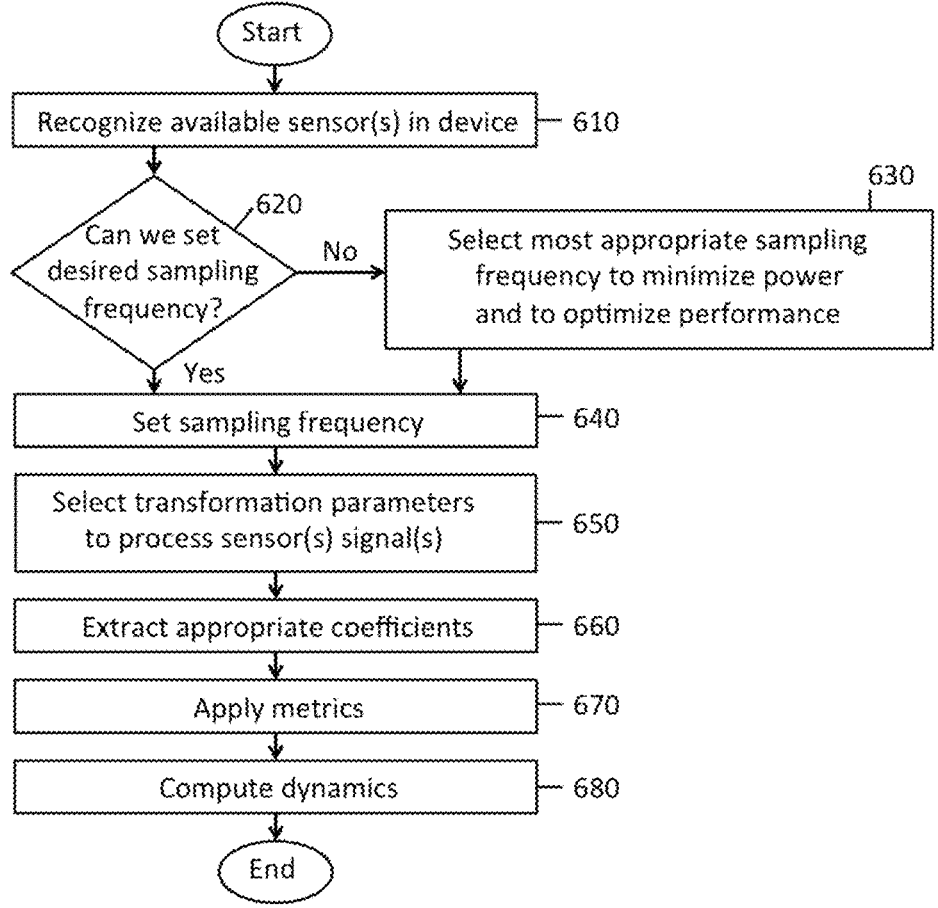
FIG. 6 illustrates a process flow diagram for the user's dynamics information determination according to one embodiment.

FIG. 6 illustrates a flow diagram of one embodiment with possible basic steps of a method for providing a user's dynamics information. In some embodiments, dynamics information may include, by way of example without limitation, velocity, activity, cadence, stride time, stride length, caloric consumption, calories burned per time unit, device position, kinetic energy, etc. and/or any combinations and/or variations thereof. This Figure and its elements (610), (620), (630), (640), (650), (660), (670), and (680) are further described in application Ser. No. 14/922,174 and application Ser. No. 16/044,833.

In some embodiments, an indication of the fundamental frequency or cadence of the gait of a mobile or wearable device user, may be determined through the analysis of a motion sensor signal (e.g. the motion sensor can be a tri-axial accelerometer embedded within the device, and the signal vector module may be analyzed), by means of a Fourier transformation of said signal over a time window. By way of example without limitation, choosing a time window of four seconds (some embodiments may use windows with different time lengths, including by way of example without limitation, 2, 4, 6, 8, 20, 40 seconds or any other amount of seconds) for the motion sensor signal, the Fourier transformation of said signal may provide a representation of its frequency components; in some cases, the strongest frequency component in said representation may coincide with the fundamental frequency of the user's gait or cadence; however, it must be noted that in some conditions, the analysis through the Fourier transformation may deliver misleading results, and special considerations may need to be taken into account to correct those results; by way of example without limitation, the combination of Fourier transformation with other techniques (e.g. wavelet transformation, Hilbert transformation, peak counting, correlation, autocorrelation, thresholding in time domain, and/or any other and/or combinations thereof) may help increase the accuracy in the determination of the user's cadence. By way of example without limitation, a cadence solution obtained through Fourier transformation analysis can be confirmed or rejected by a cadence solution obtained independently by any other technique (in case of rejection, priority can be given, for example, to the solution closest to the past (previous processing) cadence value); and in case of several techniques being used, a majority vote could be employed to decide on the final solution in case of discrepancies. Additional examples of combinations of techniques to obtain cadence are included in the rest of this specification. Any variations of any said elements and/or parameters and/or techniques and/or procedures and/or any combinations thereof may also be possible.

In some embodiments, an indication of the fundamental frequency of a motion sensor signal (or an indication of the cadence of a mobile or wearable device user's gait) can be determined by means of an autocorrelation of the motion sensor signal over a time window. By way of example without limitation, selecting the motion sensor signal over a four seconds time window and performing an autocorrelation of said signal, delivers another signal (for clarity purposes, called second signal, which typically consists of a central maximum surrounded by secondary minima and maxima), from which the inverse of the time distance between the central maximum of said second signal and the largest secondary maximum of said second signal, represents an indication of the fundamental frequency of the original motion sensor signal over said four seconds time window. Some embodiments may use a different length of the time window (e.g. two seconds, six seconds, eight seconds, twenty seconds, sixty seconds, or any other length based on criteria comprising computational costs, dynamism of the solution, accuracy of the solution, frequency content, update frequency, and/or any others). Some embodiments may use different approaches to obtain the previously called second signal, comprising by way of example without limitation, a further division of the signal by its variance, and/or using a pre-processing phase to filter the original motion sensor signal at a particular frequency band (e.g. using a dynamic filter whose central frequency is updated over time based on a previously determined fundamental frequency of the motion signal obtained by means of a frequency transformation; or using the wavelet transformation to filter the motion signal over a range of frequency bands, in response to an indication that the mobile device has experienced a substantial orientation change, wherein said indication is obtained through the analysis of the motion signal with the Fourier transformation), and/or pre-conditioning the original motion sensor signal with any type of filter in any way, and/or using a pre-processing phase to offset the original motion signal in any direction by any amount, and/or using a post-processing phase to perform any of the previously mentioned approaches to reverse some or all of those changes, or to amplify some or all of said changes, or for any other purposes; criteria to follow any of these approaches include: increased accuracy, optimization of computational costs, increased dynamism in the solution, or any other. In some embodiments, any of the mentioned and/or any other additional approaches/methods/techniques/elements/processes and/or any variations and/or any combinations thereof may be used during the pre-processing, post-processing, and in-processing stages, in any way, for any purposes, and according to any criteria.

In some embodiments, the motion sensor leveraged to obtain the user's gait cadence may be an accelerometer; in some embodiments, the motion sensor may be a single-axis accelerometer; in some embodiments, the motion sensor may be a triaxial accelerometer, and each one of the axis may be used independently; in other embodiments, the motion sensor may be a triaxial accelerometer embedded within the device, and the three axial components may be leveraged to obtain a signal vector module; in other embodiments, the motion sensor may be a triaxial accelerometer, and the three axial components may be leveraged to obtain different combinations of correlations, which may be processed to obtain the fundamental frequency of the motion of the device; by way of example without limitation, some embodiments may use the correlation between accelerations of x and y axis and/or the correlation between x and z axis, and/or the correlation between y and z axis, and analyze the resulting signals in the time domain (e.g. event detection by means of thresholding using a moving average of the signal as threshold) or in the frequency domain (e.g. leveraging Short Time Fourier Transform), or by means of any other approach or combinations thereof (e.g. leveraging the wavelet transformation to obtain both time and frequency information of the signal), or any other techniques and/or combinations thereof for any purposes.

In some embodiments, the motion sensor may be embedded within the device; in other embodiments, the motion sensor may be in a wearable unit independent from the mobile device, and positioned in any way and in any location; in some embodiments the motion sensor may be a gyroscope; in other embodiments the motion sensor may comprise an accelerometer (uni-axial or tri-axial) and/or a gyroscope (uni-axial or tri-axial) and/or a magnetometer (uni-axial or tri-axial) and any sensor fusion techniques (e.g. Kalman filtering, particle filtering, or any other) may be leveraged to increase the accuracy of the solution or for any other purposes; in other embodiments, any or all of the mentioned sensors (accelerometer and/or gyroscope and/or magnetometer) may be embedded within the mobile device, and/or independently positioned in any location by means of separate wearable units in any way. Some embodiments may use any combinations of any of the previously mentioned approaches, and/or aspects, and/or elements, and/or processes, and/or any other, in any fashion.

In some embodiments, the time window considered to process the motion sensor signal may be offset over time in any fashion as additional samples from said motion sensor keep arriving for processing. By way of example without limitation, a four seconds time window may overlap 50% with the next four seconds time window selected for the next processing; in other words, the last half of the first time window coincides with the first half of the second time window. In other embodiments, different lengths of time window (e.g. 2, 4, 6, 20, 40 seconds or any other amount of seconds) and/or different overlapping factors and/or different approaches and/or combinations thereof may be used for the continuous processing of the motion sensor signal. In another example of embodiment, a four seconds time window may be selected to process the motion sensor signal every half a second, regardless of the motion sensor sampling frequency (downsampling, upsampling, filtering, and/or any other technique and/or combinations thereof may be leveraged to adapt to particular hardware and/or software conditions); in this example, the overlapping factor is larger than in the previous example, and the update frequency and dynamism (e.g. capability to quickly adapt to changes) of the solution have increased. In some embodiments, any possible overlapping factor, length of time window, update frequency, dynamism of the solution, and/or any other element/feature and/or combinations thereof may be selected. By way of example without limitation, a fixed length time window may be selected and said time window may be offset every time a new sample arrives from the motion sensor (accepting the new arriving sample and discarding the oldest sample from the fixed length time window (again, downsampling, upsampling, filtering, and/or any other technique and/or combinations thereof may be leveraged to adapt to particular hardware and/or software conditions, if needed)), in such a way that the update frequency of the solution may be equal to the sampling frequency of the motion sensor; in other words, we may obtain the fundamental frequency (or cadence) of a mobile device user with an update frequency equal to the motion sensor sampling rate; in some embodiments, by way of example without limitation, the device motion sensor sampling rate may be equal to 60 Hz, or 120 Hz, thus obtaining an update frequency for the user's cadence greater than the user's step frequency; this is an important aspect for certain applications requiring increased dynamism in the solution (for example to control an aspect of an application or to control a process in a mobile device with the user's cadence, with an update frequency greater than the user's step frequency, thus improving the user's experience over other approaches). In other embodiments, we may work with any other motion sensor sampling rates and leverage upsampling, downsampling, filtering or any other technique to obtain an update frequency for the user's cadence higher or lower than the user's step frequency.

In some embodiments, during the processing of the original motion sensor signal (e.g. signal from an accelerometer within the device) over a time window to determine the fundamental frequency (or cadence) using autocorrelation, a pre-processing phase may be included to filter said motion sensor signal in any fashion (e.g. filter as a result of a frequency analysis, e.g. Fourier analysis or any other, of said signal); by way of example without limitation, said signal may be applied a Fourier transformation from where the frequency components of said signal may be analyzed; in particular, focusing on the frequency components below a threshold of, for example, 0.5 Hz, and above 0 Hz, if these low frequency components are stronger than the rest of frequency components of the signal (e.g. their amplitudes in the Fourier transformation domain are larger than the amplitudes of the rest of frequency components of said Fourier transformation above 0.5 Hz), that may indicate a substantial orientation change experienced by the device.

The term substantial orientation change may be defined in some embodiments, by way of example without limitation, as any orientation change (in any number of dimensions) experienced by a mobile device that causes low frequency components other than those due to gravity (e.g. below a threshold of 0.5 Hz but larger than 0 Hz) of an accelerometer signal (the accelerometer being within said device), to have an amplitude (as observed, for example, through a Fourier transformation of said signal) larger than the rest of frequency components above the threshold of 0.5 Hz. In other embodiments, the threshold of 0.5 Hz to refer to low frequencies may be modified (made larger or smaller, but always keeping the sense of low frequencies in the context of gait analysis in which typical fundamental frequencies may approximately range from 1 Hz to 4 Hz), and the condition to be fulfilled by the amplitude of said low frequencies in comparison with the rest of frequencies may be relaxed (e.g. the maximum amplitude of said low frequencies may be above 80% (or 120% or any other figure that may depend on a plurality of criteria) of the maximum amplitude of any other frequency outside the low frequencies range); in some embodiments, different metrics/figures may be leveraged to refer to approximately the same term. By way of example without limitation, the term low frequencies may refer in some embodiments to the frequencies below the typical lower limits in the values of gait cadence (e.g. below 1 Hz) without considering frequencies due to gravity (typically 0 Hz); in some embodiments the upper threshold for low frequencies may be lower (e.g. below 0.5 Hz, or below 0.3 Hz, or any other value), and the term low frequencies may refer to any frequency that may allow the detection of a substantial orientation change experienced by the device, keeping the sense of low frequencies in the context of gait analysis in which typical fundamental frequencies may approximately range from 1 Hz to 4 Hz. In some embodiments, for example, if the upper threshold for low frequencies is very small (e.g. 0.3 Hz) and the Fourier transformation of the accelerometer signal offers low granularity in the selection of frequency components (e.g. there is only one low frequency component below said threshold and above 0 Hz), the detection of a substantial orientation change experienced by the device may comprise the comparison of the amplitude of that only low frequency with the amplitudes of the other frequency components obtained through the Fourier transformation. By way of example without limitation, frequency bands rather than setting thresholds may be used to refer to low frequencies or any other frequencies (e.g. in some embodiments, the low frequency amplitude(s) may be compared with a subset (e.g. a range of frequencies comprising the strongest amplitudes, or a range of frequencies comprising the previous values of cadence, or a range of frequencies comprised between certain thresholds, etc.) of the other frequency amplitudes); or energies of frequency components (either precise, specific frequency components or whole frequency bands or subbands, or any other) rather than amplitudes may be used; or any other possible modification and/or combination of any of the mentioned concepts/elements or any other may be used in other embodiments.

Substantial orientation changes may typically occur for example during movements and/or shakes performed by the user while carrying the device in his/her hand during a gait activity. In some embodiments, substantial orientation changes may refer to any type of orientation change experienced by the mobile or wearable device that distorts, and/or introduces noise in, and/or introduces artifacts in, and/or influences, and/or modifies the underlying information in the motion sensor signal about the gait movement, in any way. By way of example without limitation, said low frequency components due to a substantial orientation change may be strong enough to hide or distort or introduce noise or negatively influence or alter in any other way the underlying information relative to the original gait movement (e.g. the low frequency components may be so strong that an original fundamental frequency of e.g. 1.6 Hz may appear very weak (even negligible) in comparison with said low frequency components, to the extent that it could be interpreted that the fundamental frequency is now, for instance, 0.5 Hz instead of the real 1.6 Hz; any other type of distortions may also be considered. In cases of substantial orientation change, the original motion sensor signal may be filtered and/or processed in any fashion (e.g. by means of hardware and/or software) to mitigate and/or attenuate and/or counteract and/or influence in any way the distortion and/or noise and/or artifacts and/or influence and/or modification introduced by said substantial orientation change in the underlying gait information.

By way of example without limitation, as a result of a detection of a substantial orientation change, some embodiments may use a filter (e.g. high pass, or band pass) of any type (e.g. Butterworth, Chebyshev, or any other) or apply any type of pre-processing to try to eliminate the frequency components below 0.5 Hz (or any other threshold) from said motion sensor signal before being processed to determine the fundamental frequency. Taking into account the excellent qualities of wavelet transformation to, for instance, filter dynamic signals minimizing any extra distortion, we may apply a wavelet transformation to the original motion sensor signal (typical transformation parameters may be selected; by way of example without limitation: a mother wavelet from any of Haar, or Daubechies, or Coiflets, or discrete version of Meyer; and a number of levels of decomposition sufficient to account for the frequency bands we expect, which may depend on the number of signal samples we have, the length of the time window, or the sampling frequency; in a particular example, we may apply the wavelet transformation to the original motion signal using Haar mother wavelet and eight levels of decomposition; in another example, we may apply the wavelet transformation to the original motion signal using Daubechies type 3 mother wavelet and six levels of decomposition); once the wavelet transformation coefficients are obtained, a wavelet reconstruction may be applied avoiding low frequency components/coefficients (getting rid of any other frequency component may also be possible and convenient in certain conditions); by way of example without limitation, the avoided low frequency components/coefficients may include those below the previously mentioned threshold of 0.5 Hz. In other words, we filter the original motion sensor signal leveraging a wavelet transformation by obtaining its wavelet transformation coefficients and applying a wavelet reconstruction avoiding coefficients corresponding to frequencies below 0.5 Hz; in this way, the wavelet reconstruction performed with all coefficients but those corresponding to low frequencies will be a filtered version of the original motion signal. Consequently, in this particular example, we are determining in real time the device user's cadence through the analysis of the motion sensor signal by means of a combination of techniques comprising: Fourier transformation (e.g. to analyze the frequency components of the motion sensor signal and decide if the signal needs to be filtered), wavelet transformation (to filter the signal), and autocorrelation of the filtered signal. In some embodiments, any modifications and/or combinations of any of the elements and/or processes and/or techniques mentioned and/or any other, may be applied in any fashion.

In some embodiments, abrupt changes in cadence (or motion sensor signal fundamental frequency) may be detected leveraging frequency and time information of the motion sensor signal. By way of example without limitation, abrupt changes in cadence may be characterized by sudden and/or fast (typically within a few seconds or even within fractions of a second) modifications in the value of said cadence; and wherein said abrupt modifications typically involve a relative change in the value of said cadence of at least 25% (e.g. a change from 2 Hz to 1.5 Hz involves a reduction of 25% relative to 2 Hz), although other values, larger and/or smaller, may also be considered. By way of example without limitation, abrupt changes in cadence may comprise: a change from 2 Hz to 1 Hz in the walking cadence of a mobile device user in a matter of 2 seconds, or a change from 2.1 Hz to 1.2 Hz in the walking cadence of a mobile device user in a matter of 2 steps, or a change from 0.8 Hz to 1.5 Hz in the walking cadence of a mobile device user in a matter of 3 steps, or a change from 1.9 Hz to 3.35 Hz in the gait cadence of a mobile device user in a matter of 1.5 seconds while he/she changes his/her gait from walking to running, or a change from 3.2 Hz to 1.8 Hz in the gait cadence of a mobile device user in a matter of 3.5 seconds while he/she changes his/her gait from running to walking, or any other possible combinations reflecting an important change in the value of the cadence (e.g. a factor of approximately 2 or less or more when the cadence is increased, and/or a factor of approximately 0.5 or less or more when the cadence is decreased) performed in a short period of time (typically within a few seconds).

Traditional approaches to determine cadence may fail when facing abrupt changes in cadence, because their processing of the motion signal may assume, for instance, a selected minimum time length of the user's step, or a selected frequency range of the user's cadence; the problem may be specially important when the abrupt changes in cadence (e.g. from 1 Hz to 2 Hz) result in the new cadence value (2 Hz) occupying some harmonic frequency of the previous values of cadence (1 Hz), in such a way that traditional methods may think of the new cadence value (2 Hz) as an harmonic of the previous cadence value (1 Hz), and find a subharmonic (½) of the new cadence (2 Hz) to be considered as the real cadence because it matches previous cadence values (1 Hz); consequently, traditional approaches would keep wrongly tracking said subharmonic as the fundamental frequency. Other examples may comprise any possible combinations and/or modifications of any of the concepts (including harmonics, subharmonics, and their orders) and/or figures and/or elements of the previous examples. It is worth noting that the problems may also arise with changes in cadence not necessarily involving integer multiples and/or submultiples of the original fundamental frequency.

In some embodiments, abrupt changes in the device user's cadence may be detected leveraging frequency and time information of the motion sensor signal (e.g. accelerometer signal, wherein said accelerometer is within the device). By way of example without limitation, we consider a mobile or wearable device user walking, and transitioning his/her cadence from 0.5 Hz to 1 Hz (other examples of embodiments may use different cadence values), whereby the device comprises a triaxial accelerometer with a sampling frequency of 50 Hz; the new value of 1 Hz for cadence has been determined (810) using e.g. any of the approaches described in this specification, but the new value is suspicious of being an error, because of the abrupt change in cadence (820). Consequently, there is a need to confirm as genuine the new cadence value, or reject it because it may be considered that the newly determined cadence is an error caused by harmonics of the previous cadence value (0.5 Hz). In other words, there is a need to detect genuine abrupt changes in cadence, and thus confirm as genuine the newly determined value of cadence. For this, a process composed of several stages will be explained next.

First, a pre-processing stage may comprise the identification of the accelerometer axis whose mean has the highest absolute value among the three axes, and/or the identification of two of the accelerometer axes whose means have the lowest absolute value among the three axes (830) (e.g. we identify the three axes of the accelerometer X, Y, and Z, and obtain the mean in the time domain for each one of them over a time window of, for example, four seconds (some embodiments may use windows with different time lengths, including e.g. 2, 6, 20, 40 seconds or any other amount of seconds); we obtain the absolute value of said obtained means, and compare them to identify the two accelerometer axes with the lowest means in absolute value; other embodiments may use any other length of time window or any other modifications according to criteria comprising: computing and/or storing costs and/or any other; other embodiments may use any other approaches and/or modifications and/or combinations thereof).

Once the two axes with the lowest means in absolute value have been identified (e.g. axes X and Y), an indication of a metric accounting for the average frequency value of the main (strongest) frequency components recorded over a pre-determined time window may be obtained for each of said two axes (840); for instance, said metric may be computed over a time window comprising the past twenty seconds; in some embodiments, different lengths of time window may be used (larger or shorter depending on criteria comprising accuracy, computing and storing costs, etc.), or different variables may be used for continuous updating of said metric with every new measurement/sample/processing obtained from the accelerometer signal, in such a way that there is no need to keep a window of past values; in other embodiments, different metrics may be used; for example, probabilistic models can be used to obtain a metric accounting for the strength/power and/or frequency value of each main frequency component recorded and the length of time during which said component was active; in other embodiments the metric may account for the frequency value of said component and the amount of time said value has been active over a length of time; other embodiments may use any combinations of any of said elements and/or concepts and/or any others in any fashion. For clarity purposes, we can call said determined indications X_probabl_freq and Y_probabl_freq (for X and Y axes respectively); in some embodiments, said determined indications may be retrieved leveraging any of the previously described approaches and/or using small databases, and/or registers, and/or look-up tables, and/or any kind of variables recording continuous updates in an application.

After determining said indications X_probabl_freq and Y_probabl_freq, the two previously identified axes (e.g. axes X and Y), are classified according to said indications (850); for example, if axis X has a value of said determined indication larger than axis Y, we can call axis X as primary axis and axis Y as secondary axis. Next, to check if there has been a genuine abrupt transition in the fundamental frequency, we focus (860) on a range of frequencies around the previously determined fundamental frequency (0.5 Hz), and we check if the current strength of the so called primary axis in a frequency band around the previously determined fundamental frequency is at least a threshold below the current strength of the so called secondary axis in the same frequency band (870); this strength comparison can be performed in terms of energy (e.g. using energy of a frequency component or energy of a frequency band, which can be determined for example leveraging a Fourier transformation or a wavelet transformation), or in terms of amplitude (e.g. using amplitude of a frequency component which can be determined for example through a Fourier transformation), or in terms of any other concept and/or element and/or any combinations thereof. Regarding the threshold for the strength comparison, recommended values for increased accuracy may be, by way of example without limitation: the larger quantity should be at least 2.25 times the smaller quantity if the comparison is made in terms of energies, or the larger quantity should be at least 1.5 times the smaller quantity if the comparison is made in terms of amplitudes; in some embodiments, different values (larger or smaller) may be used to account for particular conditions that may recommend tightening or relaxing said threshold. In some embodiments, any variations of any figures/concepts/approaches and/or any other and/or combinations thereof may be used.

In affirmative case regarding the previously referred strength comparison, we retrieve a history (880), over a pre-determined length of time right before the current time, of the values of the energies of both primary and secondary axes in the frequency band around the previously determined fundamental frequency (0.5 Hz); in some embodiments, said history of the values of the energies of both axes may span over several seconds (e.g. 10 seconds, although other values may also be possible depending on criteria comprising computing costs, storage costs, sampling frequency and/or any other), and it should be large enough to be able to register the transition. In some embodiments, instead of energies, the history of values may be of amplitudes of frequency components, obtained, for example, through the Fourier transform. In other embodiments, other approaches and/or figures and/or techniques and/or combinations thereof may be used.

Next, calling oldest_time_instant the instant of time corresponding to the oldest value registered in the previously mentioned history of values of strength (for clarity, it is worth remembering that strength can be expressed in terms of energy or amplitude or any other depending on the chosen approach), we check if the following three conditions are fulfilled: 1) the strength of the so called secondary axis over said frequency band at said oldest_time_instant is at least a threshold below the strength of the so called primary axis over the same frequency band at the same oldest_time_instant (881), and 2) the current strength of the so called primary axis in said frequency band is at least a threshold below the average strength of the primary axis in the same frequency band over the span of said history of values of strength (882), and 3) the current strength of the so called secondary axis in said frequency band is at least a threshold above the average strength of the secondary axis in the same frequency band over the span of said history of values of strength (883); if said three conditions are fulfilled, then some embodiments may consider that an abrupt transition in cadence has been detected (890), and consequently, the most recently determined fundamental frequency (1 Hz) is verified as genuine (891); otherwise, it would have been rejected (892) and some embodiments may use said rejection to try to keep tracking the old cadence values of 0.5 Hz (e.g. leveraging an adaptive filter centered at the old cadence values to emphasize them and reject what could be considered as errors due to harmonics, or with any other approach). Again, as previously described, regarding the threshold for the strength comparison, recommended values for increased accuracy may be, by way of example without limitation: the larger quantity should be at least 2.25 times the smaller quantity if the comparison is made in terms of energies, or the larger quantity should be at least 1.5 times the smaller quantity if the comparison is made in terms of amplitudes; in some embodiments, different values (larger or smaller) may be used to account for particular conditions that may recommend tightening or relaxing said threshold. In some embodiments, any variations of any figures/concepts/approaches and/or any other and/or combinations thereof may be used.

In some embodiments, a combination of time domain techniques and frequency domain techniques (e.g. Fourier transformation) may be used to detect abrupt changes in cadence; in other embodiments, techniques providing both time and frequency information (e.g. wavelet transformation) may be used; in other embodiments, combinations of any of those techniques and/or any other may be leveraged to obtain the time and frequency information to allow detection of abrupt changes in cadence. In other embodiments, any other modification and/or combination of any element and/or approach and/or technique and/or figure and/or combinations thereof may be used.

Some embodiments may leverage the previously mentioned information about the user's steps in combination with other metrics to enhance user's dynamics information, comprising velocity and activity. It is worth noting that in some embodiments, the user's cadence may be considered as the user's step frequency (inverse of the user's step time period). Some embodiments may leverage the obtained information on user's steps in combination with the information on user's dynamics to determine stride length. By way of example without limitation, using the physics principle velocity equals distance over time, once we have determined velocity, we can obtain distance (e.g. stride or step length) by using the time of each stride or step (step frequency (cadence) equals inverse of the user's step time period). Some embodiments may leverage the information on user's dynamics to compute distance. Some embodiments may enhance distance through the combination of user's dynamics information with localization information. Some embodiments may use different techniques, principles and/or methodologies to obtain all the previous information and metrics, including but not limited to machine learning. In some embodiments, all the computation, processing, information presentation, and other steps may be carried out within a single mobile device without the need of external resources. In some embodiments, the computation or some other step or combinations of steps may be performed external to the mobile device, or with the assistance of some external element, such as external sensor, server, database or any other element. In some embodiments, software may be stored on the mobile or wearable device, for instance, in its memory for execution by its processor or processors. Some embodiments may store data structures and code on computer readable storage medium, which by way of example, and not limitation, may comprise field-programmable gate arrays, application-specific integrated circuits, magnetic and/or optical storage devices, etc.

In some embodiments, the sensor portion of the device or the device itself or any other device containing a sensor and with the capability to communicate in any fashion with the user's device, or any other type of device or accessory may be positioned or attached to any part of the user, including by way of example without limitation, the wrist, arm, hand, face, head, waist, chest, pocket, hat, shoe, any type of clothing, accessories and any combinations thereof and in any way. In some embodiments, the system may be trained to recognize and/or learn activity, motion type, attachment position of the device, movement characteristic, etc. In some embodiments, analysis of acceleration signature may help determine activity, motion type, attachment position of the device, movement/gait characteristic, etc. By way of example without limitation, the acceleration signal may be processed to identify maximums, minimums, mean, standard deviation, frequency components, period, orientation, distribution of peaks, patterns, etc. and/or combinations thereof in order to help determine activity, motion type, attachment position of the device, movement/gait characteristic, etc. In some embodiments, Fourier analysis, any kind of filtering, peak counting, determination of frequency components leveraging the wavelet transform or any other method and combinations thereof may also be utilized to determine user's gait activity, characteristics, etc. In some embodiments, any type of prompt to the user may also be leveraged to request information about his/her activity, motion type, attachment position of the device, movement/gait characteristic, etc. In some embodiments, activity, motion type, attachment position, movement/gait characteristic, etc. may be determined through correlation of any type of sensor values or any type of parameter or metric generated with them, based on any type of model that has been calibrated in any fashion for a particular activity, motion type, attachment position, movement characteristic, etc. In some embodiments, any other sources, means, methods and/or configurations may be leveraged to determine activity, motion type, attachment position, movement/gait characteristic, etc., including by way of example without limitation, the use of sensors and/or signals obtained independently of the sensed acceleration (e.g. GPS), the use of statistics and/or any other empirical information, algorithms, databases or other information stored anywhere and in any fashion, combinations thereof, etc. In some embodiments, the referred methods, configurations, systems, etc. may be modified, updated and/or calibrated in any way, periodically or continuously over any time interval.

Some embodiments may include any external sources to obtain any parameter or information about movement, environment, context, etc. including by way of example without limitation, speed and/or distance monitors, any number of portable electronic devices (e.g. GPS receivers, any kind of computing and/or communications device, etc.), databases and/or networks. In some embodiments, other types of inputs may also be utilized, including by way of example without limitation, buttons, keys, keyboards, keypads, touchpads, joysticks, etc., which may be used in any fashion. Any type of satellite based navigation systems, cellular communications networks and other systems/networks may also be used to obtain speed in some embodiments (and/or provide feedback to help correct errors) under certain conditions.

In some embodiments, additional inputs may include traces from touch-sensitive screens, button presses, gesture recognition, voice commands, switches, and/or any other type of technological, physical or any nature means that allow the user to interact, and combinations thereof. In some embodiments, in addition to using gait characteristic for control, further control may be performed through any additional movements that the user may perform with the device, such as any type of tilting or any kind of gestures, including by way of example without limitation, any kind of raise, swing, twist, touch, press, swipe, drag, double touch, pinch, etc., and combinations thereof, regardless of performing them with or without direct contact to the device screen or any other element (e.g. the user may perform the pinch gesture touching a screen or in the air without touching a solid element). In some embodiments, any type of method may be employed to distinguish between different types of gestures, swings, twists, etc. that the user makes while he/she performs a pedestrian activity (e.g. walk, jog, run, etc.); by way of example without limitation, frequency analysis, filtering, acceleration thresholding, analysis of projection of gravity vector, feedback from other sensors, or any other technique/method and combinations thereof may be employed.

In some embodiments, the acceleration sensor may be an electrostatic or capacitance-coupling type, or any other technology (e.g. piezoelectric or piezoresistance type) now existing or later developed, and may be configured to deliver three-axis, two-axis, or one-axis acceleration. In some embodiments, in addition to accelerometers, any other type of technologies and/or sensors such as gyroscopes, magnetometers, pressure sensors, cameras, GPS, etc. may be used in any way to enhance accuracy or for any other purposes. In some embodiments, the user may have any number of any type of sensors, sensor units, devices, or accessories located anywhere in any fashion to determine the characteristics of his/her movement and/or for control or any other purposes.

In some embodiments, any processing, detection, recognition, or any other actions or operations may be performed regardless of the mode, state or any other condition of the device, application or any other entity, process or element. In other embodiments, any number of conditions and/or criteria of any type must be satisfied before proceeding with any of said actions or operations.

Any of the embodiments herein described may be implemented in numerous ways, including as a method, an apparatus, a device, a system, a computer readable medium, etc., and also be applicable in any environment, application (game, non-game, etc.), condition, etc. regardless of number of users, physical proximity, communication means, device, or any other factor.

Other configurations are also possible. By way of example, and not limitation, in some embodiments, all or part of the processes may be performed by chip-level systems, third-party applications, operating system kernel, firmware, or any other combination of hardware and/or software. In some embodiments, the software may be delivered in a variety of forms, including but not limited to, as stand-alone application, as library, as application programming interface, etc. In general, the functions of particular embodiments may be achieved by any means as is known in the art. Some embodiments may use distributed, networked sensors and/or systems, components, servers, databases, and/or circuits, and/or any combination of additional hardware and/or software and/or processing techniques and methodologies. Some embodiments may use any other type of sensor and/or system.

In some embodiments, sensors may be any of several types including, by way of example, and not limitation, any type of device, transducer or any other type of apparatus which may measure some quantity; in some embodiments, sensors may be implemented in any size, with any type of technique and technology, including but not limited to electronic, microelectronic, nanoelectronic, etc. By way of example, and not limitation, sensors may comprise any type of accelerometer, magnetometer, gyroscope, pressure sensor, proximity sensor, etc. and any other type of device sensitive to radio-frequency, sound, ultrasound, light, etc. including but not limited to, GPS antennas and/or their sensitive elements, WiFi antennas and/or their sensitive elements, and any other type of radio-frequency technology antennas and/or their sensitive elements. In some embodiments, sensors are integrated within the mobile or wearable device. In some embodiments, sensors or other mobile or wearable devices may be distributed outside the main mobile or wearable device, and they may communicate with the main mobile or wearable device by any means. Communication or transfer of data may be wired, wireless, or by any other means. In some embodiments, the user or other entity may rearrange characteristics of the components, or other features or elements of the system and the system may automatically adjust to new settings or arrangements.

Figure 7:
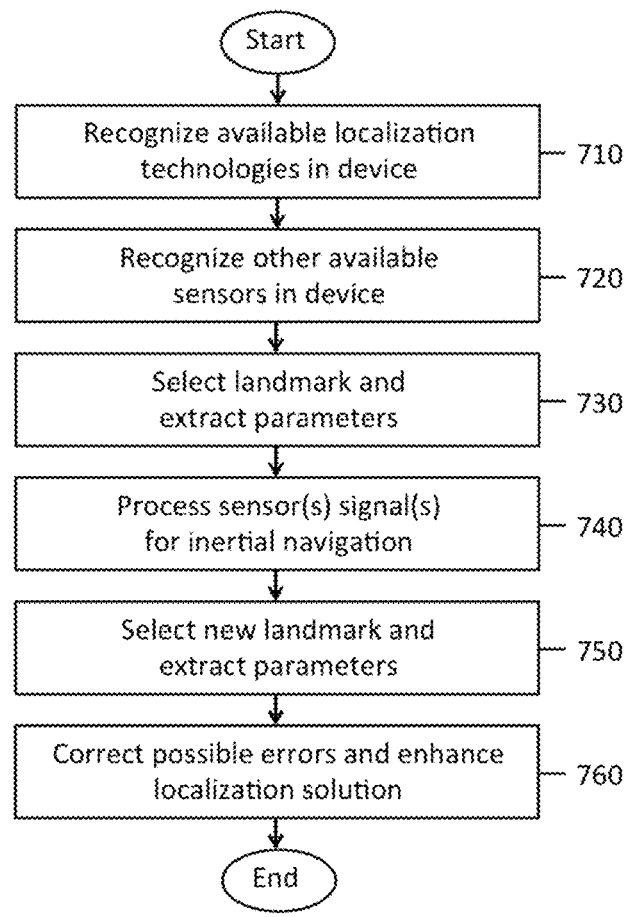
FIG. 7 illustrates a flow diagram for the process to enhance a user's dynamics and localization information according to one embodiment.
Figure 8:
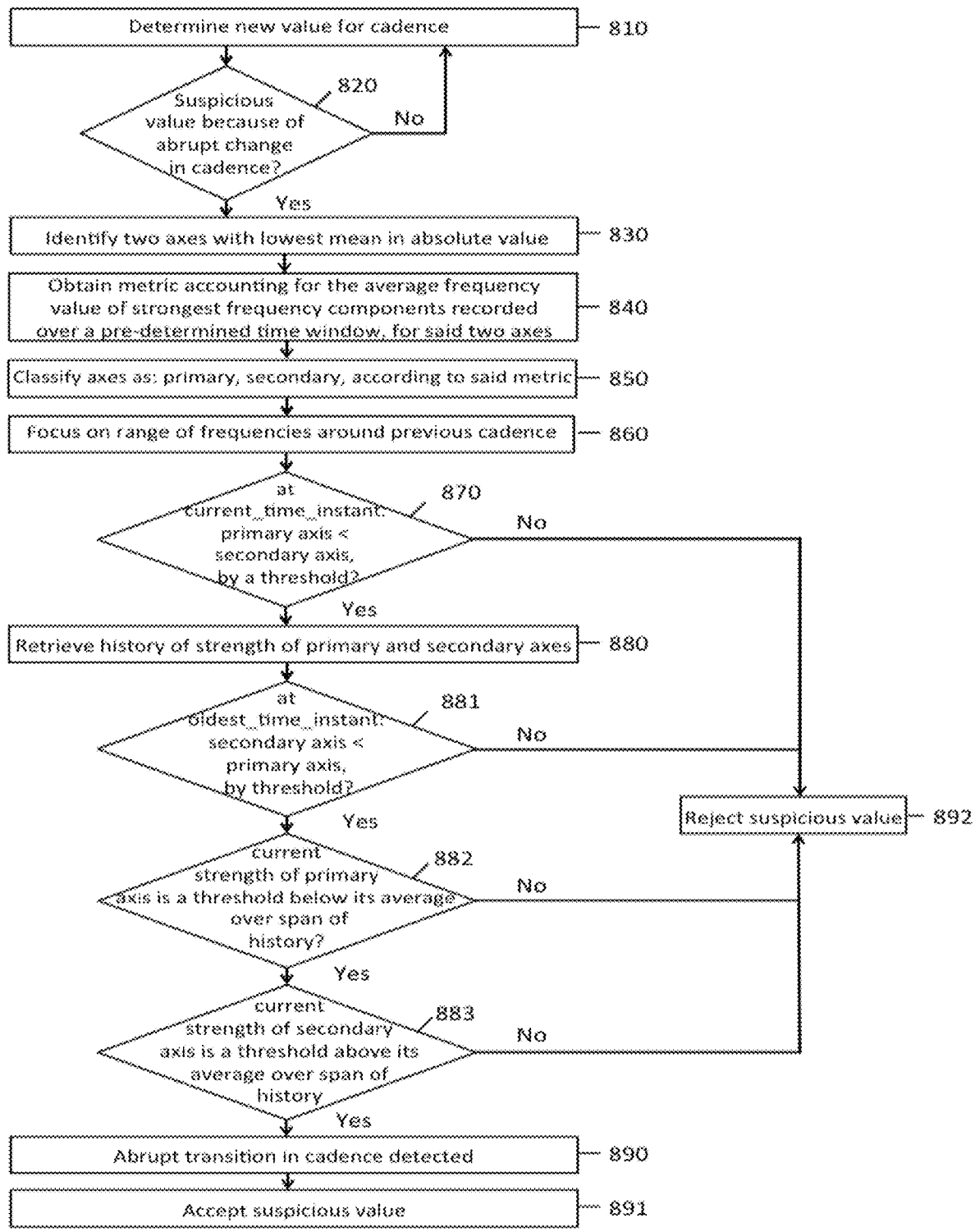
FIG. 8 illustrates a flow diagram for the process to detect an abrupt change in cadence according to one embodiment.

In some embodiments, a method for enhancing a user's dynamics and localization information may be used as shown in FIG. 7, which illustrates a flow diagram of possible basic steps. This Figure and its elements (710), (720), (730), (740), (750), and (760) are further described in application Ser. No. 14/922,174 and application Ser. No. 16/044,833.

Some embodiments may use all the available information to identify the position (and transitions between positions) of the mobile device within the user's body, as described in application Ser. No. 16/044,833.

Analogously, some embodiments may leverage any machine learning algorithm/methodology (e.g. support vector machine, decision tree, Naïve Bayes, or any other) to determine any gait attribute(s) (e.g. velocity and/or stride length and/or calories burned per time unit and/or activity and/or device position and/or other and/or any variations and/or combinations of any number of them), in a device process and/or application and/or in the context of controlling a user's representation, making use of the determined user's cadence (or fundamental frequency) as a feature for the determination of said gait attribute(s). For example, we can follow any of the procedures described within this application or any other to determine a gait attribute leveraging a machine learning algorithm and a training set of data to model said attribute, so that said model can be implemented in the device process and/or application and/or in the context of controlling a user's representation, and used to determine said gait attribute(s) by leveraging a set of features computed for said determination (in real time and with an update frequency larger than the user's step frequency or any other). In some embodiments, the features computed for said determination include the user's gait cadence; consequently, cadence will need to be also computed and recorded during the gathering of training data; in some embodiments, the features computed for said determination include the user's gait cadence and/or mean and/or variance and/or standard deviation and/or skew and/or kurtosis and/or principal frequency component and/or energy in selected frequency bands, and/or any other obtained from e.g. accelerometer data over a time window; in other embodiments, any variations and/or combinations thereof may also be possible. Some embodiments may use any of the procedures/strategies/methodologies described within this application and/or any other for the determination of the user's cadence to be used as a feature, including, by way of example without limitation: 1) analyzing a motion sensor signal using a combination of techniques comprising: wavelet transformation, Fourier transformation, and autocorrelation and/or 2) detecting abrupt changes in the user's cadence leveraging frequency and time information of the motion sensor signal.

FIG. 9A, 9B, 9C, 9D, 9E, 9F show scaled representations of images strip files used for animation. They have been scaled to fit in the document of this patent application, but their sizes can be chosen depending on a plurality of criteria, including by way of example without limitation, the available memory for the application using said images strips in the mobile or wearable device, the amount of heap memory expected to be used by the application in the mobile or wearable device, the screen size (e.g. physical size in terms of height millimeters*width millimeters or height pixels*width pixels) of the mobile or wearable device where said images strips are going to be used, the proportion of the device screen expected to be occupied by the animation, the density of the screen of the device (e.g. number of pixels per squared inch), the available storage capacity of the mobile or wearable device, any design and/or esthetic choices made by the developer of the application, and/or any other criteria and/or variations thereof and/or any combinations of any of the elements, criteria, and/or any other.

In a particular embodiment intended for an application in an Android device, FIG. 9A, 9B, 9C, 9D, 9E, 9F may represent images strip files with png extension (other file formats, e.g. jpg extension or others, may also be possible) stored in the "assets" folder of the mobile application, or in the "res/drawable-mdpi" folder of the mobile application, or in any other appropriate possible location chosen by the application developer. Criteria to choose folder in which to store the images strip files may include, by way of example without limitation: the expected density of the device screen (e.g. folder name with extension of: mdpi is usually assigned to resources for medium-density (mdpi) screens (~160 dpi), ldpi to resources for low-density (ldpi) screens (~120 dpi), hdpi to resources for high-density (hdpi) screens (~240 dpi), xhdpi to resources for extra-high-density (xhdpi) screens (~320 dpi), xxhdpi to resources for extra-extra-high-density (xxhdpi) screens (~480 dpi), xxxhdpi to resources for extra-extra-extra-high-density (xxxhdpi) uses (~640 dpi), etc.), the way the operating system of the device handles image files (bitmap files) in memory, the resources of the device (e.g. storage capabilities, memory, etc), and/or any other and/or any variations and/or combinations thereof. In one example of embodiment, FIG. 9A, 9B, 9C, 9D may be images strip files with png extension stored in the "assets" folder, with dimensions: 3146 pixels*145 pixels (again, sizes can be chosen depending on a plurality of criteria, as discussed above), with color space RGB (although in this patent application drawings have been grayscaled), containing 26 (in other embodiments, may contain 22, 16, or other numbers depending on criteria such as: type of activity being displayed, expected gait frequency of the activity, etc.) frames (sub-images) corresponding to a complete gait cycle (e.g. 26 frames span one complete gait (walking, jogging, running, or any other activity) cycle). In other words, these images strip files contain 26 frames (26 sub-images of 121 pixels*145 pixels each) arranged consecutively and timely ordered in such a way that displaying the frames consecutively in a device screen one after the other fast enough (e.g. frequency larger than 12 Hz) to make the human eye perceive them as continuous movement, we can achieve the effect of animation; this is a well-known technique used for example in cinemas, displaying consecutive frames fast enough (e.g. frequency of approximately 25 Hz), to achieve the illusion of animation to the human eye. By way of example without limitation, if the 26 frames are displayed on the device screen sequentially and continuously and cyclically repeated (frame 1, frame 2, frame 3, . . . , frame 25, frame 26, frame 1, frame 2, frame 3, . . . , frame 25, frame 26, frame 1, frame 2, . . . , and again and again), the device user will have the illusion that the person in the frames is walking continuously.

Figure 9A:
FIG. 9A, 9B, 9C, 9D, 9E, 9F show images strip files for a representation of a user with different gait attributes according to one embodiment.
Figure 9B:
Figure 9C:
Figure 9D:
Figure 9E:
Figure 9F:

FIG. 9E, 9F may represent images strip files with png extension, stored in the "assets" folder, with dimensions: 2662 pixels*145 pixels and 1936 pixels*145 pixels respectively (again, sizes can be chosen depending on a plurality of criteria, as discussed above), with color space RGB (although in this patent application drawings have been grayscaled), containing a number of frames of 22 and 16 respectively. In this example of embodiment, FIG. 9E, 9F represent complete cycles of running for a person, in contrast with FIG. 9A, 9B, 9C, 9D, which represent complete cycles of walking. It is worth noting that in this particular embodiment, FIG. 9E, 9F may have a number of frames (e.g. 22, 16) different from FIG. 9A, 9B, 9C, 9D (e.g. 26 frames), because FIG. 9E, 9F represent running cycles, while FIG. 9A, 9B, 9C, 9D represent walking cycles. In general, running cycles may be carried out faster than walking cycles, so the number of frames needed to cover a whole cycle (achieving good illusion of animation to the human eye) may be smaller for running than for walking. And even representing the same activity (e.g. running), an images strip file may have even smaller number of frames (e.g. 16 instead of 22) if the running activity represented in said strip is expected to be carried out at a faster frequency (e.g. FIG. 9F represents a running mode faster than the one represented in FIG. 9E, and consequently, it can use a smaller number of frames to complete the cycle, still achieving good illusion of animation to the human eye). On the other hand, some embodiments may use the same number of frames for all image strips regardless of the activity represented, following criteria including, by way of example without limitation, prevention of memory management problems (e.g. images strip files with different number of frames generally will have different sizes in terms of number of pixels (pixels height*pixels width), which will translate into allocations of blocks of memory of different sizes (typically the amount of memory allocated for an image file or a bitmap file may be equal to the number of pixels in height of the image, multiplied by the number of pixels in width of the image, multiplied by 4, if the amount of information bits used per pixel is 4); for instance, in the previous example, where the walking images strips have a size of 3146 pixels*145 pixels, the amount of memory allocated for each strip is: 3146*145*4~=1.8 MB; if the application is running low on memory, a procedure called garbage collection may be triggered to free unused blocks of memory; however, if we need to allocate a new image and the available memory is fragmented into small blocks of different sizes, none matching with the size required to allocate our new image, the application could face an "out of memory" error, which in some circumstances could be prevented if we use image files of the same size, and release or recycle an unused image file before trying to allocate a new image file). Different embodiments may have images strips with different numbers of frames (even if the strips represent the same type of activity). Other embodiments may use different approaches/methodologies and/or any others and/or any variations and/or combinations thereof.

In some embodiments, the user's representation shown in the images strip files (e.g. the person in FIG. 9A, 9B, 9C, 9D, 9E, 9F, 10A, . . . 10F) may take any other form(s), including, by way of example without limitation, any type of person, avatar, object, vehicle, robot, and/or any of the entities/forms mentioned in reference to element (110) in FIG. 1C, and/or any other elements in FIG. 1C and FIG. 2B, with any characteristics, and/or any other, and/or any variations and/or combinations thereof.

Since we want to show in real time changes in the user's representation being displayed on the device screen when the device user changes his/her gait (and/or gait attribute(s)), we can use different images strip files with different characteristics to show the differences brought by the change in the user's gait. By way of example without limitation, FIG. 9A, 9B, 9C, 9D represent walking cycles, but with different characteristic for the person being displayed on the screen; for instance, FIG. 9A displays a relatively short stride length for the person displayed, while FIG. 9B shows a bit larger stride length, FIG. 9C shows a larger stride length, and FIG. 9D shows a very large stride length; on the other hand, FIG. 9E, 9F represent running cycles, but also with different characteristic for the person being displayed on the screen; for instance, FIG. 9E displays a relatively short stride length for the person displayed as running, while FIG. 9F shows a larger stride length for the person displayed as running. These and other details can be observed more clearly in FIG. 10A, 10B, 10C, 10D, 10E, 10F, which represent scaled (zoomed in) portions of FIG. 9A, 9B, 9C, 9D, 9E, 9F respectively; in particular, we can see that the walking cycles represented in FIG. 10A, 10B, 10C, 10D, present different characteristics in the person being displayed; for instance, the stride length increases progressively from FIG. 10A to FIG. 10D, but there are also progressive changes in other details, such as, by way of example without limitation, the swing of the arms, the angles of the knees when taking new steps, the angles of the elbows, the back and forth movement of the head (achieved e.g. through appropriate rotations of the bone(s) controlling the head movement), the rotation of the hips, the rotation of the shoulders, the rotations of the feet, the change in elevation of the hips, the forward angle of the upper body, etc; these details and additional ones may be seen more clearly in FIG. 10E, 10F, which represent different running cycles, also showing differences in, by way of example without limitation, the way the fingers in the hands are grouped together in the form of a fist, the way the forearms shake, the way and angles in which the arms rotate, the angles of the thighs with the vertical direction, the angle at which the feet land on the ground with every step, the way the hair moves and bounces with every step, etc. In some embodiments, all the parts of the body shown in any of the figures FIG. 9, FIG. 10, may be controlled (e.g. their location, rotation, scale, surface texture, material, color, etc. may be chosen/modified/controlled by the designer rendering them appropriately, and/or by a programmer selecting their values/features programmatically, etc.) following any criteria.

In one example of embodiment, the effect of animation to the human eye can be achieved as described next. First, we are making the following assumptions for this particular example of embodiment: the mobile device the user is carrying is a smartphone; the operating system of the mobile device is Android; other embodiments may use different devices (e.g. smart glasses, smart watches, and/or any other type of mobile or wearable device, running in any type of operating system (by way of example without limitation, iOS by Apple, or any other)); the version of the operating system is Android 6.0.1. The mobile device has a touch screen of 4.5 inches (480 pixels*854 pixels), a 1.1 GHz Quad Core chipset, 1 GB RAM+8 GB ROM, supports microSDXC card up to 32 GB, and has the typical wireless and other type of functionalities of an average smartphone. An application is developed for said example of smartphone (again, other embodiments may use any other type of device, characteristics, elements, and/or any other and/or any variations and/or combinations thereof) using any of the available software and/or hardware and/or any other type tools (e.g. a MacBook Pro with OS X El Capitan, processor of 2.4 GHz, memory of 8 GB, equipped with integrated development environment such as Eclipse or Android Studio, together with any available plugins, tools (e.g. Android Development tools, Android SDK tools, or any other), and/or any other elements if needed). One possible example of embodiment for the developed Android application can be described with the help of the Java-style pseudocode in FIG. 11A, 11B, which will be used to discuss details of how the animation (or control of the user's representation) can be achieved on a mobile device screen in one embodiment. Different embodiments may use different approaches, and even the same approach can be tackled in different ways using a variety of alternative software and/or hardware resources; any modifications and/or combinations of any elements and/or procedures and/or any other type of entity may also be possible in some embodiments. As shown in FIG. 11A, a class extending the SurfaceView class and implementing the SurfaceHolder.Callback interface may be created, named AnimationView; one of the purposes of the SurfaceView class is to provide a surface in which a secondary thread can render into the screen; when used in this way, we should to be aware of some threading semantics: 1) All SurfaceView and SurfaceHolder.Callback methods will be called from the thread running the SurfaceView's window (typically the main thread of the application). They thus need to correctly synchronize with any state that is also touched by the drawing thread. 2) It is important to ensure that the drawing thread only touches the underlying Surface while it is valid—between SurfaceHolder.Callback.surfaceCreated( ) and SurfaceHolder.Callback.surfaceDestroyed( ). The SurfaceHolder.Callback interface may be implemented to receive information about changes to the surface.

Within the AnimationView class, a class named AnimationThread may be created extending the Thread class and implementing the interfaces SensorEventListener (used for receiving notifications from the SensorManager when sensor values have changed), and OnTouchListener (for a callback to be invoked when a touch event is dispatched to the view. The callback will be invoked before the touch event is given to the view). A Thread is a concurrent unit of execution. It has its own call stack for methods being invoked, their arguments and local variables. Each application has at least one thread running when it is started, the main thread, in the main ThreadGroup. The runtime keeps its own threads in the system thread group. There are two ways to execute code in a new thread. You can either subclass Thread and overriding its run( ) method, or construct a new Thread and pass a Runnable to the constructor. In either case, the start( ) method must be called to actually execute the new Thread. Each Thread has an integer priority that affect how the thread is scheduled by the OS. A new thread inherits the priority of its parent. A thread's priority can be set using the setPriority(int) method.

Focusing on FIG. 11A, the 12 lines following the first 2 lines, are used to declare some variables needed for the management and drawing of the images. For instance, imagesStrip is defined as a Bitmap to hold the information (in memory) of the image strip file we want to work with; frame_0_StartTime is defined as a long variable to hold the time (in milliseconds) at which the 0th (in other words, first) frame was started to be displayed on the screen, thus serving as an origin reference point in time; beginning_manageCurrentFrame is defined as a boolean variable (initially set to true) to indicate whether we are entering the manageCurrentFrame method for the first time; once said method is entered (and if currentFrame is equal to zero), beginning_manageCurrentFrame will be set to false; timeIntoCompleteAnimation is defined as a long variable to hold the time (in milliseconds) elapsed since an origin reference point in time, thus allowing us to know how deep into a complete animation cycle we are in terms of time; frameCount is defined as an integer variable (set to 26 in this particular example, but any other values are also possible, and it could even be changed programmatically in the application), and its purpose is to account for the number of frames (sub-images) in the images strip file(s) (e.g. with extension png) we are working with; in some embodiments, it may be advisable to keep frameCount constant across different images strip files to prevent memory segmentation that could lead to "out of memory" errors under some circumstances (e.g. low memory conditions); completeAnimationPeriod is defined as an integer variable, and its purpose is to hold the amount of milliseconds a complete animation period should last (initially set as 1000 in this particular example, for instance, assuming 2 Hz cadence, the complete animation (2 steps) period=1 second=1000 milliseconds; nevertheless this value should be programmatically changed based on the determined cadence or fundamental frequency of the user; for instance, if the determined cadence is 1 Hz, the complete animation (2 steps) period=2 seconds=2000 milliseconds); currentFrame is defined as an integer (initially set to zero), and its purpose is to account for the order of the frame (e.g. from 0 to 25 if we work with 26 frames, and cyclically repeating (e.g. . . . , 24, 25, 0, 1, . . . )) within the images strip file we are working with, that is to be displayed on the screen for the purpose of achieving animation to the human eye; frameWidth and frameHeight are defined as integers (initialized to 300 and 360 in this particular example, but other values are also possible), and their purpose is to set the actual dimensions of the frame when displaying it on the device screen, in terms of the actual number of pixels the frame will occupy on the screen of the device.

It is worth noting that these values can be modified in any way for other embodiments depending on a plurality of criteria, including by way of example without limitation, the physical size of the screen of the device, the density of pixels of the screen, the amount of heap memory an application is allocated in the device, the amount of heap memory an application is expected to allocate for bitmaps, design criteria of the developer, and/or any variations and/or combinations thereof; it is also worth noting that these numbers do not need to match the actual physical dimensions of the frames in the images strip file (e.g. png extension), because Android OS allows scaling (increase or reduction) of the bitmaps in memory, before displaying them on the screen of the device; frameToDraw is defined as a Rect variable (rectangle), specifying the rectangular region to be selected from the scaled bitmap (to be obtained from the images strip file), to be displayed on screen; said rectangular region is delimited by means of the (x,y) coordinates of its top-left point (in this example, (0,0)) and the (x,y) coordinates of its bottom-right point (in this example, (frameWidth,frameHeight)); in this particular example of initialization, Rect(0, 0,frameWidth,frameHeight), we are delimiting the rectangular region covered by the first frame within the scaled bitmap obtained from the images strip file to be drawn on the device screen; personXPos and personYPos are defined as float variables, and their purpose is to account for the x and y coordinates (in pixels) of the top-left point of the rectangular region in the device screen where the frame to be displayed will be placed; whereToDraw is defined as a RectF variable (rectangle delimited by float coordinates), and its purpose is to specify the rectangular region to be selected from the device screen to draw the frame we are dealing with; said rectangular region is delimited by means of the (x,y) coordinates of its top-left point (in this example, (personXPos, personYPos)) and the (x,y) coordinates of its bottom-right point (in this example, (personXPos+frameWidth, personYPos+frameHeight)); in this particular example of initialization, RectF(personXPos,personYPos, personXPos+frameWidth,personYPos+frameHeight), we are delimiting a rectangular region of dimensions equal to the frame to be displayed, where the top-left point is defined by (personXPos, personYPos), in this case (0,0), thus coinciding with the upper left corner of the device screen.

It is worth noting that although (personXPos, personYPos) coordinates are not changed in the pseudocode presented in FIG. 11A, 11B, some embodiments may change these values programmatically, thus making the frame displayed on the device screen change its position within the device screen (in other words, the rectangular region defined to hold the frame in the device screen is translated across the screen, since its defining coordinates have been changed by changing (personXPos, personYPos)); the effect of these changes would be the illusion of the person displayed in the frames moving across the screen of the device; this is different from moving (walking, running, etc.) in place, that is, moving in a fixed position in the device screen, as if the person was moving (walking/running, etc.) over a treadmill; some embodiments may choose to translate across the screen some other image bitmap displayed as a background over which the person in our frames is drawn, thus achieving the illusion that the person in our frames is moving across the background image bitmap, even if the person in our frames is moving (walking/running/etc.) in a rectangular region fixed in the device screen; in other words, the background image bitmap is translated across the device screen while the person in our frames moves in place (in a fixed position), thus giving the illusion that the person in our frames is translating across the scene displayed in the background image bitmap; other embodiments may use any variations and/or combinations of any said elements/changes/strategies and/or any other, including, by way of example without limitation, the translation and/or rotation and/or scaling of the person's image bitmap and/or the background's image bitmap and/or any other image bitmap to achieve any of the effects and/or illusion of animation of any kind (including navigation through virtual environments) and/or any other. Other embodiments may use any other variations and/or combinations of any of said elements/devices/specifications/characteristics/tools/variables/initializations/methods/approaches/techniques and/or any other tools/library/API, or any other in any fashion and for any purpose, including by way of example without limitation, achieving similar or different and/or variations and/or combinations of any effects described above.

Continuing with FIG. 11A, the method manageCurrentFrame( ) may be used to select the appropriate frame in the scaled bitmap of the images strip in order to achieve the illusion of animation (or control of the user's representation, or control of an attribute (e.g. cadence, stride length, velocity, activity, calories burned per time unit, etc.) of the user's representation) to the human eye; in simple words, the illusion of animation can be achieved by quickly displaying ordered and consecutive frames showing static postures of the user's representation; if the frames are displayed fast enough (e.g. frames updated with a frequency larger than approximately 12 Hz), they will look as a continuous and smooth transition to the human eye, achieving the effect of animation; in this example of embodiment, we first obtain the current time in milliseconds, and store it in a variable called time; next, if this is the first time accessing this method and we are starting the application (circumstance characterized by beginning_manageCurrentFrame being true, and currentFrame being 0), then we set the origin of time reference (frame_0_StartTime) equal to the previously obtained time, and we set beginning_manageCurrentFrame as false to avoid further changes; next, we obtain timeInto-CompleteAnimation as the difference between the previously determined time and frame_0_StartTime; next, we determine currentFrame as the integer value of (timeIntoCompleteAnimation*frameCount/completeAnimationPeriod) being applied the modulus operand (%) with frameCount (in order to obtain the rest of the division between (timeIntoCompleteAnimation*frameCount/completeAnimationPeriod) and frameCount); next, frameToDraw.left=currentFrame*frameWidth and frameToDraw.right=frameToDraw.left+frameWidth update the rectangular region borders within the scaled images strip to be drawn; in particular, the left border of said rectangular region is defined multiplying the currentFrame number by the frameWidth, while the right border of said rectangular region is defined as its left border plus frameWidth, the frame width; other embodiments may use any other approaches, and/or software, and/or libraries, and/or APIs, and/or variables, and/or methodologies, and/or any other and/or variations and/or combinations thereof to achieve the same or similar effects.

Continuing with FIG. 11B, the method doDraw(Canvas canvas) is mainly used to draw (render) on the device screen; first, the method manageCurrentFrame( ) is called to select the frame (rectangular region) within the scaled images strip to be drawn; next, canvas.drawBitmap performs the drawing or rendering on the device screen (canvas) of the specified rectangular region (frameToDraw) of the scaled images strip bitmap (imagesStrip), scaling/translating automatically to fill the destination rectangle (whereToDraw); it is worth noting that within this doDraw method, additional calls to canvas.drawBitmap can be performed to draw different images (e.g. background images, or images of other elements to be drawn within the device screen, etc. defined in analogous ways to how the imagesStrip bitmap is defined), which can be rendered in different positions (again, modifying the borders or coordinates of delimiting points of their defining rectangular (or other shape) regions), (and/or rendered with different rotations and/or scaling factors) within the device screen, as desired, thus achieving the effect or illusion of different types of movement across the device screen; it is also worth noting that some embodiments may leverage additional software methods implemented by the developer or provided by the device operating system to achieve any of the effects or any other in any fashion, including any variations and/or combinations thereof; by way of example without limitation, some embodiments may leverage Android operating system methods to perform rotations, scaling, translations or any other and/or variations and/or combinations thereof to achieve any effect in any fashion, for instance to achieve an illusion of movement/displacement of a person (e.g. a representation of the device's user) within a virtual environment displayed on the device screen; it is also worth noting that the doDraw method may be triggered (e.g. called within the main Thread) fast enough to achieve illusion of animation to the human eye (typically every 16 milliseconds, or a frequency of 60 Hz, although other frequencies may also be possible); some embodiments may use any variations and/or combinations of any terms/elements/procedures or any other in any fashion.

Continuing with FIG. 11B, the method setAnimationImagesStrip(int stripResource) is mainly used to select the images strip file (e.g. extension png) from which its frames are to be drawn on the device screen; the input parameter of this method, stripResource, is an integer to identify the images strip file we want to work with; for sake of simplicity, in this particular example of embodiment, we are assuming 3 images strip files ("firstImagesStripFile.png", "secondImagesStripFile.png", "thirdImagesStripFile.png") stored in the assets folder of the application, and stripResource will take values of 0, 1, and 2 to identify the first, second and third images strip files respectively; in this particular example, we may assume that said images strip files may correspond to FIG. 9A, FIG. 9B, and FIG. 9C respectively. Other embodiments may have a smaller or larger number of images strip files following any criteria including memory management, storage capabilities, design strategies, granularity in the changes of attributes of the representation, and/or any other including any variations and/or combinations thereof; by way of example without limitation, some embodiments may use 6 images strip files, corresponding to FIG. 9A, FIG. 9B, FIG. 9C, FIG. 9D, FIG. 9E, and FIG. 9F or any variation of them; in one embodiment, FIG. 9E and FIG. 9F may have the same number of frames (e.g. 26) as FIG. 9A, FIG. 9B, FIG. 9C, and FIG. 9D for efficient memory management purposes (e.g. to avoid heap memory fragmentation); other embodiments may use a very large number of images strip files, each one of them with the person (or user's representation) whose gait cycle is being displayed presenting, by way of example without limitation, a different value for a gait (or any other type) attribute (or one or more attributes) we may be focusing on; for instance, we could have 21 (or any other number) images strip files of 26 frames each, and each images strip file would present the person performing the gait activity (walk/run/jog or any other type of activity) with a different value (or any characterizer) of attribute(s).

Focusing by way of example without limitation on stride length, it may range for example from 15 inches to 45 inches (these values in inches may correspond to an exemplary user, and to a natural scale representation of a user, but it is obvious that the images strip files show scaled representations of a user, and consequently the stride length values of the person being shown in these images strip files are scaled values of the previously referred ones (e.g. 15 inches to 45 inches could accordingly be scaled down to 15 millimeters to 45 millimeters, or any other values following any criteria including by way of example without limitation, design)), with the first images strip file showing a stride length accordingly scaled to represent a real user's stride length of 15 inches, the second images strip file presenting a stride length accordingly scaled to represent a real user's stride length of 16.5 inches, the third images strip file illustrating a stride length accordingly scaled to represent a real user's stride length of 18 inches, and so on; consequently, we can control (e.g. by selecting the appropriate images strip file (with the appropriate value of attribute) to be rendered on the screen) in real time the stride length of the representation of the device user being displayed on the device screen, and we can replicate the values of stride length of the user with the values of stride length of the representation (obviously accordingly scaled to fit within the device screen), with a granularity (in this example, 1.5 inches) equal to the range in the values of stride length (in this example, 30 inches=45 inches−15 inches) divided by the number of images strip files we have minus 1 (in this example, 20=21−1). By way of example without limitation, the user's representation's stride length (or one or more attributes) may be controlled by setting its value proportional to the value of the user's determined stride length. Analogously, an aspect of an application or process in the device may be controlled by setting its value proportional to the value of the user's determined stride length (e.g. the value of brightness of the screen (and/or any aspect of user interface, settings, etc.) may be set proportionally to the value of the determined stride length), or by triggering/stopping/controlling in any way any procedure/process/application depending on the value of the determined stride length (e.g. if stride length is equal to 20 inches, then trigger (e.g. software activation) an out-loud reader), or in any other way. In some embodiments, the control over the stride length of the representation of the user can be performed with an update frequency larger than the user's step frequency, e.g. performing the selection of the appropriate images strip file (with the appropriate value of attribute (e.g. stride length)) to be rendered on the screen, with an update frequency larger the the user's step frequency; some embodiments may achieve this, for example, by calling the setAnimationImagesStrip method with the desired frequency and/or as soon as a new images strip file is needed; for this, some embodiments may call the setAnimationImagesStrip method from within the manageCurrentFrame method (e.g. called from within the doDraw method, which may be typically triggered with a frequency of 60 Hz); other embodiments may choose to call the setAnimationImagesStrip method from outside the manageCurrentFrame method, but within the onSensorChanged method (e.g. may be triggered with a frequency equal to the accelerometer sampling rate, which may be larger than the user's step frequency); other options are also possible; additional details are provided throughout the rest of this application.

It is also interesting to note that the setAnimationImagesStrip method presented in FIG. 11B may be modified in some embodiments: for example, the application may create and hold in memory the Bitmaps for each one of the images strip files stored in the assets folder (keeping for example several Bitmap variables, named e.g. imagesStrip1, imagesStrip2, imagesStrip3, etc.) and work directly with these Bitmaps rather than working with a single Bitmap and recycling it and assigning it the information of a new images strip file every time a new images strip file is needed; other embodiments may use any other strategies and/or any variations and/or combinations thereof.

It is worth noting that stripResource (e.g. in FIG. 11B) can be easily set programmatically, by way of example without limitation, using "if else" structures leveraging the value of, for example, the determined stride length (e.g. if the determined stride length is equal to (or less than) 15 inches, then stripResource is equal to 0; else, if the determined stride length is equal to (or less than) 16.5 inches, then stripResource is equal to 1; else, if the determined stride length is equal to (or less than) 18 inches, then stripResource is equal to 2; and so on); other embodiments may use alternative approaches, and leverage additional variables to programmatically set the value of stripResource; by way of example without limitation, some embodiments which determine in real time the device user's gait cadence (or frequency), together with the device user's gait velocity, together with the device user's gait activity, may programmatically set (with update frequency which can be chosen to be as the frequency of determination of cadence, velocity and activity, e.g., it may be larger than the user's step frequency) the value of stripResource using "if else" structures, leveraging as variables: the current value of stripResource (to be changed to a new value of stripResource), the newly determined user's gait cadence (or frequency), the newly determined user's gait velocity, the previously determined user's gait activity (associated to the current value of stripResource, which can be different from the new to be determined value of stripResource), and the newly determined user's gait activity. By way of example without limitation, if stripResource is equal to 0 (associated to e.g. activity "walking"), then, if the newly determined activity is "walking", and the newly determined velocity and the newly determined cadence (or frequency) have values that establish a newly determined stride length of 16.5 inches (e.g. velocity divided by cadence (after appropriate unit conversions, if needed), is equal to 16.5 inches), then stripResource is set equal to 1, and the value of activity is set to "walking". Or, if stripResource is equal to 10 (associated to e.g. activity "walking"), then, if the newly determined activity is "running", and the newly determined velocity and the newly determined cadence (or frequency) have values that establish a newly determined stride length of 45 inches (e.g. velocity divided by cadence (after appropriate unit conversions, if needed), is equal to 45 inches), then stripResource is set equal to 20, and the value of activity is set to "running". It is worth noting that some embodiments may use ranges or intervals for the decisions, and/or adjust the granularity of the decisions, and/or set assumptions or additional conditions that need to be satisfied in order to allow a change in stripResource; for example, some embodiments may choose to keep the same value of stripResource for some predefined ranges in the values of velocity and cadence (and thus some ranges in the value of stride length) given a previously determined activity (e.g. to prevent hysteresis cycles), or even prevent changes for some threshold of time if the newly determined values involve some drastic change (e.g. sudden change from "running" with stride length of 45 inches to "walking" with stride length of 15 inches).

It is also worth noting that, following any criteria referenced above, or any other, some embodiments may call the setAnimationImagesStrip method within the manageCurrentFrame method (which is called within the doDraw method), achieving an update frequency of the images strip file being displayed equal to the screen refresh rate (typically 60 Hz); some embodiments may also use alternative strategies (e.g. use of timers to delay operations, or use of conditionals to call setAnimationImagesStrip only after doDraw has been called for a number of times, or call setAnimationImagesStrip outside manageCurrentFrame (but within onSensorChanged method, which is triggered every time the sensor (e.g. accelerometer) delivers a new measurement, thus achieving an update frequency for setAnimationImagesStrip equal to the accelerometer sampling frequency) or any other strategies and/or variations and/or combinations thereof), in order to change or set the update frequency with which the setAnimationImagesStrip method is called; consequently, some embodiments may choose to set an update frequency for setAnimationImagesStrip higher (or lower) than the user's step frequency, thus controlling the stride length (e.g. some embodiments may use images strip files with a different stride length each, so every time we call setAnimationImagesStrip with a new value of stripResource, the user's representation displayed on the device screen is changing its stride length, and we may control this process leveraging the determined user's stride length (e.g. user's velocity divided by user's cadence)) of the representation of the user being displayed on the device screen with an update frequency higher (or lower) than the user's step frequency. It is also worth noting that in some embodiments, the referred controlling may apply to any other attribute (including by way of example without limitation, any angles (with respect to any direction (e.g. vertical, horizontal, etc.)) or any colors or any texture or any kind of displacements due to movement or any other characteristic of any part of the body (e.g. knees, arms, trunk, hips, shoulders, feet, neck, head, hands, fingers, etc.), or any characteristic of the gait (e.g. velocity, cadence, stride length, calories burned per time unit, activity, or any other)) or any other attributes (including by way of example without limitation, any number of them, e.g. any from 0 to a plurality) of the representation of the user on the device screen; analogously to the way the controlling of the stride length of the representation of the user can be achieved in some embodiments with an update frequency larger (or lower in other embodiments) than the user's step frequency, simply by selecting the appropriate frame of the appropriate images strip file with the appropriate stride length to be displayed on the device screen with the appropriate update frequency, other embodiments may perform the controlling of any other (or others, including e.g. any number of) attribute(s) (including without limitation, any of those mentioned above) of the representation of the user with an update frequency larger (or lower in other embodiments) than the user's step frequency, simply by selecting the appropriate frame of the appropriate images strip file with the appropriate attribute (or attributes) to be displayed on the device screen with the appropriate update frequency. Other embodiments may use any variations and/or any other approaches/methodologies/variables and/or any additional ones and/or combinations thereof.

It is also worth noting that a single one of the user's determined attributes (e.g. stride length), may control one or more attributes of the user's representation being displayed on the device screen; for example, as described above, the user's determined stride length may control the stride length of the user's representation being displayed on the device screen; this may be achieved in some embodiments by controlling, leveraging the value of determined user's stride length, the selection of an appropriate images strip file where the user's representation has the appropriate value of stride length (e.g. in pseudocode: if (determined_stride_length==value1) {then, images_strip_file="file1.png";} else if (determined_stride_length==value2) {then, images_strip_file="file2.png";} . . . and so on); in some embodiments, said user's representation may change other attributes besides stride length if we compare it with different images strip files; in other words, when we select the appropriate images strip file with the new value of stride length, other attributes in the user's representation may have also changed besides the stride length; for example, looking at FIG. 9A, 9B, 9C, 9D, (or FIG. 10A, 10B, 10C, 10D for more details) we see progressive enlargements in the stride length of the user's representation, but at the same time we also see changes in, by way of example without limitation: the swing of the arms, the vertical displacement of the hips (and the whole upper body), the rotations of the hips on the horizontal plane, the rotations of the shoulders on the horizontal plane, the rotations of the neck (and head) on the forward-backward direction, the angles of the thighs with the vertical direction, etc. Further details may also be appreciated in FIG. 10E, 10F, where, by way of example, the hair of the user's representation is changed (e.g. it bounces with every step), or the angle of the feet at landing on the ground is also changed. Other embodiments may choose to modify or control these and/or any other attributes in any way. Consequently, the determined stride length of the user may control the stride length of the user's representation being displayed on the device screen, and it may also control additional attributes of said representation (even if it is because of indirect reasons); as described in the rest of this application, said control may be performed in real time and with an update frequency larger than the user's step frequency, because for example in some embodiments said control is based on the same principles ruling the control of the user's representation's stride length with the user's stride length.

The same reasoning may be extended to any other attribute of the user, since in some embodiments, a user's determined gait attribute (e.g. cadence, activity, velocity, calories burned per time unit, etc.) may control one or more attributes of the user's representation being displayed on the device screen. By way of example without limitation, the user's representation's cadence (or one or more attributes) may be controlled by setting its value proportional to the value of the user's determined cadence. Analogously, an aspect of an application or process in the device may be controlled by setting its value proportional to the value of the user's determined cadence (e.g. the value of brightness of the screen (and/or any aspect of user interface, settings, etc.) may be set proportionally to the value of the determined cadence), or by triggering/stopping/controlling in any way any procedure/process/application depending on the value of the determined cadence (e.g. if cadence is equal to 2 Hz, then trigger (e.g. software activation) an out-loud reader), or in any other way. For example, as shown in FIG. 13 and FIG. 11A, the user's determined cadence may control the user's representation's cadence in real time and with an update frequency larger than the user's step frequency: the variable completeAnimationPeriod is controlled by the determined (in real time and with an update frequency larger than the user's step frequency) user's cadence, and it controls the value of the variable currentFrame, which is responsible for how fast a whole gait cycle of the user's representation is displayed, or how long it will take to display a whole user's representation's gait cycle (e.g. doDraw method in FIG. 11B is called with regular frequency of, for instance, 60 Hz, and this method calls the manageCurrentFrame method (FIG. 11A) to control which frame to be rendered on the device screen (currentFrame); as shown in FIG. 11A, if completeAnimationPeriod is large, it will take long time for the value of currentFrame to change, while if completeAnimationPeriod is short, it will take short time for the value of currentFrame to change; thus we are controlling the time it takes for currentFrame to change, or the time it takes for frames to change, or the time it takes for 26 frames to be changed, or the time it takes for a whole gait cycle to complete, or the time period of the gait, or the cadence or frequency (=1/period) of the gait of the user's representation on the device screen). At the same time that the user's determined cadence controls the user's representation's cadence, in the same conditions it may also control other attributes in the user's representation; for example, some embodiments may leverage the variable completeAnimationPeriod (controlled by the determined user's cadence) to control the selection of the images strip file whose frames are to be displayed on the screen; this can be easily achieved e.g. by using the variable completeAnimationPeriod within the setAnimationImagesStrip method in FIG. 11B, and including completeAnimationPeriod within the conditionals used to select the images strip file; for example: if (stripResource==0 && completeAnimationPeriod<1000) {myFilename="firstImagesStripFile_shortPeriod.png";} else if (stripResource==0 && completeAnimationPeriod>1000) {myFilename="firstImagesStripFile_longPeriod.png";} . . . and so on; other embodiments may use more complex conditionals and/or structures and/or any other methodologies/approaches/strategies and/or variations and/or combinations thereof. Consequently, the variable completeAnimationPeriod may control the images strip file to be displayed on the device screen in real time and with an update frequency larger than the user's step frequency; since we can modify/control one or more attributes of the user's representation in the images strip files (e.g. translations, scaling factors and rotation angles with respect to the vertical (and/or horizontal and/or forward-backward and/or any other) direction of thighs, shins, feet, hips, spine, chest, neck, head, shoulders, upper arms, forearms, hands, fingers, etc. and/or color, texture, material, etc. of any of the parts of the body or surfaces composing the user's representation, etc.), we can control one or more attributes of the user's representation in real time and with an update frequency larger than the user's step frequency, leveraging the determined user's cadence.

Analogous reasoning may be extended to any of the other determined user's gait parameters. By way of example without limitation, the determined user's activity, velocity, calories burned per time unit, and device position, may be leveraged analogously to the way the variable completeAnimationPeriod may be used to control one or more attributes of the user's representation in real time and with an update frequency larger than the user's step frequency, as described in application Ser. No. 16/044,833.

Continuing with FIG. 11B, within the setAnimationImagesStrip method, the first line: imagesStrip.recycle( ) is intended to free the memory resources being assigned to the currently used images strip file, because in this example of embodiment we want to assign those memory resources to hold a new different images strip file; it is worth noting that other embodiments may not need this step, but instead use additional memory allocations to handle different images strip files; this decision may depend on the available heap memory for the application, the size of the images strip files being handled, or any other criteria; other embodiments may employ any variations and/or any combinations and/or any other strategies, procedures, elements and/or any other. The next line: imagesStrip=null reiterates the previous line memory management aspect, trying to make sure that the memory allocated for the images strip file has been released; again, this step can be avoided in some embodiments following the plurality of criteria; it is also worth noting that in some embodiments working with early versions of Android operating system, in order to quickly free memory resources, the application developer might call the garbage collection procedure directly (System.gc( );); other embodiments may use any other procedures, variations and/or combinations thereof for efficient memory management. The next line: AssetManager assets=getResources( ).getAssets( ) is intended to declare the assets in the Android application in order to have easy access programmatically to the images strip files stored in the assets folder; it is worth noting that other embodiments may not store said files in the assets folder, so alternatives methods and/or procedures may be used; the next line: InputStream buffer is intended to declare an InputStream type variable, called buffer, destined to hold information from the images strip file we work with; again, some embodiments may use alternative methods and/or procedures and/or any other to read information from images strip files, so this and some of the next lines in this method may be substituted by different alternatives in some embodiments; the next line: String myFilename=" " declares a String type variable called myFilename, initialized empty, whose purpose is to hold the name of the images strip file we work with; in this particular example of embodiment we have 3 images strip files stored in the assets folder, whose names are: "firstImagesStripFile.png", "secondImagesStripFile.png", and "thirdImagesStripFile.png". The next 6 lines within the setAnimationImagesStrip method are "if else" structures intended to assign the appropriate images strip file name to the myFilename variable depending on the value of the stripResource variable; next, we create a try and catch block in order to safely (e.g. in terms of properly handling possible exceptions) perform the tasks stated within the try block: buffer=new BufferedInputStream(assets.open(myFilename)), which is intended to programmatically open the selected file from the assets folder and assign the information to the buffer variable, and imagesStrip=BitmapFactory.decodeStream(buffer), which is intended to decode the information held by the buffer variable and covert it into a Bitmap type variable, in this case, imagesStrip. The next line: imagesStrip=Bitmap.createScaledBitmap(imagesStrip, frameWidth*frameCount,frameHeight,true) is intended to process the information held by the imagesStrip variable, in order to create a scaled version of that Bitmap, where the new dimensions of the scaled Bitmap are specified by frameWidth*frameCount, and frameHeight, since the Bitmap will hold the information of the images strip file scaled to have a width equal to frameWidth multiplied by frameCount, and to have a height equal to frameHeight.

It is also worth noting that some embodiments may leverage the onSensorChanged method provided by the SensorEventListener interface (used for receiving notifications from the SensorManager when sensor values have changed); FIG. 13 shows schematic squeleton pseudocode for the onSensorChanged method for an example of embodiment, which would include this method within the AnimationThread class of FIG. 11A; multiple additions and/or variations and/or alternatives and/or combinations thereof are also possible in some embodiments. The "public void onSensorChanged(SensorEvent event)" method is called when sensor values have changed; detailed information on this and other topics can be found online at the android developer website or any other online sources (e.g. https://developer.android.com https://developer.android.com/reference/android/hardware/SensorListener.html); basically, to summarize in simple words, every time the accelerometer, if(event.sensor.getType( )==Sensor.TYPE_ACCELEROM-ETER), has new measurements, the onSensorChanged method is triggered and the new acceleration values can be read (e.g. double x_acceleration=event.values [0]; double y_acceleration=event.values[1]; double z_acceleration=event.values[2]); some embodiments may use the read acceleration values as inputs for a method that may determine the device user's gait velocity, calories burned per time unit, cadence, and activity (and/or any other gait (or any other type) attribute, such as stride length, and/or any other, and/or any variations and/or combinations thereof, including any number of them (e.g.: velocity, cadence, and activity; or velocity, cadence, activity, and stride length; etc.)) following any of the procedures/methodologies described in this specification or any other and/or any variations and/or combinations thereof; for example, the method determine_gait_parameters(double x_acceleration, double y_acceleration, double z_acceleration, double z_acceleration, double signal_vector_module_acceleration), may return an array of doubles containing the determined gait parameters: e.g. double[ ] gait_parameters=determine_gait_parameters(x_acceleration, y_acceleration, z_acceleration, signal_vector_module_acceleration); by way of example, the method determine_gait_parameters may be called directly from within the onSensorChanged method, thus determining the gait parameters with a frequency equal to the accelerometer sampling rate, which may be larger than the user's step frequency.

Some embodiments may determine (e.g. using the determine_gait_parameters method) only one of the device user's gait attributes (e.g. only velocity, or only cadence, or only activity, or only stride length, or only calories burned per time unit, or any other possibilities), while other embodiments may determine one or more (or any number) of the device user's gait (or any other type) attributes; again, it is worth noting that some embodiments may determine said attributes in real time simultaneously (or nearly simultaneously, e.g. one after the other, but with very small time differences, since some embodiments may determine them all with very high update frequencies (e.g. 60 Hz or higher)); other embodiments may use different approaches and/or variations and/or combinations thereof; for example, some embodiments may hold the read acceleration values in arrays that can be passed as inputs to the determine_gait_parameters method at desired time intervals, thus achieving a desired update frequency for the determination of the gait parameters; other embodiments may use upsampling/downsampling/filtering/or any other techniques to help in the setting of a desired update frequency for the determination of gait parameters; other embodiments may perform storing of acceleration values (e.g. creating a time window of acceleration values) within the determine_gait_parameters method and only trigger the actual determination of parameters when a desired amount of acceleration values (or a desired time interval in a time window) has been reached; other embodiments may use different approaches and/or variations and/or combinations thereof. Some embodiments may use the determine_gait_parameters method to determine any gait parameters or any others leveraging any possible methodology, including by way of example without limitation, the stride length (e.g. stride length equals the gait velocity divided by the gait cadence (or frequency)), the calories burned by the device user (for instance, the relationship between velocity and calories burned has been extensively studied (e.g. "Medicine and Science in Sports and Exercise", 2011, by Ainsworth B E, Haskell W L, Herrmann S D, Meckes N, Bassett Jr D R, Tudor-Locke C, Greer J L, Vezina J, Whitt-Glover M C, Leon A S), and said relationship (e.g. Calories burned per second equal to the user Weight (in Kg) multiplied by MET/3600, where MET is well known (e.g. MET for walking equals 1 plus velocity in mph times 0.7663 if velocity lower than 3.5, or −6.69 plus velocity in mph times 2.642 otherwise)) may be leveraged in some embodiments in order to determine the calories per time unit burned by a mobile device user), or any other (e.g. calories burned by the user equal the calories burned per time unit multiplied by the time under consideration (e.g. time unit=second)). Some embodiments may leverage the determine_gait_parameters method to compute only a few of said gait parameters (e.g. only velocity, cadence and activity), and compute additional parameters (e.g. stride length, calories burned, etc.) in additional methods (or in any other place within the application) leveraging the determined velocity, cadence and activity, in a way that all parameters are determined in real time with an update frequency larger than the user's step frequency; other embodiments may leverage the determine_gait_parameters method to compute all desired parameters (e.g. velocity, calories burned per time unit, cadence, activity and stride length, and any others) directly, also in real time with an update frequency larger than the user's step frequency; some embodiments may leverage any techniques/methodologies (e.g. upsampling, downsampling, filtering of any kind, use of specific time windows (with specific overlapping factors) to hold sensor values before the time window of those sensor values is being processed to determine parameters, and/or any other, and/or any variations and/or combinations thereof) to control the time intervals between determinations of parameters (or to control the determination update frequency), allowing determination in real time with an update frequency larger than the user's step frequency, or lower than the user's step frequency, or any other, following any criteria. Some embodiments may use any variations and/or combinations thereof.

Regarding the activity of the device user, some embodiments may determine it in real time within the determine_gait_parameters method, leveraging the acceleration values (or any sensor values), which may be processed over a desired time window or in any other way, together with other gait parameters already determined within said method (e.g. velocity, cadence, stride length, calories burned per time unit and/or any others, although some embodiments may not use all or any of these gait parameters), and/or any additional parameters computed making use of any of the previously referred inputs (e.g. mean and/or variance and/or standard deviation and/or skew and/or kurtosis and/or principal frequency component and/or energy in selected frequency bands, and/or any other obtained from acceleration (and/or any other sensor(s) values) signal vector module over a selected time window (e.g. 4 seconds time window), and/or from x,y,z components of acceleration (and/or any other sensor(s) values) over a selected time window (e.g. 4 seconds time window) or any other); in some embodiments all said parameters may be computed in real time within the determine_gait_parameters method, for example after determining the user's velocity, cadence, stride length and calories burned per time unit, and all (or some of them) may be leveraged as features to compute activity by means of a model (in some embodiments it may be a simple formula or a simple structure of conditionals or more complex structures or any other) generated (e.g. offline in a desktop PC, or directly within the device using appropriate software, or any other way and/or variations and/or combinations thereof) using machine learning or any other algorithms/methods and training data previously gathered from volunteers replicating/performing the range of activities (and/or any gait characteristics/attributes (e.g. velocity, cadence, stride length, calories burned per time unit, etc.) and/or any other such as the position of the device) we try to recognize using the device while their data on acceleration (and/or any other sensor(s) values), the type of activity (and/or values of gait attributes such as velocity, cadence, stride length, calories burned per time unit, device position, etc.) and any other parameters (including the features) are being recorded to create a training set; by way of example without limitation, any of the available software packages (e.g. MATLAB and Toolboxes, python and modules, weka, etc.) may be leveraged for modeling purposes (e.g. the model may be obtained leveraging the training set and using support vector machine, Naive Bayes, k-nearest neighbors, decision trees, random forests, logistic regression, linear regression or any other method/algorithm and/or any variations and/or combinations thereof, depending on criteria including without limitation: type and number of activities (and/or gait attributes and/or others) we try to recognize, accuracy, complexity, qualities of training set, and/or any other); an example of embodiment may use support vector machine to recognize between walking (e.g. coded with value 0) and running (e.g. coded with value 1), while other embodiments may use any alternative methods (and recognize any other activities, e.g. walking, jogging, jumping, cooking, household activities, running, cycling, driving, or any other), and some embodiments may leverage as features to determine activity and/or any gait attribute (e.g. velocity, stride length, cadence, calories burned per time unit, device position, and/or any other): 1) the user's velocity and the user's cadence, or 2) the user's velocity and the user's cadence and the mean, standard deviation, principal frequency component and energy in selected frequency bands of the acceleration (and/or any other sensor(s) values, and again, taken as x,y,z components and/or signal vector module) over a desired time window, or 3) the user's velocity and the user's cadence and the mean, variance, standard deviation, skew, kurtosis, principal frequency component and energy in selected frequency bands of the acceleration (and/or any other sensor(s) values, and again, taken as x,y,z components and/or signal vector module) over a desired time window, or 4) the mean, variance, standard deviation, skew, kurtosis, principal frequency component and energy in selected frequency bands of the acceleration (and/or any other sensor(s) values, and again, taken as x,y,z components and/or signal vector module) over a desired time window, or 5) any or all of the previous features and/or any other additional ones, and/or any variations and/or combinations thereof. In some embodiments any or all of said features may be determined in real time with an update frequency larger than the user's step frequency, and leveraging said features the user's activity (and/or any gait attribute (e.g. velocity, stride length, cadence, calories burned per time unit, device position, and/or any other)) may be determined in real time with an update frequency larger than the user's step frequency. In some embodiments, the determined user's activity may be used to control the activity of the user's representation on the device screen in real time with an update frequency larger than the user's step frequency: by way of example, by selecting an appropriate images strip file whose frames are to be displayed on the device screen (e.g., if activity is "walking" (e.g. coded as 1), then the images strip file may be any of FIG. 9A, 9B, 9C, 9D or any other representing a walking activity; or if the activity is "running" (e.g. coded as 2), then the images strip file may be any of FIG. 9E, 9F, or any other representing a running activity, etc.).

By way of example without limitation, some embodiments may employ the same (or similar) procedure described above for the determination of activity, to determine in real time and with an update frequency larger than the user's step frequency, the velocity (and/or cadence an/or calories burned per time unit and/or stride length and/or device position and/or any other attribute) of the user, as described in application Ser. No. 16/044,833.

It is interesting to note that the last block of 8 lines in FIG. 13 summarizes the way some embodiments may handle the change in the user's cadence through the variable completeAnimationPeriod, which may be used to select the appropriate frame from the appropriate images strip file to be displayed on the device screen to adequately control the cadence of the user's representation on the device screen (as shown for example in the manageCurrentFrame method defined in FIG. 11A); in other words, completeAnimationPeriod is programmatically changed (if needed, that is, if the newly determined value and the previous value are different, in which case the time reference value of frame_0_StartTime will also be accordingly updated) leveraging the newly determined value of cadence; as shown in FIG. 11A, the value of completeAnimationPeriod will control the value of the currentFrame variable; in other words, by changing the value of completeAnimationPeriod, we are controlling the frame to be displayed on the device screen (and thus, how fast a new frame is to be displayed: for example, if we keep the same value of currentFrame during many consecutive calls to the manageCurrentFrame method (typically called within the doDraw method at a specific frequency of, for instance, 60 Hz), then the transition between consecutive frames will be slow, thus giving the illusion of a low value of cadence; on the other hand, if we keep the same value of currentFrame during very few consecutive calls to the manageCurrentFrame method, the transition between consecutive frames will be fast, thus giving the illusion of a high value of cadence); in this example of embodiment, we may be updating completeAnimationPeriod every time cadence is determined (e.g. update frequency may be equal to accelerometer sampling rate, which may be e.g. 60 Hz); since the value of the currentFrame variable may typically be updated with a frequency of 60 Hz (every time manageCurrentFrame is called from the doDraw method), we have fine control over the value of currentFrame, because we can keep repeating the same value of currentFrame for longer periods of time when completeAnimationPeriod is large, but we will quickly transition to the next values of currentFrame when completeAnimationPeriod is short, thus achieving control over the cadence of the user's representation on the device screen. In simple words, when the user's cadence is large (completeAnimationPeriod is short), the values of currentFrame will change quickly (time difference between consecutive frames being displayed will be small, thus achieving high cadence of the representation displayed on the device screen); on the other hand, when the user's cadence is low (completeAnimationPeriod is long), the values of currentFrame will change slowly (time difference between consecutive frames being displayed will be large, thus achieving low cadence of the representation displayed on the device screen); consequently, the device user's determined cadence controls the user's representation cadence in real time, and with an update frequency that may be larger than the user's step frequency.

Again, some embodiments may use any variations and/or modifications and/or combinations of any said elements, concepts, procedures, methods, or any other additional ones, in any fashion. Definitions and/or further details for each one of the concepts, terms, etc. can be found online (e.g. https://developer.android.com or any other website).

Figure 12:
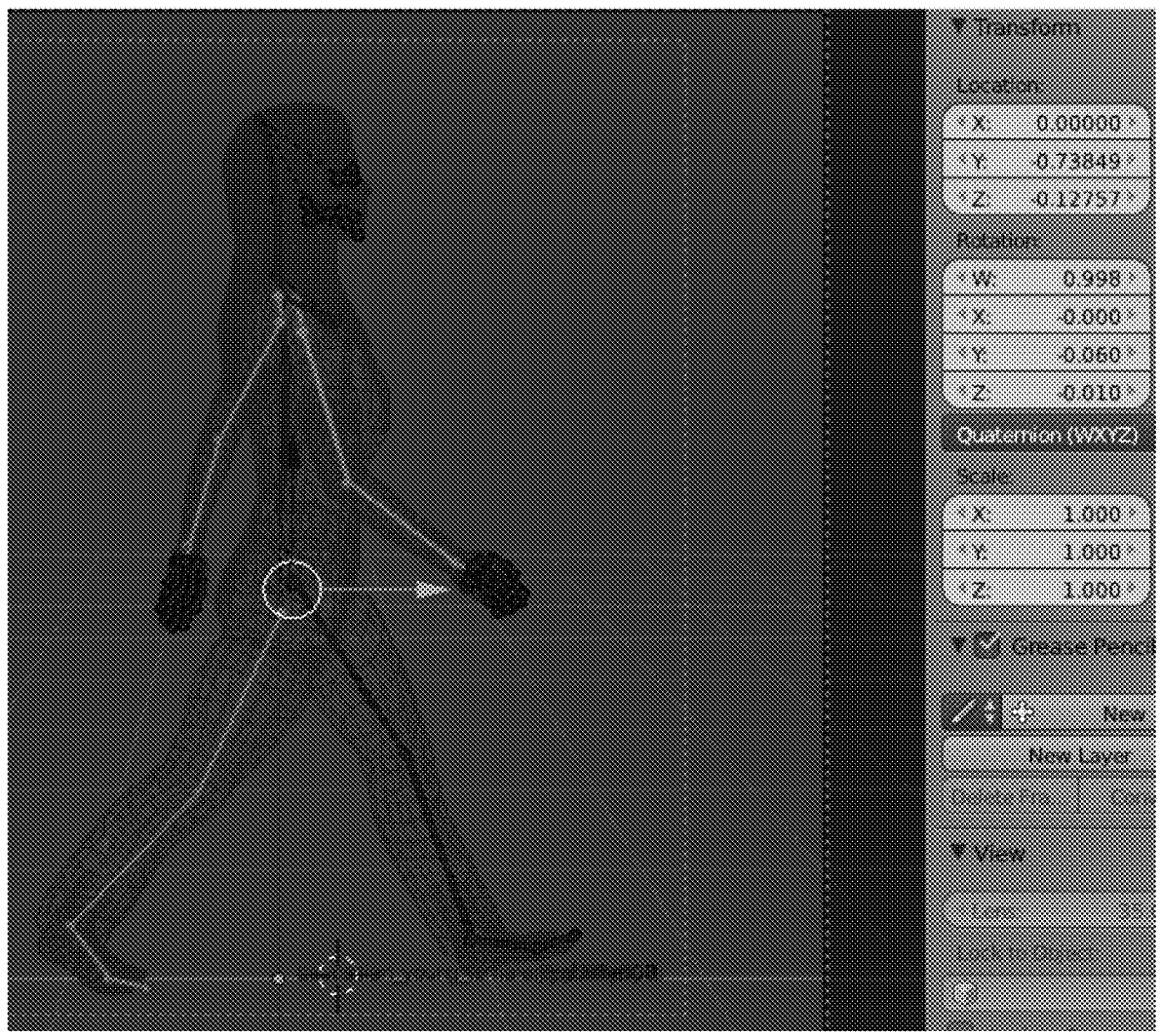
FIG. 12 illustrates part of the user interface of the open-source 3D computer graphics software Blender used in one embodiment.

FIG. 12 shows a screenshot of part of the Blender software's user interface that may be used in some embodiments. Blender is a professional, free and open-source 3D computer graphics software toolset used for creating animated films, visual effects, art, 3D printed models, interactive 3D applications and video games. Blender's features include 3D modeling, UV unwrapping, texturing, raster graphics editing, rigging and skinning, fluid and smoke simulation, particle simulation, soft body simulation, sculpting, animating, match moving, camera tracking, rendering, motion graphics, video editing and compositing. It also features an integrated game engine. In other embodiments, any other type of motion graphics and animation and/or 3D computer graphics and/or any other software (including by way of example without limitation, Autodesk, DAZ Studio, Shark 3D, MakeHuman, Unity) may be used (including in combination with Blender and/or any other) for any purposes, including the creation of a mesh (or set of joint surfaces) to form the 3D model leveraged to represent the mobile or wearable device user, and its integration with an skeleton (or set of joint bones) to control the movement of any part of the 3D model's body (e.g. see FIG. 12), and/or any other. In an example of embodiment, Blender may be used to create each one of the 26 frames composing the images strip files of FIG. 9A, 9B, 9C, etc. For instance, a 3D model (mesh structure and some bones used to control some of its features may be seen in FIG. 12, showing on the right side the x,y,z location, w,x,y,z quaternion rotation, x,y,z scale of an element selected from the 3D body on the left) may be leveraged and appropriately positioned in a scene to be rendered with the desired features, attributes, etc.; by way of example without limitation, each one of the elements (from the surfaces composing the mesh forming the model to each one of the bones controlling the attributes of different parts of the body) composing the 3D model, can be modified in different ways by the designer; for instance, the color, texture, materials (e.g. type of cloth), etc. of the surfaces composing the mesh forming the model can be controlled by the designer, or the location (3D coordinates x,y,z), rotation (quaternion w,x,y,z), scale (x,y,z) of the different parts of the body can be controlled by the designer, making use of, for instance, the bones and/or joints intended for controlling the body parts. For example, by appropriately choosing the location and rotation of the bones (and/or their edges and/or the joints) in the legs and feet, the stride length may be controlled; analogously, by appropriately choosing the location and rotation of the bones (and/or their edges and/or the joints) in the arms and hands, the swinging of the hands and arms may be controlled; the same applies to any other feature and/or attribute of the 3D model, which in some embodiments may have over 70 bones, each one for a particular part of the body, while other embodiments may have even larger number of bones to increase the level of control. By way of example without limitation, features and/or attributes in the 3D model that may be controlled by the designer in some embodiments may include: location, rotation and scale of any part of the body, color, texture, material, etc. of the different surfaces composing the mesh forming the model, stride length, swing of arms, bouncing of any soft parts of the body (e.g. hair bouncing with the movement), and/or any other and/or any variations and/or combinations thereof. By way of example without limitation, a particular embodiment may control the stride length, the locations and rotations of all the bones in the feet, legs, spine, hips, back, arms, hands, neck and head, the bouncing of the hair, the color and/or texture of the skin in order to control the appearance of sweat in skin and/or clothes and/or any other way to indicate any level of caloric consumption (e.g. calories burned per time unit, calories burned during a determined period of time, and/or any other) due to the exercise (e.g. gait activity). It is also worth noting that control of any attributes and/or features of the 3D model and/or any other object represented in the scene or control of the 3D model as a whole can be programmatically done (also in real time animations) by means of software (e.g. assigning the different values of x,y,z coordinates controlling the location of each body part (e.g. using their bones and/or their edges and/or the joints) to different variables in a software program, and/or assigning the different values of w,x,y,z quaternion controlling the rotation of each body part to different variables, and/or assigning the different values of x,y,z scaling factors controlling the size of each body part to different variables, etc.) to achieve the effect or illusion of animation and/or any other. In some embodiments, each one of the frames (e.g. static screenshots) constituting an animation may be rendered into pictures files (e.g. png extension files, or any other) using Blender, and said frames may be placed consecutively (e.g. ordered by sequence time) to obtain an images strip file such as FIG. 9A, 9B, 9C, 9D, 9E, 9F, and/or any other. For any of said purposes, any of the mentioned software packages and/or any other (e.g. Photoshop and/or any other raster graphics editor, and/or any of their plugins, etc.) may also be leveraged.

Some embodiments may leverage time domain windows to process the accelerometer (and/or any other sensor(s)) measurements, where the time length of said windows may be such (e.g. 2, 3, 4, 5, 6, 7, 8, 20, 40 seconds or any other length) that the amount of accelerometer (and/or any other sensor(s)) samples (e.g. having chosen a particular sampling frequency, or using upsampling/downsampling/filtering/thresholding and/or any other technique to process the read raw samples and obtain new processed samples at a fixed desired sampling rate) processed for the determination of the user's gait (or any other type) attribute(s) (e.g. velocity, cadence, stride length, calories burned per time unit, activity, device position and/or any other and/or any combinations thereof) is fixed at a particular value. By way of example without limitation, some embodiments may determine said attributes leveraging (processing) windows containing a fixed amount (e.g. called "amount_of samples") of sensor (e.g. accelerometer and/or any other type) samples, where the sensor samples may correspond e.g. to each one of the x,y,z components and/or the signal vector module (square root of summation of squared components) of the sensor. In an example of embodiment, said windows or groups of samples of fixed size (amount_of samples) may be created and held in the application leveraging the sensor measurements read from the sensor(s), and applying any technique if needed (e.g. upsampling/downsampling/filtering/thresholding and/or any other) to achieve the quantities desired, and using any required data structure (e.g. arrays, lists and/or any others and/or combinations thereof) to hold them for processing. For instance, if the sensor (e.g. accelerometer) sampling rate is fixed and constant at 46.5 Hz and we use time windows of 4 seconds, we may achieve a group (or groups (e.g. x,y,z components and/or signal vector module)) of 46.5 (samples/second)*4 (seconds)=186 samples; once we obtain the 186 samples, we can e.g. store them in an array (or arrays if we have several groups) that may be used as input for a method in the application (e.g. determine_gait_parameters in FIG. 13) in order to process them to determine the desired user's attribute(s). By way of example without limitation, we may achieve groups of 186 samples (e.g. using 4 seconds windows at 46.5 Hz sampling rate, or any other combinations of window length and sampling rate (e.g. 2 seconds at 93 Hz, 3 seconds at 62 Hz, etc.)) for each one of the x, y, z components of the accelerometer in the device, and store those values in arrays (e.g. array_x, array_y, array_z); next, we obtain another group of 186 samples for the signal vector module of the acceleration (square root of summation of squared x, y, z components), and store those 186 values in another array (e.g. array_svm); next we pass those 4 arrays (array_x, array_y, array_z, array_svm) as inputs parameters to the determine_gait_parameters method to process them in order to obtain the desired gait attributes.

We may also use any desired amount of overlapping to keep creating/holding/storing/processing groups of 186 samples at a desired frequency; for example, we may keep the newest 93 of the 186 samples (e.g. 50% overlapping) to create a new group (e.g. every 2 seconds), or we may discard the oldest 9 of the 186 samples (e.g. ~95% overlapping) to create a new group (e.g. every ~0.2 seconds), thus enabling the determination of the user's attribute(s) in real time and with an update frequency larger than the user's step frequency. Regarding the processing of said groups (or arrays) of 186 samples of sensor (e.g. accelerometer) data, some embodiments may leverage any of the techniques/approaches/methodologies/pre-processing/strategies/procedures, etc. described within this application and/or any others and/or any variations and/or combinations thereof to determine any or all of the desired gait attribute(s) (e.g. velocity, cadence, stride length, calories burned per time unit, activity, device position, etc.) and/or for any other purposes; by way of example without limitation, some embodiments may process any or all of said groups of 186 samples (and/or any other groups in any number) of accelerometer data leveraging wavelet transformation, selecting, for instance, as transformation parameters: a mother wavelet from any of Haar, or Daubechies, or Coiflets, or discrete version of Meyer, and a number of levels of decomposition sufficient to account for the frequency bands we expect. In a particular example, we may apply the wavelet transformation to said groups of 186 samples using Haar mother wavelet and eight levels of decomposition; in another example of embodiment, we may apply the wavelet transformation to said groups of 186 samples using Daubechies type 3 as mother wavelet and six levels of decomposition. Other embodiments may use any other values/numbers/qualities for any of the referred elements/quantities/variables and/or any other, including any variations and/or combinations thereof, and/or any other approaches/methodologies. Consequently, some embodiments may process groups of 186 samples of sensor data for the determination of the desired gait attributes, and some embodiments may process groups of 186 samples of sensor data using Daubechies type 3 as mother wavelet and six levels of decomposition.

Some embodiments may apply any of the mentioned approaches/strategies/methodologies, etc. for any other purposes, including the controlling of any attributes of any elements in FIG. 1C or FIG. 2B or any others. By way of example without limitation, other embodiments may use different numbers of image strip files, representing different or same type of activities, and each images strip file may contain different number of frames; any variations and/or combinations of any aspect and/or element and/or any additional elements and aspects are also possible. Multiple additions and/or variations and/or alternatives and/or combinations thereof are also possible in some embodiments. Other embodiments may use any other variations and/or combinations of any of said elements/devices/specifications/characteristics/tools/variables/initializations/methods/approaches/techniques and/or any other (hardware/software) tools/library/API, or any other in any fashion and for any purpose, including by way of example without limitation, achieving similar or different and/or variations and/or combinations of any effects described above.

Some embodiments may use any type of smartphones, mobile devices, wearable devices and/or sensors, or any other types of devices or combinations of them, including but not limited to, personal digital assistants, personal navigation systems, portable electronic devices, tablets, laptops, computers, and their peripheral devices. In some embodiments, the definition of mobile device may comprise any type of mobile phone, smartphone, wearable device and/or sensor, or any other types of device or wearable or combinations of them.

Some embodiments may use combinations of strategies and techniques, including, by way of example, and not limitation, machine learning techniques, probabilistic models, sensor fusion techniques, extraction of statistics, employment of filter banks, application of dimensionality reduction techniques, a variety of approaches for classification, etc. Details are omitted to improve the clarity of the description. In addition, some embodiments may use a variety of programming languages and methodologies in combination with varied hardware configurations and execution strategies.

Applications of some embodiments may comprise monitoring a variety of information of people in a variety of circumstances or contexts, including but not limited to, health-care, army, sports, etc., as described in application Ser. No. 16/044,833.

It is also worth noting that in some embodiments, the user's representation may be displayed/rendered/placed/projected on a place different from the device screen (e.g. it may be projected over a surface within or outside the device, or it may be rendered on a display/screen or any kind of projection/rendering electronics outside the device (e.g. a wall, other device, etc.)).

Threads are the cornerstone of any multitasking operating system and can be thought of as mini-processes running within a main process, the purpose of which is to enable at least the appearance of parallel execution paths within applications. By way of example without limitation, when an Android application is first started, the runtime system creates a single thread in which all application components will run by default. This thread is generally referred to as the main thread. The primary role of the main thread is to handle the user interface in terms of event handling and interaction with views in the user interface. Any additional components that are started within the application will, by default, also run on the main thread. Any component within an application that performs a time consuming task using the main thread may cause the entire application to appear to lock up until the task is completed; in some embodiments, this may be avoided simply by launching the task to be performed in a separate thread, allowing the main thread to continue unhindered with other tasks. In other words, some embodiments may avoid performing time-consuming operations (e.g. determining a user's gait characteristic, such as velocity and/or cadence and/or stride length and/or activity and/or calories burned per time unit and/or step count and/or device position and/or status of a medical condition and/or any other, and/or controlling an aspect of an application, such as inserting a new measurement of any of the referred user's gait characteristics or any others into a time chart representing the real time evolution of said gait characteristic, and/or selecting a frame (or a strip of images/frames) to be displayed based on the determined gait characteristic(s) and/or any other criteria and/or any other type of controlling and/or any variations and/or combinations thereof) on the main thread of an application. In order to create a new thread (e.g. a separate thread, or a thread separate from the main thread), the task or code to be executed in that thread needs to be placed within the run( ) method of a runnable instance. A new thread object then needs to be created, passing through a reference to the runnable instance to the constructor. Finally, the start( ) method of the thread object needs to be called to start the thread running. All these known concepts and others are further described in references such as: https://www.techotopia.com/index.php/A_Basic_Overview_of_Android_Threads_and_Threa d_handlers, https://developer.android.com, "Multithreaded Programming with Java Technology" by Bil Lewis, Prentice Hall, 2000, or "Taming Java Threads" by Allen Holub, Apress, Jun. 1, 2000, or "Multithreading Programming Techniques" by S. Prasad, McGraw-Hill, 1996, or "The art of multiprocessor programming" by Herlihy, Maurice, and Nir Shavit. Morgan Kaufmann, 2011, all of which are hereby incorporated by reference in their entireties for all purposes. By way of example without limitation, the following lines:

```
Thread slowThread=new Thread(new Runnable( ) {
  @Override
  public void run( ) {
    while (!Thread.interrupted( )) {
      determine_gait_parameters ( );
    }
  }
});
slowThread.start( );
```

Schematically represent an example of structure of schematic pseudocode that could help the skilled reader to implement a thread to be used in some embodiments to perform the task of the method "determine_gait_parameters" within a new (separate) thread called "slowThread", which is started using "slowThread.start( )". In some embodiments, we may substitute the determine_gait_parameters method by the setAnimationImagesStrip method or any other responsible for a controlling task, so that instead of determining gait characteristic(s), we would be controlling an aspect of an application or one or more attributes of a user's representation with the determined gait characteristic(s). In some embodiments, by way of example without limitation, this type of structure (or any others as shown in the many examples included with the mentioned references, and/or any variation and/or any combinations thereof) could be used in any way as described in any of the mentioned references.

By way of example without limitation, some embodiments may use the application's main thread or a separate thread or multiple separate threads (different from the main thread of the application) to launch tasks such as: determining any number of the user's gait characteristics such as velocity, cadence, step length, step count, calories burned per time unit, activity, device position, status of a medical condition, and/or any other of any type; for instance, said determining can be performed leveraging the determine_gait_parameters method of FIG. 13; consequently the determine_gait_parameters method would be called in some embodiments from within a separate thread (please remember, a separate thread is a thread different from the main thread). Some embodiments may use any other elements and/or methods and/or techniques and/or attributes and/or characteristics and/or any others and/or any variations and/or combinations thereof. In some embodiments, tasks for the determining of the user's gait characteristic(s) can be performed at a selected update frequency which can be different from the accelerometer sampling rate; for example, some embodiments may wait for a selected amount of time (e.g. wait(amount_of_time)) before the determining task is launched, or some embodiments may skip a selected number of accelerometer samples to perform the determination of the gait characteristic(s) with an update frequency lower than the accelerometer sampling rate (e.g. if every other accelerometer sample is skipped, we can determine the gait characteristic using every non-skipped accelerometer sample, thus achieving an update frequency for the determination equal to half the accelerometer sampling rate), or some embodiments may use any other techniques and/or methodologies (e.g. any filtering, upsampling, downsampling, and/or any other technique) and/or any variations and/or combinations thereof. Next, a series of examples of embodiments will be presented describing the update frequency of the determining of the user's gait characteristic(s); it is interesting to note that, in some cases, by way of example without limitation, said embodiments may be applicable regardless of the thread (e.g. main thread or a separate thread(s)) from which the determining task is launched; in other words, in some embodiments, the following examples may be applied when the task of determining the user's gait characteristic is launched from the main thread or when the task of determining the user's gait characteristic is launched from a separate thread. It is interesting to note that throughout this whole specification, when we refer to gait characteristic or gait characteristics, we may refer to any or all of velocity and/or cadence and/or stride length and/or activity and/or calories burned per time unit and/or device position and/or status of a medical condition of the user and/or step count and/or any other and/or any variations and/or combinations thereof.

As used herein, the term "frequency band of a gait activity" refers to the range of frequencies spanned by typical cadences of average users performing said gait activity. For example, in some embodiments, a frequency band of the gait activity of the user may span the range of frequencies at which average users typically perform the activity; by way of example without limitation, if the gait activity is walking, the range of frequencies for typical users may span in some embodiments from e.g. 0.25 Hz to 2.3 Hz, while in other embodiments it may span from e.g. 0.3 Hz to 2.35 Hz, depending on a variety of criteria (e.g. age of the users, health status of the users, height and weight of the users, etc.); in some embodiments the range of frequencies can be determined through tests/experiments with the users; by way of example without limitation, the scientific report "The role of stride frequency for walk-to-run transition in humans" by E. A. Hansen et. al, available online at https://www.nature.com/articles/s41598-017-01972-1 states that a calculated walk-to-run transition stride frequency may be approximately 70.6 strides/minute, which is approximately a step frequency of 2.35 Hz; some embodiments may choose a higher upper limit (e.g. 2.5 Hz or 3 Hz) as a precaution to make sure that the step frequency still corresponds to walking; consequently some embodiments may select a walking frequency band of e.g. 0.25 Hz to 3 Hz; similar reasoning may be applied to other types of gait activity, such as running, where some embodiments may select a running frequency band of e.g. 2.35 Hz to 7 Hz, while other embodiments may chose different values (e.g. as a precaution to make sure that the step frequency still corresponds to running, some embodiments may select a running frequency band of e.g. 2.5 Hz to 8 Hz); other embodiments may obtain the frequency band of the gait activity of a user or of a group of users through experimentation, and adapt the edges accordingly; other embodiments may use any variations and/or combinations thereof.

Some embodiments may set the update frequency of the determining of the gait characteristic as a constant value regardless of the sampling frequency of the device accelerometer, which may be variable/dynamic (e.g. it may not maintain a perfectly constant sampling rate over time, due to any reason such as hardware configuration, and/or computation burden in the device, and/or software configuration, and/or any other and/or any combinations thereof) or set dynamically in some embodiments (e.g. some embodiments may change the sampling rate depending on the user's activity; e.g. if the user is running, the sampling rate may be set higher than if the user is still), while it may be constant in other embodiments; by way of example without limitation, determining the gait characteristic leveraging the device accelerometer samples can be performed at a constant frequency; for example, we may set a fixed time interval (period of the determining, which is the inverse of the frequency of the determining) for determining the gait characteristic, and the accelerometer samples leveraged for the determining may be, for example, those contained in a window of a selected length of time (e.g. 10 seconds, or 20 seconds, or any other) up until the actual time instant of the determining; in some embodiments we may use any type of filtering and/or upsampling and/or downsampling and/or any other techniques to obtain, from the actual accelerometer generated samples, a constant amount of samples (e.g. processed samples) at every period of the determining of the gait characteristic; for example, if the accelerometer is generating samples at 60 Hz, and our period for determining the gait characteristic is 33 milliseconds (determining frequency=30 Hz; please know rounding may be used in some quantities for clarity), and we want one new processed sample at every determining period, we may skip every other accelerometer sample, and determine the gait characteristic at a constant update frequency of 30 Hz; for example, if the accelerometer is generating samples at 15 Hz, and our period for determining the gait characteristic is 33 milliseconds (determining frequency=30 Hz), and we want one new processed sample at every determining period, we may repeat every accelerometer sample, and determine the gait characteristic at a constant update frequency of 30 Hz; some embodiments may use any other techniques, such as any type of filtering and/or upsampling and/or downsampling and/or interpolation and/or averaging and/or any variations and/or combinations thereof. Consequently, in some embodiments we may set the update frequency of the determining of the gait characteristic as a constant value (e.g. 30 Hz or 60 Hz or 120 Hz or 14 Hz or any other value) while the sampling frequency of the device accelerometer is variable or is set dynamically (e.g. from 60 Hz to 15 Hz or any other values); in some embodiments the accelerometer sampling rate may be set dynamically depending on the determined user's activity (e.g. 60 Hz for running, 50 Hz for walking, 40 Hz for standing, and/or any other values and/or activities and/or choices and/or any variations and/or combinations thereof). Some embodiments may use any other values and/or techniques and/or elements and/or any variations and/or combinations thereof. Some embodiments may set the update frequency of the determining of the gait characteristic as a constant greater than the upper edge of the frequency band of the gait activity of the user (e.g. if the user's gait activity is walking, said update frequency may be set as e.g. 3.5 Hz, or 9 Hz, or 60 Hz, or 120 Hz, or any other value; if the user's gait activity is running, said update frequency may be set as e.g. 8.5 Hz, or 12 Hz, or 60 Hz, or 120 Hz, or any other value); in some embodiments, setting update frequencies above the upper edge of the frequency band of the gait activity of the user may be useful to be able to e.g. detect or account for details that may occur at high frequencies of said band. Similar reasoning may be extended in some embodiments to set the update frequency of the determining of the gait characteristic as a constant value (or variable value in other embodiments) greater than the upper edge of the frequency band of the gait activity of the user and lower than the device accelerometer sampling rate; by way of example without limitation, we may have an accelerometer sampling rate of 60 Hz, but we may set the update frequency of the determining of the gait characteristic as a constant value (or variable value in other embodiments) below that rate (e.g. constant at 30 Hz, or 20 Hz, or 10 Hz or any other value, and regardless of the user's activity; or variable at 30 Hz while the user is running, 20 Hz while the user is walking, and 10 Hz while the user is still) and greater than the upper edge of the frequency band of the gait activity of the user (e.g. 3 Hz if the user's gait activity is walking, or 8 Hz if the user's gait activity is running). In some embodiments we may set the update frequency of the determining of the gait characteristic as a constant value (or variable value in other embodiments) greater than the upper edge of the frequency band of the gait activity of the user and lower than the device accelerometer sampling rate, while the sampling frequency of the device accelerometer is variable or is set dynamically; for example, we may have an accelerometer sampling rate of 60 Hz, but we may set the update frequency of the determining of the gait characteristic as a constant (or variable in other embodiments) value (e.g. 20 Hz, or 10 Hz or any other value, following the example above) below the accelerometer sampling rate and greater than the upper edge of the frequency band of the gait activity of the user (e.g. greater than 3 Hz if the user's gait activity is walking, or greater than 8 Hz if the user's gait activity is running), and if the accelerometer sampling rate is varied (e.g. reduced to 25 Hz), we may keep the previously set update frequency of the determining of the gait characteristic constant (or variable in other embodiments) (e.g. 20 Hz, or 10 Hz, or any other value) and still below the accelerometer sampling rate and greater than the upper edge of the frequency band of the gait activity of the user (e.g. 3 Hz if the user's gait activity is walking, or 8 Hz if the user's gait activity is running).

It is interesting to note that in some embodiments we may try to minimize any computation burden on the main thread (or thread in charge of the user interface and/or aspects such as refreshing of screen (or frames)) of the application, so we may launch the task of determining the gait characteristic(s) from a separate thread with a selected update frequency, which in some embodiments may be different from the frame (or screen) refresh rate; by way of example without limitation, if the frame (or screen) refresh rate is 25 Hz, we may determine the gait characteristic(s) from a separate thread with an update frequency of e.g. 20 Hz or 60 Hz or 120 Hz (e.g. waiting for a specific amount of time to launch the determining task with the desired periodicity (e.g. waiting 50 milliseconds to launch determine_gait_parameters if we want an update frequency of 20 Hz), or using any of the methods mentioned in this specification or any others). In other embodiments we may still determine the gait characteristic(s) from the main thread but with an update frequency different from the frame (or screen) refresh rate; for example, if the frame (or screen) refresh rate is 25 Hz, we may launch the task of determining the gait characteristic(s) from within the main thread but with a specific periodicity, or specific update frequency, thus updating at e.g. 20 Hz or 60 Hz or 120 Hz (e.g. as explained before); by way of example without limitation, we may launch the task of determining the gait characteristic(s) from within the onSensorChanged method of FIG. 13 (e.g. with an update frequency equal to the accelerometer sampling rate (e.g. 60 Hz or 20 Hz or any other value), which may be different from the frame (or screen) refresh rate (e.g. 25 Hz)). Consequently, in some embodiments, the update frequency of the determining of the gait characteristic(s) may be different from the application's frame (or screen) refresh rate (e.g. lower or higher than the frame (or screen) refresh rate), and this may be achieved launching the task of determining the gait characteristic(s) from within the main thread of the application or from within a separate thread of the application, and all this may be achieved in some embodiments while 1) setting the update frequency of the determining of the gait characteristic as a constant value (or variable in other embodiments) while the sampling frequency of the device accelerometer is variable or is set dynamically, and/or 2) setting the update frequency of the determining of the gait characteristic as a constant (or variable in other embodiments) value greater than the upper edge of the frequency band of the gait activity of the user and lower than the device accelerometer sampling rate and/or 3) setting the update frequency of the determining of the gait characteristic as a constant (or variable in other embodiments) value greater than the upper edge of the frequency band of the gait activity of the user and lower than the device accelerometer sampling rate, while the sampling frequency of the device accelerometer is variable or is set dynamically. Some embodiments may use any other techniques and/or approaches and/or methodologies and/or any variations and/or combinations thereof, including any combinations with any of the possible values and/or variations and/or combinations of update frequency of any controlling with the gait characteristic(s).

By way of example without limitation, some embodiments may use the application's main thread or a separate thread or multiple separate threads (different from the main thread of the application) to launch tasks such as: controlling an aspect of an application and/or controlling one or more attributes of a user's representation (e.g. velocity and/or cadence and/or stride length and/or step count and/or calories burned per time unit and/or activity and/or device position and/or status of a medical condition, and/or any other of any type, such as the color of the skin and/or the bouncing of the hair and/or the rotation angles of the limbs and/or the movements of the head and/or the movements of the hands, etc of the user's representation, and/or any others and/or any variations and/or combinations thereof) with any or all of the determined user's gait characteristics (e.g. velocity and/or cadence and/or stride length and/or step count and/or calories burned per time unit and/or activity and/or device position and/or status of a medical condition, and/or any others and/or any variations and/or combinations thereof) by selecting the appropriate frame to be displayed and/or by selecting the appropriate strip of frames for displaying the user's representation; for instance, in some embodiments the selecting of the appropriate strip of frames may be performed leveraging the setAnimationImagesStrip method of FIG. 11B; consequently the setAnimationImagesStrip method may be called in some embodiments from within a separate thread (different from the main thread). Some embodiments may use any other elements and/or methods and/or techniques and/or attributes and/or characteristics and/or any others and/or any variations and/or combinations thereof.

In some embodiments, tasks for the controlling of an aspect of the application and/or for the controlling of one or more attributes of a user's representation with the determined user's gait characteristic(s) can be performed at a selected update frequency which can be different from the accelerometer sampling rate; for example, some embodiments may wait for a selected amount of time (e.g. wait (amount_of_time)) before the controlling task is launched, or some embodiments may skip a selected number of accelerometer samples before launching the controlling task, thus performing the controlling with an update frequency lower than the accelerometer sampling rate (e.g. if every other accelerometer sample is skipped before we launch the controlling task, we can perform the controlling with the determined gait characteristic every non-skipped accelerometer sample, thus achieving an update frequency for the controlling equal to half the accelerometer sampling rate), or some embodiments may use any other techniques and/or methodologies (e.g. any filtering, upsampling, downsampling, and/or any other technique) and/or any variations and/or combinations thereof. Next, a series of examples of embodiments will be presented describing the update frequency of the controlling of an aspect of the application and/or the controlling of one or more attributes of a user's representation with the determined user's gait characteristic(s); it is interesting to note that, in some cases, by way of example without limitation, said embodiments may be applicable regardless of the thread (e.g. main thread or a separate thread(s)) from which the controlling task is launched; in other words, in some embodiments, the following examples may be applied when the task of controlling is launched from the main thread or when the task of controlling is launched from a separate thread. It is interesting to note that throughout this whole specification, when we refer to gait characteristic or gait characteristics, we may refer to any or all of velocity and/or cadence and/or stride length and/or activity and/or calories burned per time unit and/or device position and/or status of a medical condition of the user and/or step count and/or any other and/or any variations and/or combinations thereof.

Some embodiments may set the update frequency of the controlling of an aspect of the application and/or controlling of one or more attributes of a user's representation with the determined user's gait characteristic(s) as a constant value (or variable value in other embodiments) regardless of the sampling frequency of the device accelerometer, which may be variable or set dynamically in some embodiments, while it may be constant in other embodiments; by way of example without limitation, controlling can be performed at a constant (or variable in other embodiments) frequency (e.g. constant at 8 Hz or 30 Hz or 60 Hz or 120 Hz; or variable by setting a frequency of e.g. 8 Hz while the user is still, 30 Hz while the user is walking, and 60 Hz while the user is running); for example, we may set a fixed time interval (period of the controlling, which is the inverse of the frequency of the controlling) for launching the task of controlling with the determined gait characteristic; for instance, some embodiments may wait for said fixed time interval (period of the controlling, which may be e.g. 50 milliseconds if the controlling update frequency is 20 Hz) to expire before launching the controlling task. In some embodiments we may set the controlling frequency in terms of the sampling frequency of the device accelerometer and launch the controlling task after a selected number of accelerometer samples have been generated, which would result in a controlling frequency equal or lower than the accelerometer sampling frequency (e.g. equal if we launch the controlling at every accelerometer sample, and lower (e.g. by half) if e.g. we launch the controlling at every other accelerometer sample); in other embodiments we may use any type of filtering and/or upsampling and/or downsampling and/or any other techniques to obtain, from the actual accelerometer generated samples, a constant amount of samples (e.g. processed samples) at every period of the controlling; for example, if the accelerometer is generating samples at 60 Hz, and our period for controlling is 33 milliseconds (controlling frequency=30 Hz), and we want one new processed sample at every controlling period, we may skip every other accelerometer sample, and perform the controlling at a constant update frequency of 30 Hz; for example, if the accelerometer is generating samples at 15 Hz, and our period for controlling is 33 milliseconds (controlling frequency=30 Hz), and we want one new processed sample at every controlling period, we may repeat every accelerometer sample, and perform the controlling at a constant update frequency of 30 Hz; some embodiments may use any other techniques, such as any type of filtering and/or upsampling and/or downsampling and/or interpolation and/or averaging and/or any variations and/or combinations thereof. Consequently, in some embodiments we may set the update frequency of the controlling of an aspect of the application and/or controlling of one or more attributes of a user's representation with the determined user's gait characteristic(s) as a constant value (e.g. 30 Hz or 60 Hz or 120 Hz or 14 Hz or any other value) while the sampling frequency of the device accelerometer is variable or is set dynamically (e.g. from 60 Hz to 15 Hz or any other values). Some embodiments may use any other values and/or techniques and/or elements and/or any variations and/or combinations thereof. Some embodiments may set the update frequency of the controlling with the gait characteristic as a constant (or variable in other embodiments) greater than the upper edge of the frequency band of the gait activity of the user (e.g. if the user's gait activity is walking, said update frequency may be set as a constant at e.g. 3.5 Hz, or 9 Hz, or 60 Hz, or 120 Hz, or any other value; if the user's gait activity is running, said update frequency may be set as a constant at e.g. 8.5 Hz, or 12 Hz, or 60 Hz, or 120 Hz, or any other value; in other embodiments choosing a variable value, we may set said update frequency as e.g. 10 Hz if the user is walking, and 20 Hz if the user is running). Similar reasoning may be extended in some embodiments to set the update frequency of the controlling of an aspect of the application and/or controlling of one or more attributes of a user's representation with the determined user's gait characteristic(s) as a constant (or variable in other embodiments) value greater than the upper edge of the frequency band of the gait activity of the user and lower than the device accelerometer sampling rate; by way of example without limitation, we may have an accelerometer sampling rate of 60 Hz, but we may set the update frequency of the controlling with the gait characteristic as a constant value below that rate (e.g. 30 Hz, or 20 Hz, or 10 Hz or any other value) and greater than the upper edge of the frequency band of the gait activity of the user (e.g. 3 Hz if the user's gait activity is walking, or 8 Hz if the user's gait activity is running); embodiments choosing a variable value may set said frequency e.g. at 10 Hz if the user is walking or 20 Hz if the user is running. In some embodiments we may set the update frequency of the controlling of an aspect of the application and/or controlling of one or more attributes of a user's representation with the determined user's gait characteristic(s) as a constant (or variable in other embodiments) value greater than the upper edge of the frequency band of the gait activity of the user and lower than the device accelerometer sampling rate, while the sampling frequency of the device accelerometer is variable or is set dynamically; for example, we may have an accelerometer sampling rate of 60 Hz, but we may set the update frequency of the controlling as a constant value (e.g. 20 Hz, or 10 Hz or any other value) below the accelerometer sampling rate and greater than the upper edge of the frequency band of the gait activity of the user (e.g. greater than 3 Hz if the user's gait activity is walking, or greater than 8 Hz if the user's gait activity is running), and if the accelerometer sampling rate is varied (e.g. reduced to 25 Hz), we may keep the previously set update frequency of the controlling constant (e.g. 20 Hz, or 10 Hz, or any other value) and still below the accelerometer sampling rate and greater than the upper edge of the frequency band of the gait activity of the user (e.g. 3 Hz if the user's gait activity is walking, or 8 Hz if the user's gait activity is running). Embodiments choosing a variable value for the controlling frequency may set it e.g. as 20 Hz while the user is running and 10 Hz while the user is walking, while the accelerometer sampling rate is either 60 Hz or 25 Hz.

It is interesting to note that in some embodiments we may try to minimize any computation burden on the main thread (or thread in charge of the user interface and/or aspects such as refreshing of frames (or screen)) of the application, so we may launch the task of controlling with the gait characteristic(s) from a separate thread with a selected update frequency, which in some embodiments may be different (e.g. lower or higher) from the frame (or screen) refresh rate; by way of example without limitation, if the frame (or screen) refresh rate is 25 Hz, we may perform the controlling with the gait characteristic(s) from a separate thread with an update frequency of e.g. 20 Hz or 60 Hz or 120 Hz (e.g. waiting for a specific amount of time to launch the controlling task with the desired periodicity (e.g. waiting 50 milliseconds to launch the setAnimationImagesStrip method (or any other method for controlling with the determined gait characteristic(s)) if we want an update frequency of 20 Hz), or using any of the methods mentioned in this specification or any others). In other embodiments we may still perform the controlling with the gait characteristic(s) from the main thread but with an update frequency different (e.g. lower or higher) from the frame (or screen) refresh rate; for example, if the frame (or screen) refresh rate is 25 Hz, we may launch the task of controlling with the gait characteristic(s) from within the main thread but with a specific periodicity, or specific update frequency, thus updating at e.g. 20 Hz or 60 Hz or 120 Hz (e.g. as explained before); please note that as used herein, the term "animation frame(s) update frequency" (how often a new frame is displayed) is a different concept/term from the term "screen (or frame(s)) refresh rate" (how often the screen is refreshed, regardless of the content on the screen, which in some embodiments may remain without being updated while it is being refreshed); for example, we may refresh at 60 Hz, but we may update the animation's frames at 30 Hz (thus a same animation frame will be refreshed before any update); in some embodiments both frequencies may be different (e.g. screen (or frame) refresh rate=60 Hz and animation frame update frequency=30 Hz), while in other embodiments they may have the same value (e.g. screen (or frame) refresh rate=60 Hz and animation frame update frequency=60 Hz); other embodiments may use any other values and/or variations and/or combinations thereof; by way of example without limitation, we may launch the task of controlling with the gait characteristic(s) from within the onSensorChanged method of FIG. 13 (e.g. with an update frequency equal to the accelerometer sampling rate (e.g. 60 Hz or 20 Hz or any other value), which may be different from the frame (or screen) refresh rate (e.g. 25 Hz)). Consequently, in some embodiments, the update frequency of the controlling of an aspect of the application and/or controlling of one or more attributes of a user's representation with the determined user's gait characteristic(s) may be different from the application's frame (or screen) refresh rate (e.g. lower or higher than the frame (or screen) refresh rate), and this may be achieved launching the task of controlling with the gait characteristic(s) from within the main thread of the application or from within a separate thread of the application, and all this may be achieved in some embodiments while 1) setting the update frequency of the controlling with the gait characteristic as a constant (or variable in other embodiments) value while the sampling frequency of the device accelerometer is variable or is set dynamically, and/or 2) setting the update frequency of the controlling with the gait characteristic as a constant (or variable in other embodiments) value greater than the upper edge of the frequency band of the gait activity of the user and lower than the device accelerometer sampling rate and/or 3) setting the update frequency of the controlling with the gait characteristic as a constant (or variable in other embodiments) value greater than the upper edge of the frequency band of the gait activity of the user and lower than the device accelerometer sampling rate, while the sampling frequency of the device accelerometer is variable or is set dynamically. Some embodiments may use any other techniques and/or approaches and/or methodologies and/or any variations and/or combinations thereof, including any combinations with any of the possible values and/or variations and/or combinations of update frequency of the determining of the gait characteristic(s); and in some embodiments, both the update frequency of the controlling and the update frequency of the determining may be equal.

It is interesting to note that in some embodiments, by way of example without limitation, a user's representation can be controlled in real time with a gait velocity (and/or cadence and/or activity and/or stride length and/or calories burned per time unit and/or device position and/or step count and/or status of a medical condition and/or any other and/or any variations and/or combinations thereof) of the user, which may be determined in real time; in some embodiments the user's representation can be displayed/shown/presented/represented/illustrated etc. within the user's mobile or wearable device (e.g. on a screen of the device), while in other embodiments the user's representation can be displayed/shown/presented/represented/illustrated etc. outside the user's mobile or wearable device (e.g. on a desktop computer screen, or on a laptop, or projected on a wall or any other surface) and any type of communication and/or connection and/or means and/or any other well known procedures and/or methodologies can be used to link the user and/or the user's device with any external device and/or element where the user's representation is displayed/shown/presented/represented/illustrated etc. For example, a user's representation such as any of those in FIG. 9A to 9F and/or FIG. 10A to 10F and/or FIG. 12 and/or any other Figures and/or any others and/or variations and/or any combinations thereof, can have its velocity controlled by the determined user's gait velocity, and its value can be shown e.g. on a dashboard element such as any of (120) and/or (130) of FIG. 1C, and/or (210) and/or (220) of FIG. 2B and/or any other.

It is interesting to note that throughout the whole of this specification (and any other cross references with which this application is linked), the term velocity or gait velocity may be replaced or substituted by any and/or all and/or any combinations of the following terms: gait cadence and/or activity and/or stride length and/or calories burned per time unit and/or device position and/or step count and/or status of a medical condition and/or any other; this is because describing particular examples using just one word (e.g. velocity) clarifies things to the reader, but all possible combinations should be considered (although we do not write them all to avoid confusing the reader); by way of example without limitation, when we describe controlling the user's representation's velocity with a determined gait velocity of the user, the reader should consider as well all the following possibilities: controlling the user's representation's cadence with a determined gait cadence of the user; controlling the user's representation's stride length with a determined gait stride length of the user; controlling the user's representation's activity with a determined gait activity of the user; controlling the user's representation's calories burned per time unit with determined calories burned per time unit of the user; controlling the user's representation's device position with a determined device position of the user; controlling the user's representation's step count with a determined step count of the user; controlling the user's representation's status of a medical condition with a determined status of a medical condition of the user. Again, any variations and/or combinations thereof should also be considered.

In some embodiments, one or more attributes of one or more elements of the user's representation are controlled with the determined gait velocity (or any other characteristic e.g. cadence, and/or stride length, and/or activity, and/or device position, and/or calories burned per time unit, and/or status of a medical condition, and/or step count, etc.) in real time. For example, a user's representation may be composed of one or more elements such as right foot and/or left foot and/or right leg and/or left leg and/or right arm and/or left arm and/or right hand and/or left hand and/or shoulders and/or spine bone and/or hip bone and/or neck bone and/or neck and/or head and/or head bone and/or hair and/or eyes and/or mouth and/or eye brows and/or face, etc. Additional examples of elements of a user's representation and more can be found e.g. in https://en.wikibooks.org/wiki/Blender_3D:_Noob_to_Pro, https://cgi.tutsplus.com/tutorials/building-a-complete-human-character-rig-in-maya--cg-14575, https://gamedevelopment.tutsplus.com/tutorials/animating-a-makehuman-character-in-blender-part-one--cms-26489, https://en.blender.org/index.php/Doc:2.6/Tutorials/Your_First_Animation/2.Animation and/or any references and/or links within, all of which are herein incorporated by reference for all purposes. Each one of the elements of a user's representation may have one or more attributes, such as color, texture, etc.; for example, the face may have a skin color (e.g. black or white or any other) which may vary with the determined user's gait velocity/cadence/stride-length/calories per time unit/activity/device position/status of medical condition/etc. (e.g. if the determined velocity/cadence/stride-length/calories per time unit/ activity/device position/status of medical condition/etc. is above 4 mph/2.2 Hz/0.85 m/250 Cal per hour/walking activity/pocket position/healthy/etc., the skin color of the face may be set to a reddish color to reflect exhaustion, or if the determined velocity/cadence/stride-length/calories per time unit/activity/device position/status of medical condition/etc. is below 1 mph/0.8 Hz/0.4 m/120 Cal per hour/ walking activity/pocket position/unhealthy/etc. the skin color of the face may be set to a pale color to reflect weakness in the motion); well-known software packages such as Blender easily enable the setting of colors and/or textures and/or position and/or rotation and/or scaling and/or any other property of any element of a user's representation; by way of example without limitation, analogously to the way the skin color of the face was controlled in the example above, we can control the transform related attributes of e.g. the hip bone (or any other element) of the user's representation as e.g. shown in FIG. 12, and set/control them with or accordingly with the determined velocity and/or cadence and/or stride-length and/or activity and/or device position and/or calories burned per time unit and/or status of a medical condition and/or step count and/or any other and/or any variations and/or combinations thereof; for example, if the determined velocity/cadence/stride-length/calories per time unit/activity/device position/status of medical condition/etc. is/are above 4 mph/2.2 Hz/0.85 m/250 Cal per hour/walking activity/pocket position/healthy/etc. we can control the transform related attributes of the user's representation's hip (or of any movable part of the user's representation, e.g. right foot, left hand, head, etc.) by setting their values accordingly (e.g. changing said transform related attributes from one frame to the next as follows: e.g. from: Location x, y, z: 0.00000, −0.73849, −0.12757, Rotation (Quaternion w, x, y, z): 0.998, −0.000, −0.060, −0.010, Scale x, y, z: 1.000, 1.000, 1.000, to: Location x, y, z: 0.00000, −0.50799, −0.08775, Rotation (Quaternion w, x, y, z): 0.999, −0.000, −0.036, −0.006, Scale x, y, z: 1.000, 1.000, 1.000); and if the determined velocity/cadence/stride-length/calories per time unit/activity/device position/status of medical condition/etc. is/are below 1 mph/0.8 Hz/0.4 m/120 Cal per hour/walking activity/pocket position/unhealthy/etc. we can control the transform related attributes of the user's representation's hip (or of any movable part of the user's representation, e.g. right foot, left hand, head, etc.) by setting their values accordingly (e.g. changing said transform related attributes from one frame to the next as follows: e.g. from: Location x, y, z: 0.00000, −0.73849, −0.12757, Rotation (Quaternion w, x, y, z): 0.998, −0.000, −0.060, −0.010, Scale x, y, z: 1.000, 1.000, 1.000, to: Location x, y, z: 0.00000, −0.69140, −0.11943, Rotation (Quaternion w, x, y, z): 0.999, −0.000, −0.048, −0.008, Scale x, y, z: 1.000, 1.000, 1.000); other embodiments may use any other values and/or approaches and/or configurations and/or methods and/or any other and/or any variations and/or combinations thereof; further information can be found in "The Complete Guide to Blender Graphics, Second Edition: Computer Modeling and Animation" 2012 by John M. Blain, and/or in https:// www.blender.org/support/tutorials/ all of which are herein incorporated by reference for all purposes. Additional examples of one or more attributes of elements of the user's representation which can be controlled with the determined user's gait velocity/cadence/stride-length/etc include: the texture of the skin of the neck, which can be modified to reflect sweat when the determined gait characteristics (again, velocity and/or cadence and/or stride-length and/or any other) indicate levels of high intensity in the gait activity.

In some embodiments, one or more attributes (e.g. color and/or texture) of three or more elements of the user's representation (e.g. right foot, left foot, right leg) may be controlled with the determined gait velocity in real time and independently; again, please consider that any other gait characteristic (e.g. cadence and/or stride length and/or activity and/or calories per time unit and/or device position and/or status of a medical condition and/or steps count and/or any other) can substitute the term velocity in these descriptions; for example, if the determined gait velocity is 4 mph, the right foot may be assigned a purple color, the left foot may be assigned a red color and the right leg may be assigned a texture showing sweat; if the determined gait velocity is 3 mph, the right foot may be assigned a red color, the left foot may be assigned an orange color and the right leg may be assigned a texture showing less sweat; if the determined gait velocity is 2 mph, the right foot may be assigned an orange color, the left foot may be assigned a yellow color and the right leg may be assigned a texture showing very little sweat; if the determined gait velocity is 1 mph, the right foot may be assigned a yellow color, the left foot may be assigned a white color and the right leg may be assigned a texture showing no sweat. It is interesting to note that in some embodiments, the controlled one or more attributes of said elements of the user's representation comprise one or more attributes different from properties of a transformation (change of location and/or rotation and/or scaling) affecting the whole user's representation equally; for example, the controlled attributes of the elements could be color, and/or texture, but not location and/or rotation and/or scaling coordinates/attributes when said location and/ or rotation and/or scaling attributes are being modified only by a transformation that affects all the representation's elements equally (e.g. when we control the location and/or rotation and/or scaling coordinates/attributes (or any other(s) (e.g. velocity) derived from transform related attributes) of a user's representation as a whole, or of the user's representation's center of mass); for example, the control of the velocity of the user's representation as a whole (or the control of the velocity of the user's representation's center of mass) with the determined user's velocity does not satisfy the condition that one or more attributes of three or more elements of the user's representation are controlled independently. In some embodiments, one or more attributes of three or more elements of the user's representation are controlled with, and vary as a function of, the determined gait velocity (and/or cadence, and/or stride length and/or calories burned per time unit, and/or device position, and/or activity, and/or status of a medical condition, and/or balance, and/or steps, etc.) in real time and independently. By way of example without limitation, if we consider the right foot as an element, and the maximum displacement in the horizontal direction of said right foot as an attribute (e.g. said attribute may indicate the maximum advancement or maximum displacement of the right foot in the horizontal direction at every footstep), said attribute may vary in real time as a function of the determined gait velocity (e.g. maximum displacement may be proportional to 10 times the determined velocity, or vary with any other function in terms of the determined velocity); and in some embodiments, this variation may be different and/or independent for attributes of different elements of the user's representation (e.g. the maximum displacement in the horizontal direction in the left foot may vary with velocity differently than in the right foot (e.g. maximum displacement of the left foot may be proportional to 11 times the determined velocity); and the maximum displacement of the left hand may be proportional to 7 times the determined velocity. In some embodiments, the described variation of said attribute(s) may occur while the user performs a same type of activity. For example, the maximum displacement of the right foot may vary proportionally with the determined velocity while the user performs a walking activity (e.g. maximum displacement in centimeters=velocity in mph*10); or the color of the right foot may be assigned different values for each one of at least four different values of the determined velocity while the user performs a walking activity (e.g. said color is set as purple, red, orange, and yellow when the determined user's walking velocity is, respectively, 4 mph, 3 mph, 2 mph and 1 mph); or the color of the right foot may be assigned different values for each one of at least four different values of the determined velocity while the user performs a running activity (e.g. said color is set as black, blue, magenta, and pink when the determined user's running velocity is, respectively, 8 mph, 7 mph, 6 mph and 5 mph).

In some embodiments, the user's representation shows feet landing on (or touching) a ground (or a horizontal plane that in some embodiments may represent any type of ground, including an invisible ground in some examples of virtual environments) in synchronism with the user's feet landing on (or touching) a ground (or stepping), and this may happen in some embodiments while the user's representation (or one or more attributes (or one or more attributes of one or more elements) of the user's representation) is/are being controlled in real time with the determined user's gait velocity and/or cadence and/or stride-length and/or activity, and/or calories burned per time unit, and/or device position, and/or status of a medical condition, and/or balance, and/or steps, etc. An example of embodiment describing a user's representation showing feet landing on (or touching) a ground (or stepping) in synchronism with the user's feet landing on (or touching) a ground (or stepping) can be found at least in application U.S. 62/750,292 entitled "Gait analysis applied for control", by David Martin, filed on Oct. 25, 2018, herein incorporated by reference for all purposes. For example, some embodiments may detect the time instants at which the mobile or wearable device user's feet land on the ground through the analysis of a motion sensor (e.g. embedded within the mobile or wearable device) signal (e.g. detecting peaks of maximum amplitude of said motion sensor signal, where the motion sensor may be an accelerometer embedded within the device), and display a frame by frame animation (e.g. using frames 0 to 25 from e.g. FIG. 9A or FIG. 9B or any other) assigning the frame at which the user's representation shows a foot landing on the ground (e.g. frame 0 and frame 13), to the time instants at which the user's foot touching the ground is detected, thus achieving a synchronism between the user's representation showing a foot landing on the ground and the user's foot landing on the ground. For example, at the time a new step of the user is detected (in other words, a user's foot landing on the ground is detected), the frame by frame animation may show frame 0 (e.g. showing a user's representation's foot landing on the ground); in subsequent time instants, the following frames are displayed (e.g. respecting time intervals between frames to achieve correspondence between the period of the animation cycle and the period of the user; for instance, if the user's period is 0.5 seconds, which can be determined as the inverse of a determined user's gait cadence (e.g. 2 Hz), and the frame by frame animation has 26 frames (0 to 25) the time interval between frames may be approximately 0.038 seconds=1 second of a whole animation cycle (2 periods)/26 frames); e.g. frame 1 is displayed 0.038 seconds after frame 0 and so on; when a new step is detected, frame 13 should be displayed to maintain synchronism between the user's detected steps and the user's representation's steps; if the user kept cadence constant, we should be normally displaying frame 13 at the time the new user's step is detected; however, if the user changes cadence, we may find ourselves displaying a frame different from frame 13 (e.g. we might be displaying frame 11), so we should display frame 13 instead of frame 11 in order to maintain the synchronism; the process is repeated when the next step of the user is detected, in which case we should display frame 0 again and so on repeating the cycle.

Other embodiments may use any other methods and/or any variations and/or combinations thereof. In some embodiments, the synchronism may be achieved with a latency equal to or below a fraction of one step period (e.g. updating the detection of the time instants at which the user's feet land on the ground with a frequency greater than the user's step frequency, or in other words, fast enough to be able to assign the frame at which the user's representation (or animation) lands on the ground, to the time instant of the detection of the user's foot landing on the ground, before a fraction of one step period has elapsed). Some embodiments may select a time interval (e.g. 0.125 seconds, or 0.1 seconds, or 0.05 seconds, or any other value below a threshold of e.g. 0.125 seconds (and obviously larger than 0 to be physically possible)) for updating the detection of the time instants at which the user's feet land on the ground, regardless of the user's step period, but small enough to be a fraction of a user's step period (e.g. considering normal gait frequencies below 6 Hz, any time interval smaller than e.g. $\frac{1}{6}=0.166$ seconds would be a fraction of a user's step period); consequently, in some embodiments, the synchronism may be achieved with a latency equal to or below a threshold amount of time, where said threshold may be any number equal to or below 0.125 seconds. The referred application U.S. 62/750,292 further describes embodiments where the synchronism latency is equal to or below a fraction of one step period. Other embodiments may use any variations and/or combinations thereof. And in some embodiments, all this may happen while the user's representation (or one or more attributes of the user's representation) is controlled in real time with a determined user's gait velocity and/or cadence and/or stride length and/or activity and/or step count and/or calories burned per time unit, and/or device position, and/or status of a medical condition, and/or balance, and/or steps, and/or any other and/or any variations and/or combinations thereof.

In some embodiments, the user's representation shows its head moving in synchronism with the user's feet landing on (or touching) a ground (or stepping), and this may happen in some embodiments while the user's representation (or one or more attributes) is being controlled in real time with the determined user's gait velocity and/or cadence and/or stride-length and/or activity, and/or calories burned per time unit, and/or device position, and/or status of a medical condition, and/or balance, and/or steps, etc. Analogously to the described case in which the user's representation shows feet landing on (or touching) a ground in synchronism with the user's feet landing on (or touching) a ground, some embodiments may detect the time instants at which the user's feet land on the ground through the analysis of a motion sensor signal (e.g. detecting peaks of maximum amplitude), and display a frame by frame animation (e.g. using frames from e.g. FIG. 9A or FIG. 9B or any other) assigning the frame at which the user's representation shows its head inclined/rotated forward with a maximum inclination/rotation angle (e.g. angle of the approximately vertical bone of the head with respect to the approximately vertical direction, measured over a vertical plane containing the approximately horizontal forward direction, and increased or decreased leveraging a approximately horizontal rotation axis approximately perpendicular to the approximately horizontal forward direction and crossing approximately through the lower edge of said head bone (please refer to FIG. 12 to see an example of head bone going from approximately the top of the head to the neck)), to the time instant at which the user's foot landing on (touching) the ground is detected; subsequent time instants may be assigned frames at which the user's representation shows its head inclined forward with a progressively smaller inclination angle with respect to the vertical direction, until the time instant at which the user's foot is detected to have touched the ground again, at which point a frame with the user's representation showing its head inclined forward with a maximum inclination angle with respect to the vertical direction will be displayed again. By progressively modifying the angles of the head with the vertical direction in between the detections of user's steps, we can achieve a synchronism between the user's representation's head movement and the user's feet landing on the ground. For example, if the user's representation's head's angle with the vertical direction varies between 0 degrees (head perfectly vertical, e.g. when no user's step is detected) and 5 degrees (head slightly bent forward, e.g. when a user's step is detected), we can display a frame by frame animation of the user's representation (e.g. using frames from e.g. FIG. 9A or FIG. 9B or any other) and assign e.g. frame 0 (e.g. assuming it has the maximum inclination angle with respect to the vertical direction (e.g. 5 degrees)) to the time instant at which the user's foot landing on the ground is detected (step detected); subsequent time instants are assigned frames with smaller and smaller head inclination angles (e.g. frame 1 may have inclination angle of 4.5 degrees, frame 2 may have inclination angle of 4 degrees, frame 3 may have inclination angle of 3 degrees, etc.); for example, approximately at frame 7, the inclination angle may be 0 degrees, and it may start increasing again progressively with subsequent frames until the next user's step is detected (e.g. frame 13 is then displayed because said frame shows the user's representation's foot landing on the ground in synchronism with the user's foot landing on the ground being detected, and said frame 13 may have an inclination angle of 5 degrees again); to clarify the idea to the reader, an example of embodiment with frame numbers and user's representation's head's angles with the vertical direction is presented next: frame 0 (user's foot landing on the ground is detected) angle=5 degrees; frame 1 angle=4.5 degrees; frame 2 angle=4 degrees; frame 3 angle=3.5 degrees; frame 4 angle=3 degrees; frame 5 angle=2 degrees; frame 6 angle=1 degrees; frame 7 angle=0 degrees; frame 8 angle=1 degrees; frame 9 angle=2 degrees; frame 10 angle=3 degrees; frame 11 angle=3.5 degrees; frame 12 angle=4.5 degrees; frame 13 (user's foot landing on the ground is detected) angle=5 degrees; frame 14 angle=4.5 degrees; and so on, achieving angle=0 for frame 20, and increasing it again to reach angle=4.5 at frame 25 and repeat the cycle on and on starting again with frame 0 with angle=5 degrees; so the user's representation's head moves cyclically in synchronism with the detections of user's steps (or feet landing on the ground). Consequently, the user's representation's head's movement in synchronism with the user's feet landing on a ground comprises a cyclical forward and backward rotation of the user's representation's head, by an approximately horizontal rotation axis approximately perpendicular to the user's representation's forward movement direction and across a point approximately below the center of the head (e.g. across the lower edge of the head); wherein the range of rotation angles of the head with respect to the approximately vertical direction is about a greater than zero threshold number of degrees; wherein said threshold number of degrees may be less than 35 degrees, and wherein said threshold number of degrees may be about 5 degrees, and wherein a maximum forward rotation angle of the user's representation's head corresponds to a time instant at which the user's foot landing on the ground is detected. In some embodiments, the rotation axis may be perfectly horizontal and perfectly perpendicular to the user's representation's forward movement direction and across the lower edge of the head, while in other embodiments it may be approximately horizontal (e.g. within a threshold number of degrees (e.g. 10, 20, or any other number of degrees, including 0 for perfectly horizontal), and this or similar reasoning may be applicable throughout this specification to any appearance of the term "approximately"), and approximately perpendicular to the user's representation's forward movement direction (e.g. within a threshold number of degrees (e.g. 80, 70, or any other number of degrees, including 90 for perfectly perpendicular)), and across any point approximately by the lower edge of the head (including the lower edge of the user's representation's head, although any other different points approximately below the center of the user's representation's head may be used in some embodiments), while in other embodiments any other configurations and/or numbers and/or variations and/or combinations thereof may be used. It is interesting to note that in 3D modeling, a bone may be associated with the element it is in, and said element moves accordingly (e.g. the entirety of the element may move rigidly) with the movements of said bone; it is also interesting to note that some embodiments may use a different bone to achieve approximately the same effect; for instance, the described movement of the head in synchronism with the user's feet landing on the ground (or stepping), may be achieved by controlling the movements of the neck bone (going approximately from the shoulders to the middle of the head) instead of the head bone. The same may apply to other descriptions (e.g. movement of shoulders, hip, backbone, spine-bone, etc.). For clarity purposes, throughout this specification, the expression detecting the user's steps may be equivalent in some embodiments to detecting the stepping of the user or detecting the user's feet landing on a ground or detecting the user's feet touching a ground.

Some embodiments may use additional attributes to characterize the movement of the head; for example, a lateral angle with respect to the approximately (including perfectly) horizontal forward direction (e.g. head slightly rotating towards the left and/or towards the right, using a approximately vertical axis of rotation approximately across the center of the head (or any point approximately behind the user's representation's center of the head)), which could vary analogously to the previous case, approximately from e.g. −2.5 degrees at frame 0, to e.g. 0 degrees at frame 7, to e.g. 2.5 degrees at frame 13, to e.g. 0 degrees at frame 20 and so on cyclically repeated starting again with −2.5 degrees at frame 0. For clarity purposes, it is interesting to note that in some embodiments, the approximately horizontal forward direction may correspond with the approximately horizontal direction towards the side which the user's representation is facing (in other words, the approximately horizontal direction in which the user's representation would normally move). Consequently, in some embodiments, a user's representation shows a head movement in synchronism with the user's footsteps, (or a user's representation's head's movement in synchronism with the user's feet landing on a ground), wherein the head movement comprises a cyclical lateral rotation of the user's representation's head, by (or using) an approximately vertical rotation axis approximately across the center of the head (or across a point approximately located behind the center of the head); wherein the total range of lateral rotation of the head is about a greater than zero threshold number of degrees; wherein said threshold number of degrees may be less than 35 degrees; and wherein said threshold number of degrees may be about 5 degrees; and wherein a maximum lateral rotation angle of the user's representation's head corresponds to a time instant at which the user's foot landing on the ground is detected.

Analogous principles and descriptions may be extended to characterize movements of different parts (or elements) of the user's representation, in synchronism with the detection of the user's feet landing on the ground (or detection of the user's steps, or the user's stepping).

In some embodiments, the synchronism may be achieved with a latency equal to or below a fraction of one step period (e.g. extending the reasoning described in this specification, or leveraging the referred application U.S. 62/750,292, which further describes embodiments where the synchronism latency is equal to or below a fraction of one step period); in some embodiments, the synchronism may be achieved with a latency equal to or below a threshold amount of time, wherein said threshold may be any number equal to or below 0.125 seconds. And in some embodiments, all this may happen while the user's representation (or one or more attributes of the user's representation) is controlled in real time with a determined user's gait velocity and/or cadence and/or stride length and/or activity and/or step count and/or any other and/or any variations and/or combinations thereof.

For example, a user's representation's shoulders' or shoulders bones' (e.g. an approximately horizontal (please note that throughout this application, the term "approximately horizontal" comprises "perfectly horizontal", and the same reasoning applies to "approximately vertical" comprising "perfectly vertical", "approximately the center of" comprising "the center of", etc.) line linking both shoulders) movement may be synchronized with the detected user's steps (or detecting user's feet landing on a ground or stepping), in analogy to the previous descriptions, using the same type of cyclical variation, for the following angles: 1) a lateral rotation angle (e.g. in addition to 90 degrees) with respect to the approximately horizontal forward direction (e.g. shoulders bones slightly rotating forwards and/or backwards (e.g. right shoulder in opposition to left shoulder), using an approximately vertical axis of rotation approximately across the middle point between both shoulders), which could vary analogously to the previous case, from e.g. about −3.5 (or any other number e.g. greater than about −30) degrees at frame 0, to e.g. 0 degrees at frame 7, to e.g. about 3.5 (or any other number e.g. less than about 30) degrees at frame 13, to e.g. 0 degrees at frame 20 and so on cyclically repeated, starting again with about −3.5 degrees at frame 0; 2) a rotation angle (e.g. in addition to 90 degrees) with respect to the approximately vertical direction (e.g. shoulders bones slightly rotating upwards and/or downwards (e.g. right shoulder in opposition to left shoulder), using the approximately horizontal forward direction approximately across the middle point between both shoulders as axis of rotation), which could vary analogously to the previous case, from e.g. about −1.5 (or any other number e.g. greater than about −20) degrees at frame 0, to e.g. 0 degrees at frame 7, to e.g. about 1.5 (or any other number e.g. less than about 20) degrees at frame 13, to e.g. 0 degrees at frame 20 and so on cyclically repeated, starting again with about −1.5 degrees at frame 0. In some embodiments, the synchronism may be achieved with a latency equal to or below a fraction of one step period (e.g. extending the reasoning described in this specification, or leveraging the referred application U.S. 62/750,292, which further describes embodiments where the synchronism latency is equal to or below a fraction of one step period); in some embodiments, the synchronism may be achieved with a latency equal to or below a threshold amount of time, wherein said threshold may be any number equal to or below 0.125 seconds. And in some embodiments, all this may happen while the user's representation (or one or more attributes of the user's representation) is controlled in real time with a determined user's gait velocity and/or cadence and/or stride length and/or activity and/or step count and/or calories burned per time unit and/or device position and/or status of a medical condition and/or any other and/or any variations and/or combinations thereof.

For example, a user's representation's back's or back-bone's, or spine-bone's (e.g. an approximately vertical line approximately linking the neck with the hip in some embodiments, although it may vary in other embodiments) movement may be synchronized with the detected user's steps (or detecting user's feet landing on a ground or stepping), in analogy to the previous description, using the same type of cyclical variation, for the following angles: 1) a rotation angle (e.g. in addition to approximately 90 degrees) with respect to the approximately horizontal forward direction (e.g. back-bone slightly rotating forwards and/or backwards, using an approximately horizontal axis of rotation approximately perpendicular to the approximately horizontal forward direction, across a point approximately by the lower edge of the back or the back's bone (or across a point approximately below the middle of the back or the back's bone)), which could vary analogously to the previous case, from e.g. about −3.5 (or any other number e.g. greater than about −30) degrees at frame 0, to e.g. 0 degrees at frame 7, to e.g. about 3.5 (or any other number e.g. less than about 30) degrees at frame 13, to e.g. 0 degrees at frame 20 and so on cyclically repeated, starting again with about −3.5 degrees at frame 0; 2) a rotation angle with respect to an approximately vertical plane containing the approximately horizontal forward direction, using the approximately vertical direction as axis of rotation approximately across the back-bone, which could vary analogously to the previous case, from e.g. about −1.5 (or any other number e.g. greater than about −20) degrees at frame 0, to e.g. 0 degrees at frame 7, to e.g. about 1.5 (or any other number e.g. less than about 20) degrees at frame 13, to e.g. 0 degrees at frame 20 and so on cyclically repeated, starting again with about −1.5 degrees at frame 0. In some embodiments, the synchronism may be achieved with a latency equal to or below a fraction of one step period (e.g. extending the reasoning described in this specification, or leveraging the referred application U.S. 62/750,292, which further describes embodiments where the synchronism latency is equal to or below a fraction of one step period); in some embodiments, the synchronism may be achieved with a latency equal to or below a threshold amount of time, wherein said threshold may be any number equal to or below 0.125 seconds. And in some embodiments, all this may happen while the user's representation (or one or more attributes of the user's representation) is controlled in real time with a determined user's gait velocity and/or cadence and/or stride length and/or activity and/or step count and/or any other and/or any variations and/or combinations thereof.

For example, a user's representation's hip's or hip bone's (e.g. in some embodiments, a vertical bone going from approximately the intersection of the legs to the lower edge of the back-bone, while in other embodiments, it may be a horizontal bone approximately located around the hip area of the user's representation, or any other type in other embodiments) movement may be synchronized with the detected user's steps (or detecting user's feet landing on a ground or stepping), in analogy to the previous descriptions, using the same type of cyclical variation, for the following angles (considering, e.g. a vertical hip bone): 1) a rotation angle (e.g. in addition to approximately 90 degrees) with respect to the approximately horizontal forward direction (e.g. hip-bone slightly rotating forwards and/or backwards, using an approximately horizontal axis of rotation, wherein said approximately horizontal axis of rotation is approximately perpendicular to the approximately horizontal forward direction, approximately across the lower edge of said bone, or a point below the middle of said bone), which could vary analogously to the previous case, from e.g. about −0.75 (or any other number e.g. greater than about −20) degrees at frame 0, to e.g. 0 degrees at frame 7, to about 0.75 (or any other number e.g. less than about 20) degrees at frame 13, to e.g. 0 degrees at frame 20 and so on cyclically repeated, starting again with about −0.75 degrees at frame 0; 2) a rotation angle with respect to an approximately vertical plane containing the approximately horizontal forward direction, using the approximately vertical direction as axis of rotation approximately across a point approximately by the center (or middle) of the user's representation (e.g. across the back-bone), which could vary analogously to the previous case, from e.g. about −4.5 (or any other number e.g. greater than about −30) degrees at frame 0, to e.g. 0 degrees at frame 7, to e.g. about 4.5 (or any other number e.g. less than about 30) degrees at frame 13, to e.g. 0 degrees at frame 20 and so on cyclically repeated, starting again with about −4.5 degrees at frame 0; 3) a cyclical up and down movement of the hip (and the upper body of the user's representation), along an approximately vertical axis, approximately across the middle of the user's representation (e.g. approximately the middle point of the hip), with the lowest position for the hip (and upper body) at every detected step (e.g. approximately frames 0 and 13), and progressively lifting the hip (and upper body) in between steps to the highest position for the hip (and upper body) corresponding to time instants between detections of steps (e.g. frames 7 and 20), wherein the height difference between the lowest and the highest positions is about a threshold percentage of the user's representation's height, wherein said threshold may be lower than about 30% (e.g. about 6%). In some embodiments, the synchronism may be achieved with a latency equal to or below a fraction of one step period (e.g. extending the reasoning described in this specification, or leveraging the referred application U.S. 62/750,292, which further describes embodiments where the synchronism latency is equal to or below a fraction of one step period); in some embodiments, the synchronism may be achieved with a latency equal to or below a threshold amount of time, wherein said threshold may be any number equal to or below 0.125 seconds. And in some embodiments, all this may happen while the user's representation (or one or more attributes of the user's representation) is controlled in real time with a determined user's gait velocity and/or cadence and/or stride length and/or activity and/or step count and/or any other and/or any variations and/or combinations thereof.

Figure 10A:
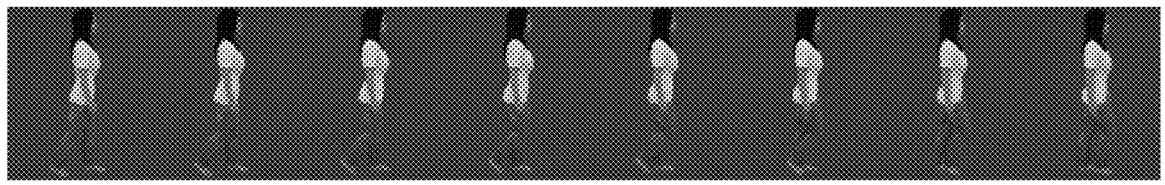
FIG. 10A, 10B, 10C, 10D, 10E, 10F show scaled portions of the previous images strip files for a representation of a user with different gait attributes according to one embodiment.
Figure 10B:
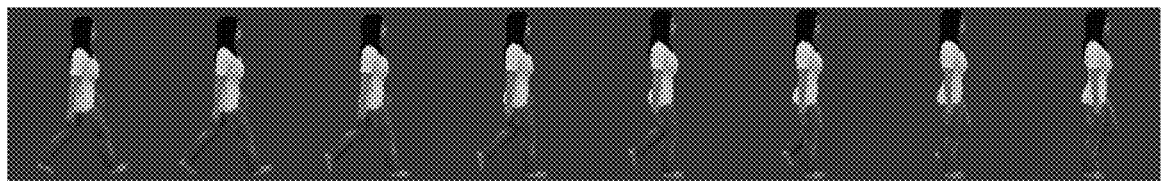
Figure 10C:
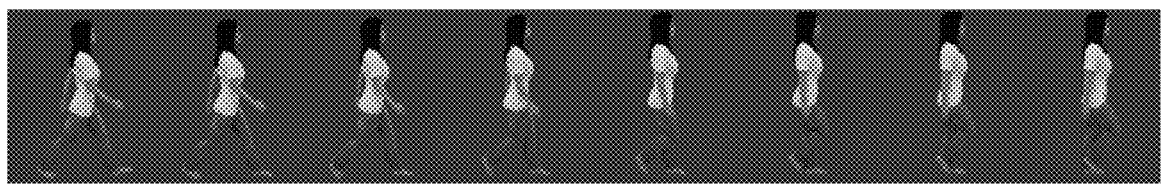
Figure 10D:
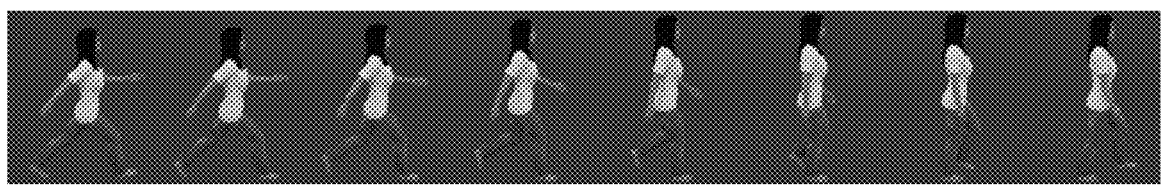
Figure 10E:
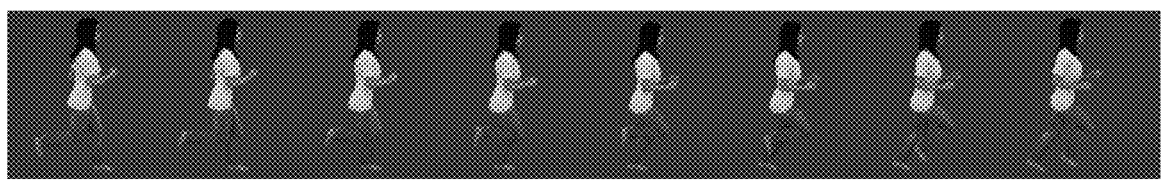
Figure 10F:
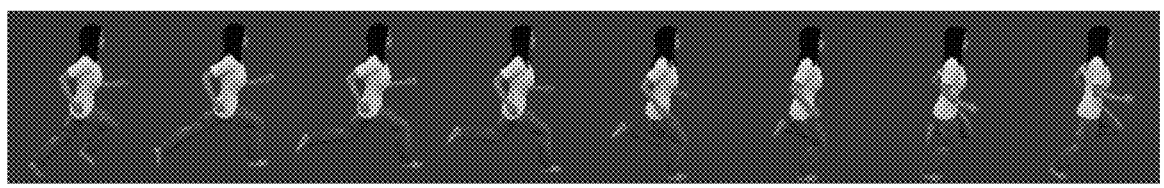

For example, a user's representation's hair's or hair element's (e.g. in some embodiments, it may be considered a soft body or element that may be attached to the user's representation's head and may have soft-body physics applied to it in order to easily model the movement/behavior of said element with the whole representation's movement, while in other embodiments it may be modeled in other ways) movement may be synchronized with the detected user's steps (or detecting user's feet landing on a ground or stepping), in analogy to the previous descriptions, using the same type of cyclical variation. By way of example without limitation, in some embodiments, animating the user's representation's hair as a soft body (specific details are provided e.g. in "Animating with Blender: How to Create Short Animations from Start to Finish" by Roland Hess, or "Bounce, Tumble, and Splash!: Simulating the Physical World with Blender 3D" by Tony Mullen, all of which are herein incorporated by reference for all purposes), we can choose the softness of the whole hair element, or the softness of parts of the hair element, which will control the movement of the hair element as the whole user's representation moves in a virtual environment; for example, if soft body simulation is used with the user's representation's hair, and we select a level of softness (or any other attribute; for example, in some embodiments, hair particles can have dynamic properties using physics, and stiffness may be one of the attributes we can use to control the bending stiffness of the hair strands, while in other embodiments we can use any other attributes (e.g. paint weight or any other) and/or any variations and/or combinations thereof) that makes the hair bounce at every user's representation's footstep (e.g. selecting a level of softness of 0.5 in a scale from 0 (no softness) to 1 (softest), while other embodiments may choose other levels, and other embodiments may empirically/experimentally choose a level of softness (or any other attribute) for the hair or for parts of the hair that provides a desired bouncing movement with every user's representation's footstep (in other words, we can control the level of softness of the hair to achieve a desired bouncing movement of the hair in synchronism with the user's representation's footsteps, which may themselves be synchronized with the user's footsteps)), we can choose how the user's representation's hair will bounce with the user's representation's footsteps (feet landing on the ground); by way of example without limitation, Blender allows designers to select the whole hair as a group, and by means of a "Weight Paint" mode, designers can assign different weights to different parts of the hair (by painting the different parts of the hair with paints of different weight); for example, we can assign 3 or more different weights to different parts of the hair (e.g. 3 or more paints with different weight may be assigned to different parts of the hair; e.g. a paint with heavy weight (e.g. 0.7 out of 1) for the roots of the hair and/or the parts of the hair close to the skull, and a paint with lighter weight (e.g. 0.4 out of 1) for the parts of the hair further from the skull and different from the roots, and a paint with even lighter weight (e.g. 0.1 out of 1) for the tips of the hair; additional weights can be assigned in other embodiments); consequently, the 3 or more different weights assigned to 3 or more different parts of the user's representation's hair, will achieve a realistic bouncing/behavior with the user's representation's movement; in other words, the hair's movement may be achieved assigning 3 or more different weights to different parts of the hair; or the hair's movement may be achieved assigning 3 or more different weights to the hair (in other words, the hair leverages three or more different weights); for instance, FIG. 10E and FIG. 10F show different configurations/poses/bouncing levels of the user's representation's hair; consequently, we can control how the user's representation's hair bounces with the user's representation's movement; in other words, we can control the bouncing movement of the hair with the user's representation's stepping, and make the hair bounce in synchronism with the user's representation's footsteps (e.g. application of soft-body physics or any other technique implemented within available software packages such as Blender allows it automatically); since we can achieve a synchronism between the user's representation's footsteps and the user's footsteps, we can achieve a synchronism between the user's representation's hair's bouncing movement and the user's footsteps; in other words, we can achieve the user's representation showing hair (a single hair and/or a group of hairs and/or an element of hair, etc.) moving in synchronism with the user's feet landing on the ground (or stepping). In some embodiments, the synchronism may be achieved with a latency equal to or below a fraction of one step period (e.g. extending the reasoning described in this specification, or leveraging the referred application U.S. 62/750,292, which further describes embodiments where the synchronism latency is equal to or below a fraction of one step period); in some embodiments, the synchronism may be achieved with a latency equal to or below a threshold amount of time, where said threshold may be any number equal to or below 0.125 seconds (e.g. 0.1 seconds, 0.05 seconds, 0.025 seconds, etc.). And in some embodiments, all this may happen while the user's representation (or one or more attributes of the user's representation) is controlled in real time with a determined user's gait velocity and/or cadence and/or stride length and/or activity and/or step count and/or any other and/or any variations and/or combinations thereof.

In some embodiments, the user's representation shows facial expressions in synchronism with the user's feet landing on (or touching) a ground (or stepping), and this may happen in some embodiments while the user's representation (or one or more attributes) is being controlled in real time with the determined user's gait velocity and/or cadence and/or stride-length and/or activity and/or calories burned per time unit and/or device position and/or status of a medical condition and/or step count, etc. For example, analogously to the way we can synchronize movements of a user's representation's head with the user's steps, we can synchronize movements of elements of the user's representation's face (e.g. eyes, eye-lids, eyebrows, mouth, chin, etc.) with the user's steps, and those facial movements may be considered as facial expressions; this can be achieved e.g. in Blender by assigning bones to those particular elements we want to move, and moving them in synchronism with the user's steps, by moving their associated bones; for example, we could lower the chin (e.g. by approximately 1 centimeter) at every step detection, rising it back to its original position in between detection of steps, in such a way that the chin would have a cyclic up and down movement in synchronism with the user's steps; or we can move the eyes of the user's representation in any direction (e.g. progressive and cyclical sideways rotations to the left by approximately 30 degrees (or any other angle) when a step is detected, and to the right by approximately 30 degrees (or any other angle) when the next step is detected); or we could lower the eyebrows (e.g. by approximately 0.5 centimeters) at every step detection, rising them back to their original position in between detection of steps, in such a way that the eyebrows would have a cyclic up and down movement in synchronism with the user's steps. And analogous reasoning can be followed in other embodiments to show the user's representation's arms, legs, hands, fingers in the hands, etc. move in synchronism with the user's feet landing on (or touching) a ground (or stepping), and this may happen in some embodiments while the user's representation (or one or more attributes) is being controlled in real time with the determined user's gait velocity and/or cadence and/or stride-length and/or activity and/or calories burned per time unit and/or device position and/or status of a medical condition and/or step count, etc. For example, analogously to the way we can synchronize movements of a user's representation's head with the user's steps, we can synchronize movements of the arms, legs, hands, fingers in the hands, etc. with the user's steps; for example, we could assign a cyclic rotation to the arms by an approximately horizontal rotation axis approximately perpendicular to the forward movement direction and across approximately the upper edge of the arm in synchronism with the detected steps (e.g. maximum advancement due to the rotation is achieved when a step is detected; after that detection, the rotation reverses direction and progressively decreases the rotation angle to the point of maximum retracement when the next step is detected); for example, we could assign a cyclic rotation to the legs by an approximately horizontal rotation axis approximately perpendicular to the forward movement direction and across approximately the upper edge of the leg in synchronism with the detected steps (e.g. maximum advancement due to the rotation is achieved when a step is detected; after that detection, the rotation reverses direction and progressively decreases the rotation angle to the point of maximum retracement when the next step is detected); for example, we could assign a cyclic rotation to the hands by an approximately horizontal rotation axis approximately perpendicular to the forward movement direction and across approximately the upper edge of the hand in synchronism with the detected steps (e.g. maximum advancement due to the rotation is achieved when a step is detected; after that detection, the rotation reverses direction and progressively decreases the rotation angle to the point of maximum retracement when the next step is detected); rotation angles for the arms, legs and hands can be approximately less than 90 degrees; other particular examples of embodiments can be observed in FIGS. 9A-9F and 10A-10F. For example, we could assign a cyclic rotation to the fingers in the hands by a rotation axis approximately contained with the plane of the hand, and approximately perpendicular to the fingers and across a point approximately located by the beginning of the finger(s) (i.e. edge closest to the elbow when the hand is open) in synchronism with the detected steps (e.g. maximum advancement due to the rotation is achieved in between detection of steps; and the rotation reverses direction and progressively decreases the rotation angle to the point of maximum retracement when the steps are detected; this approach would give the impression that the fingers/hands are getting closed at every step, but they open in between steps; opposite and/or different approaches and/or variations and/or combinations thereof may also be possible; rotation angles for the fingers can be approximately less than 90 degrees). Regarding the latency for all the cases described in this paragraph, we can apply analogous reasoning as in paragraphs above; consequently, the same latency descriptions of previous paragraphs apply to all the cases described in this paragraph; for example, in some embodiments, the synchronism may be achieved with a latency equal to or below a threshold amount of time, where said threshold may be any number equal to or below 0.125 seconds.

In some embodiments, a gait cadence of the user's representation is controlled in real time with a determined gait cadence of the user, as described at least in paragraph of application U.S. 62/651,409 entitled "Control Strategies For Mobile Using Gait Analysis", by David Martin, filed on Apr. 2, 2018, herein incorporated by reference for all purposes. For example, as shown in FIG. 13 and FIG. 11A, the user's determined cadence may control the user's representation's cadence in real time and with an update frequency larger than the user's step frequency: the variable completeAnimationPeriod is controlled by the determined (in real time and with an update frequency larger than the user's step frequency) user's cadence, and it controls the value of the variable currentFrame, which is responsible for how fast a whole gait cycle of the user's representation is displayed, or how long it will take to display a whole user's representation's gait cycle (e.g. doDraw method in FIG. 11B is called with regular frequency of, for instance, 60 Hz, and this method calls the manageCurrentFrame method (FIG. 11A) to control which frame to be rendered on the device screen (currentFrame); as shown in FIG. 11A, if completeAnimationPeriod is large, it will take long time for the value of currentFrame to change, while if completeAnimationPeriod is short, it will take short time for the value of currentFrame to change; thus we are controlling the time it takes for currentFrame to change, or the time it takes for frames to change, or the time it takes for 26 frames to be changed, or the time it takes for a whole gait cycle to complete, or the time period of the gait, or the cadence or frequency (=1/period) of the gait of the user's representation on the device screen). At the same time that the user's determined cadence controls the user's representation's cadence, in the same conditions it may also control other attributes in the user's representation. Additional details are included at least in the referred application U.S. 62/651,409. And in some embodiments, all this may happen while the user's representation (or one or more attributes of the user's representation) is controlled in real time with a determined user's gait velocity and/or cadence and/or stride length and/or activity and/or step count and/or any other and/or any variations and/or combinations thereof. And in particular embodiments, the user's representation may additionally show feet landing on a ground in synchronism with the user's feet landing on a ground, and/or a head moving in synchronism with the user's feet landing on a ground (or stepping or footsteps) and/or shoulders moving in synchronism with the user's footsteps, and/or a back moving in synchronism with the user's footsteps, and/or a hip moving in synchronism with the user's footsteps, and/or a hair moving in synchronism with the user's footsteps, and/or any others and/or any variations and/or combinations thereof.

By way of example without limitation, some embodiments may synchronize the user's representation with the determined user's gait cadence (e.g. controlling in real time the user's representation's gait cadence with the determined user's gait cadence, and keeping both cadences constantly equal, for instance updating both cadences with a frequency greater than the user's step frequency, in such a way that the user's representation moves in synchronism with the determined user's gait cadence), and at the same time, leverage a threshold number of different animations for a same type of gait activity. For example, while the user performs a walking activity, some embodiments may use four different animations representing the walking activity, but with different attributes in the user's representation. For instance, FIGS. 9A, 9B, 9C and 9D show four different images/frames strip files from which four different animations may be obtained, all for the same activity (walking), but with different attributes in the user's representation (e.g. different stride length, different angles in the elbows, different extensions in the arms, different angles in the head, different angles in the shoulders, different angles in the back, different angles in the hip, etc.). For example, while the user performs a running activity, some embodiments may use two different animations representing the running activity, but with different attributes in the user's representation. For instance, FIGS. 9E, and 9F show two different images/frames strip files from which two different animations may be obtained, all for the same activity (running), but with different attributes in the user's representation (e.g. different stride length, different angles in the elbows, different extensions in the arms, different angles in the head, different angles in the shoulders, different angles in the back, different angles in the hip, different bouncing movement of the hair, etc.). Other embodiments may use any other approaches and/or any variations and/or combinations thereof. It is interesting to note that in some embodiments the threshold number of different animations for a same activity can be any integer value, including any greater than two. It is also interesting to note that in some embodiments the different animations may be selected in terms of factors comprising the determined user's gait cadence and/or velocity and/or stride length and/or calories burned per time unit and/or device position and/or step count and/or status of a medical condition and/or any other and/or any variations and/or combinations thereof. For example, the animation corresponding to FIG. 9A may be selected for values of determined user's gait cadence below 1 Hz, while the animation corresponding to FIG. 9B may be selected for values of determined user's gait cadence equal to or greater than 1 Hz but below 1.5 Hz, while the animation corresponding to FIG. 9C may be selected for values of determined user's gait cadence equal to or greater than 1.5 Hz but below 2 Hz, while the animation corresponding to FIG. 9D may be selected for values of determined user's gait cadence equal to or greater than 2 Hz, while other embodiments may use any other criteria. For example, the animation corresponding to FIG. 9A may be selected for values of determined user's stride-length below 60 cm, while the animation corresponding to FIG. 9B may be selected for values of determined user's stride-length equal to or greater than 60 cm but below 90 cm, while the animation corresponding to FIG. 9C may be selected for values of determined user's stride-length equal to or greater than 90 cm but below 140 cm, while the animation corresponding to FIG. 9D may be selected for values of determined user's stride-length equal to or greater than 140 cm, while other embodiments may use any other criteria. For example, the animation corresponding to FIG. 9A may be selected for values of determined user's gait velocity below 1 mph while the animation corresponding to FIG. 9B may be selected for values of determined user's gait velocity equal to or greater than 1 mph but below 2 mph, while the animation corresponding to FIG. 9C may be selected for values of determined user's gait velocity equal to or greater than 2 mph but below 3 mph, while the animation corresponding to FIG. 9D may be selected for values of determined user's gait velocity equal to or greater than 3 mph, while other embodiments may use any other criteria. All these examples can be extended for different attributes (e.g. calories burned per time unit and/or device position and/or step count and/or status of a medical condition and/or any other and/or any variations and/or combinations thereof).

Some embodiments may also control a stride length of the user's representation in real time with a determined stride length of the user, as described at least in paragraph [0116] of application U.S. 62/651,409 entitled "Control Strategies For Mobile Using Gait Analysis", by David Martin, filed on Apr. 2, 2018, herein incorporated by reference for all purposes. For example, the user's determined stride length may control the stride length of the user's representation being displayed on the device screen, and this may be achieved in some embodiments by controlling, leveraging the value of determined user's stride length, the selection of an appropriate images strip file where the user's representation has the appropriate value of stride length (e.g. in pseudocode: if (determined_stride_length==value1) {then, images_strip_file="file1.png";} else if (determined_stride_length==value2) {then, images_strip_file="file2.png";} . . . and so on). Additional details can be found at least in paragraphs [0112-0116] of the referred application U.S. 62/651,409. And in some embodiments, all this may happen while the user's representation (or one or more attributes of the user's representation) is controlled in real time with a determined user's gait velocity and/or cadence and/or stride length and/or activity and/or step count and/or any other and/or any variations and/or combinations thereof.

Similar reasoning can be extended to some embodiments where the user's representation's calories burned per time unit are controlled in real time with the determined calories burned per time unit of the user, as described at least in paragraph [0120] of application U.S. 62/651,409 entitled "Control Strategies For Mobile Using Gait Analysis", by David Martin, filed on Apr. 2, 2018, herein incorporated by reference for all purposes. Similar reasoning can be extended to some embodiments where the user's representation's device position is controlled in real time with the determined user's device position, as described at least in paragraph [0121] of the referred application U.S. 62/651, 409. It is also interesting to note that in some embodiments, the referred user's device position may be determined in real time leveraging a determined gait cadence of the user, as described at least in paragraph [0126] of the referred application U.S. 62/651,409. Similar reasoning can be extended to some embodiments where the user's representation's step count is controlled in real time with the determined step count of the user, as described at least in paragraph [0105] of application U.S. 62/750,292 entitled "Gait Analysis applied for control", by David Martin, filed on Oct. 25, 2018, herein incorporated by reference for all purposes. It is interesting to note that in some embodiments, the user's step count is determined in real time leveraging a determined gait cadence of the user, as described at least in the referred application U.S. 62/750,292. Similar reasoning can be extended to some embodiments where the user's representation's activity is controlled in real time with the determined user's activity, as described at least in paragraph [0118] of the referred application U.S. 62/651,409. It is also interesting to note that in some embodiments, the referred user's activity may be determined in real time leveraging a determined gait cadence of the user, as described at least in paragraph [0126] of the referred application U.S. 62/651, 409. And in some embodiments, all this may happen while the user's representation (or one or more attributes of the user's representation) is controlled in real time with a determined user's gait velocity and/or cadence and/or stride length and/or activity and/or step count and/or any other and/or any variations and/or combinations thereof.

Similar reasoning can be extended to some embodiments where the user's representation's velocity is controlled in real time with the determined gait velocity of the user, as described at least in application U.S. Ser. No. 14/922,174 entitled "Application of Gait Characteristics For Mobile", by David Martin, filed on Oct. 15, 2015, herein incorporated by reference for all purposes, and in paragraph [0119] of application U.S. 62/651,409 entitled "Control Strategies For Mobile Using Gait Analysis", by David Martin, filed on Apr. 2, 2018, herein incorporated by reference for all purposes. And in some particular embodiments, the controlling of the user's representation's velocity is performed with an update frequency chosen in terms of an update frequency of the determining of the user's gait velocity. For example, the update frequency of the controlling of the user's representation's velocity may be equal to the update frequency of the determining of the user's gait velocity, as described at least in the referred application U.S. Ser. No. 14/922,174, while other embodiments may choose to e.g. update the controlling of the user's representation's velocity at half (or at double, or with any other type of relationship) the update frequency of the determining of the user's gait velocity. It is interesting to note that in some embodiments the user's representation represents a human being, and an aspect of an application in the user's device (e.g. the activity of the user's representation being displayed in the user's device within an application) is controlled with a determined gait activity of the user in real time. And in some embodiments, the controlling of the user's representation's velocity with the determined gait velocity is enabled after a gait activity of the user has been recognized (e.g. we may be continuously determining the user's gait activity, and for instance, if the user's device is still, no gait activity such as walking, jogging, running, etc. is recognized, so we may disable any controlling; however, if the user starts moving, as soon as we recognize/determine the user's activity, e.g. walking, we may enable the controlling of the user's representation's velocity with a determined user's gait velocity), as described at least in the referred application U.S. Ser. No. 14/922,174. It is interesting to note, as already mentioned, that some embodiments may substitute any of the used terms (e.g. activity and/or velocity and/or cadence and/or stride-length and/or calories burned per time unit and/or step count and/or status of a medical condition and/or device position and/or any other) by each and every one of them and/or any variations and/or combinations thereof; by way of example without limitation, throughout any descriptions in this specification or any of the referred applications, the term velocity may be substituted in some embodiments by the term cadence and/or stride-length and/or activity and/or calories burned per time unit and/or step count and/or status of a medical condition and/or device position and/or any other and/or any variations and/or combinations thereof. In this sense, an aspect of an application in the user's device (e.g. the gait cadence of the user's representation, which may be displayed on the user's device screen as part of an application) may be controlled in some embodiments with a determined gait cadence of the user; and in some embodiments, all this may happen while the user's representation (or one or more attributes of the user's representation) is controlled in real time with a determined user's gait velocity and/or cadence and/or stride length and/or activity and/or step count and/or any other and/or any variations and/or combinations thereof. At the same time, in some embodiments, the user's representation can interact with elements in a virtual environment, as described at least in the referred applications U.S. Ser. No. 14/922,174 and U.S. 62/651,409, and in some embodiments the user also participates in a networking environment with other users, and shares the same type of representation with the other users also represented in the virtual environment, wherein the virtual environment further includes one or more dashboard elements indicating velocity, and wherein the user's representation's gait activity is controlled in real time with the determined gait activity, and wherein the controlling of the user's representation's velocity with the determined gait velocity is enabled after a gait activity of the user has been recognized. In other embodiments, the user participates in a networking environment with other users, and one or more users also represented in the virtual environment, are represented with a different type of representation (e.g. human being vs means of transportation vs non-human being and/or young human being vs old human being and/or human being belonging to one team vs human being belonging to a different team (e.g. dressed in a different way) and/or any others and/or any variations and/or combinations thereof). And in some embodiments, the virtual environment further includes one or more dashboard elements indicating velocity (e.g. users' representations' velocities). In other embodiments, the user's representation may represent a means of transportation (e.g. a car), and the user's representation can interact with elements in a virtual environment, wherein the user may participate in a networking environment with other users, and share the same type of representation with the other users also represented in the virtual environment, wherein the virtual environment may further include one or more dashboard elements indicating velocity (e.g. the user's representations' velocities), and wherein an aspect of an application in the user's device (e.g. the enabling of the controlling with the determined user's velocity) may be controlled with a determined gait activity of the user, and wherein the controlling of the user's representation's velocity with the determined gait velocity may be enabled after a gait activity of the user has been recognized, and wherein the determining of the user's gait velocity may be performed within a thread of an application separate from a main thread of the application.

It is interesting to note that in some embodiments, by way of example without limitation, any of the cases/examples described for the update frequency of the determining of the gait characteristic may be used in combination (e.g. simultaneously or in any other way) with any of the cases/examples described for the update frequency of the controlling of an aspect and/or one or more attributes of the user's representation with the determined gait characteristic. The same applies to any of the cases/examples described regarding the thread(s) in which any of the determining and/or controlling is performed. And again, any of the embodiments and/or any of their variations and/or combinations can use interchangeably or in any other way any of the gait characteristics (e.g. gait velocity and/or cadence and/or stride-length and/or activity and/or calories burned per time unit and/or step count and/or device position and/or status of a medical condition and/or any other and/or any variations and/or combinations thereof).

By way of example without limitation, some embodiments may be controlling a velocity of the user's representation with a determined user's gait velocity in real time, and the determining of the user's gait velocity may be performed within a main thread of an application, and the controlling of the user's representation's velocity may be performed with an update frequency chosen in terms of an update frequency of the determining of the user's gait velocity, and the controlling of the user's representation's velocity may be performed within a main thread of an application, and the update frequency of the controlling of the user's representation's velocity may be equal to the update frequency of the determining of the user's gait velocity and/or the controlling of the user's representation's velocity may performed within a thread of an application separate from a main thread of the application in other circumstances. In other examples of embodiments, the controlling of the user's representation's velocity may be performed within the main thread of the application, and the controlling of the user's representation's velocity may be performed with an update frequency chosen in terms of an update frequency of the determining of the user's gait velocity, and the update frequency of the controlling of the user's representation's velocity may be equal to the update frequency of the determining of the user's gait velocity. In other examples of embodiments, the controlling of the user's representation's velocity may be performed with an update frequency, which may be a constant value, while a sampling frequency of an accelerometer of the user's device is variable, and the accelerometer of the user's device may be leveraged in the determining of the user's gait velocity; still in other examples of embodiments, the controlling of the user's representation's velocity may be performed with an update frequency, which may be a constant value greater than an upper edge of a frequency band of the user's gait activity and lower than a sampling frequency of an accelerometer of the user's device, and the accelerometer of the user's device may be leveraged in the determining of the user's gait velocity; and/or the controlling of the user's representation's velocity may be performed with an update frequency, which may be a constant value greater than an upper edge of a frequency band of the user's gait activity and lower than a sampling frequency of an accelerometer of the user's device, while the sampling frequency of the accelerometer of the user's device is variable, and the accelerometer of the user's device may be leveraged in the determining of the user's gait velocity; and/or the controlling of the user's representation's velocity may be performed with an update frequency different from the application's frame (or screen) refresh rate; and/or the controlling of the user's representation's velocity may be performed within a thread of the application separate from the main thread of the application; still in other examples of embodiments, the determining of the user's gait velocity may be performed within a thread of an application separate from a main thread of the application, and the controlling of the user's representation's velocity may be performed within a thread of the application separate from the main thread of the application or the controlling of the user's representation's velocity may be performed within the main thread of the application; still in other examples of embodiments, the controlling may comprise controlling one or more attributes (e.g. color and texture of the face skin) of the user's representation with the determined gait velocity in real time, and wherein the one or more attributes of the user's representation may comprise one or more attributes different from a velocity (e.g. color and texture of the face skin) and/or wherein the one or more attributes of the user's representation may comprise one or more attributes different from properties of a transformation of the whole user's representation, or in other words, wherein said attributes are not properties (e.g. position/location xyz, rotation xyzw, scale xyz) of a transformation of the whole user's representation (e.g. said attributes may be properties of a transform affecting the user's representation's arm's right elbow angle and/or left elbow angle and/or color of face skin and/or texture of neck skin and/or hair bouncing and/or stride length and/or any other and/or any variations and/or combinations thereof); or the attributes controlled with the determined user's gait velocity may be different from translations (or location/position components x,y,z) and/or rotations (e.g. x,y,z,w) and/or scales (e.g.

x,y,z); for instance, in the case of e.g. the user's representation being a means of transportation (e.g. a car), the controlled attributes can be: smoke amount coming out of the exhaustion tube, sparks appearing on the wheels, speed of rotation of wheels, velocity indication on the dashboards (both dashboard and user's representation may be displayed simultaneously), color of car, etc.; other embodiments may determine the user's gait velocity with an update frequency larger than the user's step frequency and control an aspect of an application with the determined user's velocity and with said update frequency; and within this last case, in some embodiments, said update frequency may be a constant and/or may be chosen in terms of the user's step frequency, and/or may be lower than an accelerometer sampling rate; and in some embodiments, an aspect of the application may be controlled with the recognition that the user's gait activity has stopped (e.g. the screen brightness can be reduced after the stop of the user's activity has been recognized); in other embodiments, a user's representation may not be part of a virtual environment, but instead be displayed independently or without any relationship to a virtual environment; other embodiments using update frequencies (for determining the user's gait velocity/cadence/stride-length and/or for controlling with said velocity/cadence/stride-length) chosen in terms of the user's step frequency (e.g. greater than the user's step frequency), may not need to monitor the user's step frequency at all (e.g. if an update frequency is set as a constant larger than the user's step frequency, and said constant is e.g. 15 Hz or above, there is no need monitor the user's step frequency, because it is not going to reach 15 Hz, so an update frequency of 15 Hz which is constant does not need to monitor the user's step frequency to fulfil the requirement that it is above the user's step frequency, and this may apply to any constant value above the upper edge of the gait frequency band (e.g. approximately 2.5 Hz for walking, or approximately 7 Hz for running, wherein said upper edge may be determined empirically/experimentally in some embodiments)); other embodiments may determine any gait parameter (e.g. velocity) without relying on signals external to the user's device (e.g. leveraging only an accelerometer, without relying on satellite signals and/or infrared signals and/or any other type of external signals); still in other examples of embodiments, any other attributes and/or elements and/or substitutions (e.g. substituting velocity by cadence and/or stride-length and/or activity and/or calories burned per time unit and/or device position and/or step count and/or status of a medical condition and/or any other and/or any variations and/or combinations thereof) and/or procedures and/or methods and any variations and/or combinations thereof may also be possible.

In the same sense, some examples of embodiments are provided next, emphasizing on the idea that the term(s) "velocity", or "gait velocity", or "gait characteristic(s)" can be substituted throughout all this specification and throughout all the references incorporated in this specification, by velocity and/or cadence and/or stride-length and/or activity and/or calories burned per time unit and/or device position and/or step count and/or status of a medical condition and/or any other and/or any variations and/or combinations thereof; in fact, an example of embodiment described with the help of the code of FIG. 13 shows that we can obtain/determine simultaneously a variety of the user's gait characteristics/parameters; for example FIG. 13 shows that we can directly obtain velocity, calories burned per time unit, cadence, and activity from the "determine_gait_parameters" method, while in other embodiments we can directly obtain/determine from said method (or an adaptation/variation of said method) additional gait characteristics/parameters such as stride or step length (e.g. dividing velocity by cadence) and device position (e.g. using any machine learning technique leveraging any training set gathered in any way and using the gait characteristics we have already determined as features) and status of a medical condition (e.g. using any machine learning technique leveraging any training set gathered in any way and using the gait characteristics we have already determined as features) and any other using any of the mentioned techniques/approaches/methods and/or any others and/or any variations and/or combinations thereof; and for clarity purposes, in the examples of embodiments that follow (the same is applicable to any others as mentioned above), we will use the term "gait characteristic(s)", knowing that it can refer to any and/or all and/or any combinations of any of the mentioned gait characteristics/parameters.

For example, in some embodiments, the user's gait characteristic may be determined (e.g. with an update frequency greater than the user's step frequency), and we may control (e.g. with the same update frequency at which the gait characteristic is determined, or with any other) an aspect of an application with the determined user's gait characteristic. It is also interesting to note that throughout this specification and throughout all the references incorporated in this specification, an application in/of the mobile or wearable device may comprise, by way of example without limitation, any type of application and/or program and/or code and/or practice and/or process and/or procedure and/or robot and/or messaging system and/or entity and/or action and/or any kind of utilization of any means for any purposes, that may be implemented and/or used and/or leveraged and/or any other action and/or in any way be connected and/or related with (or by means of, or any other applicable expression) the mobile or wearable device; and in some embodiments, an application may also comprise any material, product or program which is designed for end-user to use, and/or any type of software (also mobile apps, and/or any collection of data and/or instructions that may be used in any way, and/or any type of information processed by any type of systems (including computing), etc.) designed to help the user to perform any task. Following with the previous example of embodiment where the update frequency of the determining of the gait characteristic (e.g. greater than the user's step frequency) is equal to the update frequency of the controlling of an aspect of an application with said gait characteristic, in some embodiments said update frequency may be a constant (e.g. 6 Hz or 60 Hz or 120 Hz), while in other embodiments it may be chosen in terms of the user's step frequency (e.g. double the user's step frequency, or half the user's step frequency, or greater than a maximum between a threshold (e.g. 2 Hz) and the user's step frequency, or greater than the user's step frequency, or any other and/or any variations and/or combinations thereof); in some embodiments, the expression "chosen in terms of the user's step frequency" for an update frequency may comprise any case in which the update frequency is greater than the user's step frequency, and this may be applicable to the update frequency of determining the gait characteristic and/or to the update frequency of controlling an aspect of the application with the determined gait characteristic, even if both update frequencies are different, and/or they are unrelated and/or they are related and/or they are are the same, while in some embodiments, any variations and/or combinations thereof may also be possible. In some embodiments, both update frequencies (determining and controlling) may be the same, and lower than an accelerometer (of the device, and which may have been leveraged for the determination of the gait characteristic) sampling rate. In some embodiments, the controlling of an aspect of the application with the gait characteristic may be enabled after another gait characteristic of the user has been determined; for example, the controlling of the user's representation's velocity with the determined user's velocity, may be enabled after an activity (e.g. walking, or running, or standing still, or any other type of activity and/or movement) of the user has been recognized; in some embodiments, the controlling of an aspect of the application with the gait characteristic may be controlled in any way by/with another gait characteristic (or other gait characteristic) of the user; or in some embodiments, the controlling (with an update frequency larger than the user's step frequency (or any other)) of an aspect of the application may be performed with a plurality of gait characteristics of the user, which may be determined simultaneously and with an update frequency larger than the user's step frequency (or any other); for example, if the user's velocity is 3 mph, and/or the user's cadence is 2 Hz, and/or the user's step length is 67 cm (or stride length is 134 cm), and/or the calories burned per time unit are 280 calories/hour, and/or the user's activity is "walking", and/or the user's device position is "in pocket", and/or the user's status of a medical condition is "healthy", then the user's representation's neck skin color may be set to pink; however, if the user's velocity is 2 mph, and/or the user's cadence is 1.8 Hz, and/or the user's step length is 50 cm (or stride length is 100 cm), and/or the calories burned per time unit are 190 calories/hour, and/or the user's activity is "walking", and/or the user's device position is "in hand", and/or the user's status of a medical condition is "unhealthy", then the user's representation's neck skin color may be set to a pale color; but, if in this last case, the user's activity changes to e.g. "walking in an inclined plane", the user's representation's neck skin color may be set to a reddish tone (e.g. to reflect bigger effort); or for example, if the user's representation's face skin color is set to white for values of the user's velocity below 3 mph, this may be changed if the determined/recognized activity of the user changes e.g. from "walking" to "jogging" while keeping the same velocity range (e.g. the user's representation's face skin color may be set to pink to reflect higher level of exercise when the activity is jogging, but said color may be set to white, for the same range of velocities, when the activity is walking); in some embodiments, we may be determining several gait characteristics (any or all or any subset and/or combination of any of the referred gait characteristics) simultaneously (e.g. with an update frequency larger than the user's step frequency, or any other), and control an aspect (or several aspects, such as the user's representation's face skin color and/or texture, and/or the user's representation's neck skin color and/or texture, etc.) of an application with any or all or a subset of the determined gait characteristics; additionally, in some embodiments the user's representation may be displayed on the device screen (and/or in any other screen and/or in any virtual environment and/or in any other way) simultaneously with a dashboard element indicating the determined user's gait characteristic (and/or any other measurement related to any type of variable/characteristic such as glucose, and/or heart rate, and/or blood pressure, and/or any other and/or any variations and/or combinations thereof); and in some embodiments, an aspect of an application (including the controlling of an aspect of the application with a determined user's gait characteristic(s)) may be controlled with the recognition that the user's gait activity has started/stopped/changed (e.g. the time instant at which the user stops walking, and e.g. stands still or starts jogging, may be recognized, and used in any way, e.g. to display a message or deliver an acoustic message conveying the user that the start/change/stop in the activity has been recognized, and/or to control in any way how an aspect of the application is controlled by a determined gait characteristic (e.g. if the user's representation's velocity on the device screen (in millimeters/second) is set to the value of the determined user's velocity (in miles per hour) while the user's activity is walking, we may change that relationship (e.g. doubling it) when the user's activity changes from walking to running)).

And following with examples of embodiments, the controlling of an aspect of an application with the determined user's gait characteristic may be enabled leveraging a recognized gait activity of the user (e.g. said controlling may be enabled only after the user's activity is recognized as walking, or said controlling may be enabled only after a transition in the user's activity from standing still to walking has been recognized, etc.). And in some embodiments, the user is communicated to start a gait activity until said activity is recognized, while the determining of the gait velocity and the recognizing of the gait activity continue; for example, we may continuously determine the user's gait characteristic and determine/recognize the user's gait activity (which may be e.g. standing still), and until said recognized activity doesn't change from standing still to walking, we may communicate the user to please start walking, and only after the walking activity is recognized, enable the controlling with the gait characteristic; and/or for example, we may continuously determine the user's gait characteristic and determine/recognize the user's gait activity/movement (which may be e.g. any shake and/or any activity and/or any movement different from holding the device still, and/or any other and/or any variations), and we may communicate the user (e.g. acoustic message and/or displaying text on the screen and/or any other way) to hold the device still, until it is recognized that the device is still (e.g. determining that the user's activity or movement is still, and/or by determining that the user's device accelerometer's standard deviation has dropped below a threshold (e.g. 0.7 or any other value that may be selected empirically), and/or by determining that any motion sensors in the device indicate a still condition, and/or any other way). In some embodiments, we may enable the controlling of an aspect of an application with the determined gait characteristic(s) only after the recognition that the device has been held still for a threshold amount of time; for example, we may display a message on the device screen communicating the user to please hold the device still, and keep recognizing the user's activity and determining the user's gait characteristic(s), but only enable the controlling of an aspect of an application with the determined gait characteristic(s) after the recognition that the device has been held still for a threshold amount of time (e.g. 2 seconds or any other selected amount), and at that point, we may end the displaying of the message on the device screen, and enable the controlling of an aspect of an application with the determined gait characteristic(s) (e.g. we may display a virtual environment showing a representation of the user, wherein the gait characteristic(s) of said representation are controlled with the determined gait characteristic(s) of the user). And in some embodiments, the application represents a virtual environment including a representation of the user, and the representation of the user can interact with one or more elements in the virtual environment, and the user participates in a networking environment with other users, and shares a same representation with the other users also represented in the virtual environment (e.g. the user's representation may represent a human being, and the other users' representations may also represent a human being, or the user's representation may represent a car, and the other users' representations may also represent a car (in some embodiments, it may be a different type of car, but still a car), etc.), while in some embodiments, one or more of the other users also represented in the virtual environment, are represented with a different representation (e.g. the user's representation may represent a human being, and one or more of the other users' representations may represent a car, or the user's representation may represent a car, and one or more of the other users' representations may represent a motorcycle, etc.), while in some embodiments, the virtual environment further includes one or more dashboard elements indicating the gait characteristic(s) of the users' representation(s) and/or the determined gait characteristic(s) of the users and/or any other indication (e.g. glucose level, any heart related information such as heart rate, blood pressure, and/or any other) relative to the users and/or their representations, while in some embodiments, any variations and/or combinations thereof are also possible.

It is interesting to note that throughout this specification, the user's velocity, and/or activity and/or stride length, and/or calories burned per time unit, and/or device position, and/or any other gait (or any other type) characteristic (that may be used to control one or more attributes of a user's representation, or to control a user's representation, or to control an aspect of an application, etc.), may be determined in some embodiments by a machine learning algorithm (e.g. support vector machine, random forests, neural networks, decision tree, logistic regression, etc. and/or any other and/or any variations and/or combinations thereof) that leverage the user's cadence (e.g. as a feature, or as input, etc.). For example, by applying a machine learning algorithm, some embodiments may determine a model (e.g. a mathematical model and/or a mathematical relationship and/or a formula and/or a structure of conditionals and/or any other and/or any variations and/or combinations thereof) that may include the determined user's gait cadence (or any other attributes) as inputs. By way of example without limitation, any approaches such as those described in application Ser. No. 16/044,833 for the modeling of a medical condition (or any other characteristic of the mobile or wearable device user) may be used in some embodiments for the modeling of the user's velocity, and/or activity and/or stride length, and/or calories burned per time unit, and/or device position, and/or any other. By way of example without limitation, simplistic (for clarity purposes) examples of models may include in some embodiments: velocity=$c\_v\_1$*cadence+$c\_v\_2$*feature_2+$c\_v\_3$*feature_3+$c\_v\_4$*feature_4; activity=$c\_a\_1$*cadence+$c\_a\_2$*feature_2+$c\_a\_3$*feature_3+$c\_a\_4$*feature_4; stride length=$c\_s\_1$*cadence+$c\_s\_2$*feature_2+$c\_s\_3$*feature_3+$c\_s\_4$*feature_4; calories burned per time unit=$c\_c\_1$*cadence+$c\_c\_2$*feature_2+$c\_c\_3$*feature_3+$c\_c\_4$*feature_4; device position=$c\_p\_1$*cadence+$c\_p\_2$*feature_2+$c\_p\_3$*feature_3+$c\_p\_4$*feature_4. Wherein cadence may refer to the determined user's gait cadence (as determined by any of the approaches described in this specification or any other), with typical values ranging from approximately 0.3 Hz to approximately 2.35 Hz if the user is walking, or ranging from approximately 2.3 Hz to approximately 6 Hz if the user is running, etc.; wherein feature_2, feature_3, feature_4, and/or any others may be features of the device user (e.g. any determined gait (or any other type) characteristic, e.g. a step count and/or a gait irregularity factor, and/or velocity, and/or activity and/or stride length, and/or calories burned per time unit, and/or device position, and/or distance and/or temperature, and/or humidity, and/or any others and/or any variations and/or combinations thereof) and/or any type of feature/measurement/input obtained/determined by any means (e.g. an accelerometer mean, and/or standard deviation, and/or kurtosis and/or main frequency components, etc. e.g. determined over a time window of e.g. 4 or any other seconds) and/or any others and/or any variations and/or combinations thereof; and wherein $c\_v\_1$, $c\_v\_2$, $c\_v\_3$, $c\_v\_4$, $c\_a\_1$, $c\_a\_2$, $c\_a\_3$, $c\_a\_4$, $c\_s\_1$, $c\_s\_2$, $c\_s\_3$, $c\_s\_4$, $c\_c\_1$, $c\_c\_2$, $c\_c\_3$, $c\_c\_4$, $c\_p\_1$, $c\_p\_2$, $c\_p\_3$, $c\_p\_4$ and/or any others are coefficients (e.g. any real numbers (e.g. 0.4, 1.24, 2.3, −0.7, etc.), or any kind of term and/or mathematical relationship of any kind). It is interesting to note that, by way of example without limitation, velocity may be measured in miles per hour (e.g. 3 mph, 1.5 mph, 5 mph), km/h or any other units; activity may be coded to reflect different activities (e.g. 0 for walking, 1 for running, etc.; and/or any value below 0.5 for walking, and/or any value between 0.5 and 1.5 for running, etc. and/or any variations and/or combinations thereof); stride length may be measured in cm (e.g. 30 cm, 50 cm, 75 cm), inches or any other units; calories burned per time unit may be measured in Calories per hour (e.g. 200 Calories per hour, 300 Calories per hour, 500 Calories per hour), Calories per second, etc. or any other units; device position may be coded to reflect different position of the mobile or wearable device relative to the user's body (e.g. 4 for pocket, 3 for hand, etc.; and/or any value between 3.5 and 4.5 for pocket, and/or any value between 2.5 and 3.5 for hand, etc. and/or any variations and/or combinations thereof). It is interesting to note that the machine learning algorithm(s) used for modelling any of the referred characteristics (gait or any other type) may use training set(s) containing cadence values (e.g. as explained in application Ser. No. 16/044,833) and device position; for example, a training set may be composed of lines of comma separated values such as 2, 3.5, 0, 4, 10.2, . . . etc. (e.g. cadence of 2 Hz, velocity of 3.5 mph, activity of 0 (code for walking), device position of 4 (code for pocket), mean of accelerometer x axis of 10.2 m/s^2, . . . etc.), where said values may have been computed for the device user and/or other users (e.g. determining values in real time while the user(s) perform actions on which to train the algorithm(s) (please see application Ser. No. 16/044,833 for more details on this and other topics)). It is interesting to note that any other simpler and/or more complex structures (including additional terms and/or coefficients and/or operands and/or conditionals and/or inputs and/or any others and/or any variations and/or combinations thereof) may be used in some embodiments.

In some embodiments, the user's representation is composed of at least a threshold number of movable parts. As used herein, the term "movable part" refers to an element of the user's representation which can perform a movement relative to the center of mass of the user's representation; for example, considering the center of mass of the user's representation to be placed approximately by the hip (e.g. please see FIG. 12 with a circle positioned approximately by the hip), movable parts are the elements of the user's representation that can perform a translation and/or rotation movement relative to said center of mass, such as: head, neck, shoulders, arms, hands, fingers, back, legs, feet, etc; focusing again on FIG. 12 which illustrates an X-ray type of representation showing bones (straight lines terminated in small circles) corresponding to each movable part of the user's representation, said bones may be used to control the movable parts associated to them (e.g. movements of the bones will result in movements of the movable parts associated to them); in the user's representation shown in FIG. 12 there are about 70 bones, each associated to a movable part (e.g. each hand has several bones for each finger, and each one of them is a movable part because they can perform a movement relative to the center of mass (hip)); some embodiments may leverage user's representations with at least a threshold number of bones, or a threshold number of movable parts, wherein said threshold may be larger than 2 (e.g. said threshold may be any number above 2, such as 3, 4, 5, 10, 20, 50, or even larger than 70, such as 100, 150, or even larger than 200 if we want to have a very detailed control over many movable parts). For example, FIG. 9D shows 26 frames corresponding to a whole gait cycle of the user's representation (clearer details of a few of said frames can be observed in FIG. 10D, which was created leveraging Blender (please see FIG. 12 for a more detailed view)), and at each one of the 26 frames of FIG. 9D (or any other), most of the approximately 70 movable parts composing the user's representation (e.g. each foot has 2 movable parts, as seen in FIG. 12 showing 2 bones (straight lines ending in small circles) for each foot, where each bone controls the volume of the user's representation associated with (around) the bone, and for instance, the small bone at the end of the foot controls the fingers area/volume and the large bone at the back of the foot controls the heel area/volume; each leg has 2 bones (2 movable parts); each hand has 5 movable fingers and each finger has 3 or 4 movable parts (bones), etc.) were controlled; in other words, at each one of the 26 frames of FIG. 9D, most of the approximately 70 movable parts composing the user's representation were made to perform a movement relative to the center of mass of the user's representation, and said movements involved changes in transform related attributes (e.g. location and/or rotation) of each one of the controlled movable parts (i.e. those that were made to perform a movement; i.e. most of the approximately 70 movable parts); consequently, some embodiments may control one or more attributes of a threshold number of elements of the user's representation with the determined velocity and/or cadence and/or stride-length and/or activity and/or device position and/or calories burned per time unit and/or status of a medical condition and/or step count and/or any other in real time and independently, and wherein said threshold number of elements is greater than 2; in some embodiments said threshold number of elements (e.g. movable parts) may be greater than 10, 14, 20, 30, 50, 70, or even greater than 200, or any other number (depending e.g. on the level of detail we want to control and the hardware and/or software specifications of the device); in other words, some embodiments may control a user's representation with the determined gait velocity in real time, wherein the user's representation is composed of at least twenty movable parts; and in some embodiments, the controlling comprises controlling independently one or more attributes of at least fourteen (or more) elements of the user's representation, with the determined gait velocity in real time; and in some embodiments, the controlled attributes vary as a function of the determined gait velocity and while the user performs a same type of activity; for example, a range of a rotation of a user's representation's movable part (e.g. head and/or shoulders and/or back and/or hip and/or arms and/or hands and/or any fingers and/or legs and/or feet and/or any others) may vary in real time as a function of the determined velocity (and independently for each one of the movable parts (e.g. if movable part=head, then range of a rotation is proportional to 1.1*velocity; if movable part=shoulders, then range of a rotation is proportional to 0.9*velocity; if movable part=back, then range of a rotation is proportional to 1.2*velocity; if movable part=hip, then range of a rotation is proportional to 0.6*velocity; if movable part=right arm, then range of a rotation is proportional to 2.1*velocity; if movable part=left arm, then range of a rotation is proportional to 2.0*velocity; if movable part=right hand, then range of a rotation is proportional to 0.8*velocity; if movable part=left hand, then range of a rotation is proportional to 0.75*velocity; if movable part=right hand thumb finger, then range of a rotation is proportional to 0.3*velocity; etc.)) and while in a same activity (e.g. a range of a rotation of the head and/or shoulders and/or back and/or hip and/or arms and/or hands and/or fingers and/or legs and/or feet and/or any others, in synchronism with the user's footsteps, and while the activity is walking, may be 5.5 degrees when the velocity is 4 mph, 4.3 degrees when the velocity is 3 mph, be 3.1 degrees when the velocity is 2 mph, etc.; and when the activity is running, the range be 8 degrees when the velocity is 6 mph, 9 degrees when the velocity is 7 mph, etc.); please note that the range of rotation of these examples may apply to any of the rotations of any movable parts described throughout this specification (e.g. any of the described movements of any of the user's representation's movable parts in synchronism with the user's footsteps); and analogous reasoning can be applied to any other types of movements (besides rotation). It is interesting to note that a rigid representation of a user does not have movable parts; for example, a foot in a rigid representation can not be considered a movable part (even if the rigid representation can perform any translation and/or rotation movement); similarly, a rigid upper body including the center of mass can not be considered a movable part even if the rigid upper body can perform any translation and/or rotation movement; similarly, a foot moving rigidly within a leg that can perform a movement relative to the center of mass, can not be considered a movable part different from said leg (the leg that can perform the movement relative to the center of mass is a movable part that includes everything that moves rigidly with it; in other words, the leg, including everything that moves rigidly with it (e.g. foot), is one movable part); regarding a user's representation's hair, if it can perform a movement relative to the center of mass (as shown e.g. in FIGS. 10E & 10F), it is considered one movable part, even if it is composed of multiple hairs/strands/filaments/parts.

Regarding the one or more attributes of a user's representation that can be controlled in real time with a determined gait characteristic (e.g. in synchronism with the user's feet landing on a ground), we can distinguish between transform related attributes and non transform related attributes. As used herein, the term "transform related attributes" refers to the location coordinates (e.g. three-dimensional x, y, z location coordinates) defining the location/position of an element (e.g. defining the location of an edge of the element (e.g. a joint (e.g. a small circle at the edge of a bone as shown in FIG. 12) of the bone associated with the element), or the location of the middle point of the element, or in other ways) of the user's representation, and/or the rotational information (e.g. Euler angles or quaternion information) defining the rotation/angles of an element (or the bone associated with the element) of the user's representation, and/or the scaling factors (e.g. three-dimensional x, y, z scaling factors as shown in FIG. 12) defining the scaling (change of size) of an element of the user's representation. For example, transform related attributes for the hip bone (associated with the hip of the user's representation) can be seen in FIG. 12, on the right hand side, under the label "Transform": location xyz, rotation wxyz, scale xyz. Attributes directly derived from the referred transform related attributes (e.g. a velocity, a maximum displacement of a foot in the horizontal direction (because it may be directly derived from the changes in location and rotation coordinates of the foot), etc.) are also transform related attributes. As used herein, the term "non transform related attributes" refers to attributes or properties of an element that are not "transform related attributes"; for example, the color (e.g. red or blue or green) and/or texture and/or material, etc. of an element.

Consequently, in some embodiments, we can control one or more transform related attributes and/or one or more non transform related attributes of one or more elements (including one or more movable parts) of the user's representation with the determined velocity and/or cadence and/or stride-length and/or activity and/or device position and/or calories burned per time unit and/or status of a medical condition and/or step count and/or any other and/or any variations and/or combinations thereof in real time (and independently), and while one or more elements (including movable parts such as hair, head, shoulders, back, feet, arms, legs, hands, fingers, etc.) of the user's representation move (or perform a movement) in synchronism with the user's footsteps (or in synchronism with the user's feet landing on a ground); and all this (or any variations and/or combinations thereof) may happen while the controlling is performed as described at least in the current specification and/or while the determination of the gait (or any other type) characteristic(s) is performed as described at least in the current specification. And all this may happen while changes of one or more controlled attributes (wherein said attributes may be transform related attributes and/or non transform related attributes) of three or more (e.g. fourteen or more) elements (wherein said elements may be movable parts and/or any other type) of the user's representation are shown/controlled/performed continuously and with an update period that is a function of the user's step period: e.g. an update period of about twice the user's gait period (e.g. inverse of the determined gait cadence), divided by a threshold number, and wherein said threshold number is greater than 3 in some embodiments (or greater than 10 or 20 or 30 or 40 in other embodiments); consequently, in some embodiments, said update period is a function of the user's gait period, and shorter than the user's gait period; and in some embodiments, said update period (of about twice the user's gait period, divided by a threshold number) may be different from the device's frame/screen refresh period. For example, considering a frame by frame animation leveraging e.g. the 26 frames of FIG. 9D or any other, with every consecutive frame, we are changing one or more attributes (e.g. transform related attributes such as the x, y, z location of e.g. the right foot and/or the left foot and/or the right hand and/or the left hand, etc. as shown in FIG. 9D, and we could also change non transform related attributes such as the skin color of the face, the skin color of the neck, the skin color of the right hand, etc.) of three or more elements (e.g. movable parts such as right hand, left hand, right foot, left foot, neck, etc., or any other type of elements) of the user's representation, in a continuous manner (e.g. frames may be displayed consecutively in a cyclic way (0, 1, 2, . . . 24, 25, 0, 1, 2 . . . ) and continuously on the device screen), and with an update period of about twice the user's gait period (e.g. about twice the inverse of the determined gait cadence), divided by a threshold number (e.g. the number of frames, in this example, 26). The update period (time interval) for the changes to be shown is approximately the time interval between a frame being shown and the next frame being shown; for example, if frame 0 starts being displayed at time instant 0:00:00 hour:minutes:seconds and 000 milliseconds, and frame 1 starts being displayed (after frame 0) at time instant 0:00:00 hour:minutes:seconds and 038 milliseconds, the time interval of 038 milliseconds between consecutive frames is the update period (time interval) for the changes to be shown; and said update period (time interval) may be selected/chosen as about twice (please remember that a whole gait cycle represented with e.g. 26 frames of FIG. 9D spans about 2 gait periods) the user's gait period (e.g. about twice the inverse of the determined gait cadence), divided by the number of frames (e.g. 26 in FIG. 9D); for example, if the determined user's gait cadence is 2 Hz, the update period (time interval) for the changes to be shown is about 2*(0.5 seconds)/26~=038 milliseconds; for example, if the determined user's gait cadence is 1 Hz, the update period (time interval) for the changes to be shown is about 2*(1 second)/26~=077 milliseconds; and the update period (time interval) for the changes to be shown may be different from the device's frame (or screen) refresh period; for example, if the device's frame/screen refresh period is 019 milliseconds (e.g. refresh rate of approximately 52 Hz), and we are changing our user's representation's frames every 038 milliseconds, we may repeat our user's representation's frames every other time the device screen is refreshed, in order to keep refreshing the device screen every 019 milliseconds, but only showing a new frame of the user's representation every 038 milliseconds. It is interesting to note that some embodiments may use a number of frames different from 26, so the previously mentioned threshold number can be different from 26; for example, some embodiments may use 3 frames for the user's representation, or 10 or more frames, or 20 or more frames, or 30 or more frames, or 40 or more frames, etc. (some embodiments may select said number depending on the hardware and/or software specifications of the mobile or wearable device). It is interesting to note that some embodiments may apply any of these descriptions for changes of one or more attributes, wherein said changes are different from any change affecting the whole user's representation equally (e.g. if a rigid representation of a user is moved, the changes due to the movement affect the whole user's representation equally); as used herein, the term "change affecting the whole user's representation equally" refers to any change, such as any modification of any transform related attributes and/or non transform related attributes that is applied to the user's representation as a whole, or to the center of mass of the user's representation and affects the whole user's representation; for example, a translation and/or rotation movement of a rigid representation of a user affects the representation as a whole, and thus it is a change affecting the whole user's representation equally. And all this may happen while controlling one or more attributes of a threshold number of elements of the user's representation in real time and independently, and wherein said threshold number of elements is greater than 2 (e.g. 70 or any other number). And in some embodiments, one or more attributes of three or more elements of the user's representation are controlled with, and vary as a function of, the determined gait velocity (and/or stride length and/or cadence and/or calories burned per time unit and/or activity and/or device position and/or status of a medical condition and/or steps count and/or any other) in real time and independently, and while the user performs a same type of activity. For example, the xyz location coordinates of a movable part (e.g. right hand) of the user's representation may be controlled as shown in FIG. 9A (clearer details shown in FIG. 10A) for a velocity of e.g. 1 mph during a walking activity; however, if the user increases velocity to e.g. 2 mph (while performing the same walking activity), the right hand of the user's representation may be controlled as shown in FIG. 9B (clearer details shown in FIG. 10B), just by changing the frames strip file as described in other paragraphs; if the user increases velocity to e.g. 2.75 mph (while performing the same walking activity), the right hand of the user's representation may be controlled as shown in FIG. 9C (clearer details shown in FIG. 10C); if the user increases velocity to e.g. 3.5 mph (while performing the same walking activity), the right hand of the user's representation may be controlled as shown in FIG. 9D (clearer details shown in FIG. 10D), etc. Some embodiments may use any other numbers, quantities, approaches, methodologies, techniques, and/or any others, and/or any variations and/or combinations thereof, including of any of the descriptions throughout the whole of this specification and/or any incorporated references.

Although the foregoing text sets forth a detailed description of numerous different embodiments of the invention, it should be understood that the scope of the invention is defined by the words of the claims set forth at the end of this patent. The detailed description is to be construed as exemplary only and does not describe every possibly embodiment of the invention because describing every possible embodiment would be impractical, if not impossible. Numerous alternative embodiments could be implemented, using either current technology or technology developed after the filing date of this patent, which would still fall within the scope of the claims defining the invention.

Thus, many modifications and variations may be made in the techniques and structures described and illustrated herein without departing from the spirit and scope of the present invention. Accordingly, it should be understood that the methods and apparatus described herein are illustrative only and are not limiting upon the scope of the invention.

The invention claimed is:

1. A method comprising:
   determining a gait velocity of a user of a mobile or wearable device in real time as the gait velocity occurs; wherein the mobile or wearable device is carried by the user; and
   controlling, in real time as the gait velocity occurs, a user's representation in the mobile or wearable device with the determined gait velocity; wherein the user's representation is composed of at least seventy movable parts; and wherein the controlling comprises:
   controlling, in real time as the gait velocity occurs, one or more attributes of at least fifty of said movable parts of the user's representation with the determined gait velocity.

2. The method of claim 1, further comprising:
   determining a footstep of the user in real time as the footstep occurs; and
   using said footstep to synchronize a head movement of the user's representation with said footstep; wherein the head movement comprises a cyclical rotation.

3. A method comprising:
   determining a gait velocity of a user of a mobile or wearable device in real time as the gait velocity occurs; wherein the mobile or wearable device is carried by the user;
   controlling, in real time as the gait velocity occurs, a user's representation in the mobile or wearable device with the determined gait velocity; wherein the user's representation is composed of at least three movable parts; and
   controlling, in real time as the gait velocity occurs, a position of a frame on a screen of the mobile or wearable device with the determined gait velocity.

4. The method of claim 3, further comprising:
   determining a footstep of the user in real time as the footstep occurs; and
   using said footstep to synchronize a head movement of the user's representation with said footstep; wherein the head movement comprises a cyclical rotation.

5. The method of claim 3, wherein the gait velocity is determined with an update frequency greater than a step frequency of the user and less than a sampling rate of an accelerometer of the mobile or wearable device.

6. The method of claim 3, wherein the frame shows the user's representation.

7. The method of claim 3, wherein the frame shows a representation different from the user's representation.

8. A method comprising:
   determining a gait velocity of a user of a mobile or wearable device in real time as the gait velocity occurs; wherein the mobile or wearable device is carried by the user; and
   controlling, in real time as the gait velocity occurs, a user's representation in the mobile or wearable device with the determined gait velocity; wherein the controlling comprises:
   controlling an attribute of the user's representation with the determined gait velocity;
   wherein the attribute varies with the determined gait velocity by following a mathematical relationship which relates the attribute and the determined gait velocity.

9. The method of claim 8, further comprising:
   determining a footstep of the user in real time as the footstep occurs; and
   using said footstep to synchronize a head movement of the user's representation with said footstep; wherein the head movement comprises a cyclical rotation.

10. The method of claim 8, wherein the gait velocity is determined with an update frequency greater than a step frequency of the user and less than a sampling rate of an accelerometer of the mobile or wearable device.

11. The method of claim 8, wherein the attribute is different from a velocity.

12. The method of claim 8, wherein the mathematical relationship uses a multiplication.

13. The method of claim 8, wherein the user's representation is composed of at least three movable parts, the method further comprising: controlling, in real time as the gait velocity occurs, an aspect of an application in the mobile or wearable device with the determined gait velocity; wherein the aspect of the application is different from the user's representation.

14. The method of claim 8, wherein the user's representation is composed of at least three movable parts, the method further comprising: controlling, in real time as the gait velocity occurs, a representation with the determined gait velocity; wherein the representation is different from the user's representation.

15. The method of claim 8, further comprising:
   determining a gait cadence of the user in real time as the gait cadence occurs; and controlling, in real time as the gait cadence occurs, one or more attributes of the user's representation with the determined gait cadence.

16. The method of claim 8, further comprising:
recognizing a gait activity of the user in real time as the gait activity occurs by leveraging a machine learning algorithm; and
controlling a gait activity of the user's representation with the recognized gait activity of the user; wherein the gait activity of the user is recognized from a set comprising a walking activity and a running activity.

17. The method of claim 16, further comprising:
determining a footstep of the user in real time as the footstep occurs; and
using said footstep to synchronize a head movement of the user's representation with said footstep; wherein the head movement comprises a cyclical rotation.

18. A method comprising:
determining a gait activity of a user of a mobile or wearable device in real time as the gait activity of the user occurs; wherein the mobile or wearable device is carried by the user; and
controlling, in real time as the gait activity of the user occurs, a user's representation in the mobile or wearable device with the determined gait activity of the user; wherein the user's representation is composed of at least three movable parts;
wherein the determining comprises: recognizing the gait activity of the user by leveraging a machine learning algorithm; and wherein the controlling comprises: controlling a gait activity of the user's representation with the recognized gait activity of the user; wherein the gait activity of the user is recognized from a set comprising: a walking activity, and a running activity.

19. The method of claim 18, further comprising:
determining a footstep of the user in real time as the footstep occurs; and
using said footstep to synchronize a head movement of the user's representation with said footstep; wherein the head movement comprises a cyclical rotation.

20. The method of claim 18, wherein the gait activity of the user is determined with an update frequency greater than an upper edge of a frequency band of the gait activity of the user and less than a sampling rate of an accelerometer of the mobile or wearable device.

21. The method of claim 18, wherein the gait activity of the user is determined with an update frequency greater than a step frequency of the user and less than a sampling rate of an accelerometer of the mobile or wearable device.

22. The method of claim 18, further comprising:
determining a gait cadence of the user in real time as the gait cadence occurs; and
controlling, in real time as the gait cadence occurs, one or more attributes of the user's representation by using the determined gait cadence.

23. The method of claim 22, further comprising:
determining a footstep of the user in real time as the footstep occurs; and
using said footstep to synchronize a head movement of the user's representation with said footstep; wherein the head movement comprises a cyclical rotation.

24. The method of claim 18, further comprising:
determining a length of a gait step of the user in real time as the gait step of the user occurs; and
controlling, in real time as the gait step of the user occurs, a length of a gait step of the user's representation with the determined length of the gait step of the user; wherein the mobile or wearable device is a smartphone.

25. The method of claim 24, further comprising:
determining a footstep of the user in real time as the footstep occurs; and
using said footstep to synchronize a head movement of the user's representation with said footstep; wherein the head movement comprises a cyclical rotation.

26. The method of claim 18, further comprising: controlling, in real time as the gait activity of the user occurs, an aspect of an application in the mobile or wearable device with the determined gait activity of the user; wherein the aspect of the application is different from the user's representation.

27. A method comprising:
determining a length of a gait step of a user of a mobile or wearable device in real time as the gait step of the user occurs; wherein the mobile or wearable device is carried by the user;
determining, by using the determined length of the gait step of the user, a distance travelled by the user; and
controlling, in real time as the gait step of the user occurs, a user's representation in the mobile or wearable device with the determined length of the gait step of the user;
wherein the user performs at least a complete gait cycle comprising the gait step of the user and another gait step of the user; wherein the controlling comprises: controlling a length of a gait step of the user's representation with the determined length of the gait step of the user.

28. The method of claim 27, further comprising:
determining a footstep of the user in real time as the footstep occurs; and
using said footstep to synchronize a head movement of the user's representation with said footstep; wherein the head movement comprises a cyclical rotation.

29. A method comprising:
determining a length of a gait step of a user of a mobile or wearable device in real time as the gait step of the user occurs; wherein the mobile or wearable device is carried by the user; and
controlling, in real time as the gait step of the user occurs, a user's representation in the mobile or wearable device with the determined length of the gait step of the user;
wherein the user performs a gait activity selected from a set consisting of: a walking activity, a jogging activity, and a running activity; wherein the controlling comprises: controlling a length of a gait step of the user's representation with the determined length of the gait step of the user.

30. The method of claim 29, further comprising:
determining a footstep of the user in real time as the footstep occurs; and
using said footstep to synchronize a head movement of the user's representation with said footstep; wherein the head movement comprises a cyclical rotation.

31. The method of claim 30, wherein the mobile or wearable device is a wearable device worn on a wrist of the user.

32. The method of claim 30, wherein the mobile or wearable device is a wearable device worn: on a face of the user, and/or on a head of the user.

33. A method comprising:
determining a length of a gait step of a user of a mobile or wearable device in real time as the gait step of the user occurs; wherein the mobile or wearable device is carried by the user; and controlling, in real time as the gait step of the user occurs, a user's representation in the mobile or wearable device with the determined length of the gait step of the user;

wherein the user travels from a place to a different place; wherein the controlling comprises:

controlling a length of a gait step of the user's representation with the determined length of the gait step of the user.

34. The method of claim 33, further comprising:

determining a footstep of the user in real time as the footstep occurs; and using said footstep to synchronize a head movement of the user's representation with said footstep; wherein the head movement comprises a cyclical rotation.

35. A method comprising:

determining a length of a gait step of a user of a mobile or wearable device in real time as the gait step of the user occurs; wherein the mobile or wearable device is carried by the user; and controlling, in real time as the gait step of the user occurs, a user's representation in the mobile or wearable device with the determined length of the gait step of the user;

wherein the mobile or wearable device is a smartphone; wherein the controlling comprises:

controlling a length of a gait step of the user's representation with the determined length of the gait step of the user.

36. The method of claim 35, further comprising:

determining a footstep of the user in real time as the footstep occurs; and using said footstep to synchronize a head movement of the user's representation with said footstep; wherein the head movement comprises a cyclical rotation.

37. A method comprising:

determining a length of a gait step of a user of a mobile or wearable device in real time as the gait step of the user occurs; wherein the mobile or wearable device is carried by the user; and controlling, in real time as the gait step of the user occurs, a user's representation in the mobile or wearable device with the determined length of the gait step of the user;

wherein a first gait cycle comprising the gait step of the user and another gait step of the user, is emulated by the user's representation with a second gait cycle of two gait steps of the user's representation in real time as the first gait cycle occurs.

38. The method of claim 37, further comprising:

determining a footstep of the user in real time as the footstep occurs; and using said footstep to synchronize a head movement of the user's representation with said footstep; wherein the head movement comprises a cyclical rotation.

39. The method of claim 37, wherein the second gait cycle comprises at least 3 different postures.

40. The method of claim 37, wherein a length of at least one of the two gait steps of the user's representation, is controlled with the determined length of the gait step of the user.

41. A method comprising:

determining a gait cadence of a user of a mobile or wearable device in real time as the gait cadence occurs; wherein the mobile or wearable device is carried by the user; and controlling, in real time as the gait cadence occurs, a user's representation in the mobile or wearable device with the determined gait cadence;

wherein the controlling comprises: selecting a frame by using the determined cadence.

42. The method of claim 41, wherein the frame shows a posture of the user's representation; wherein a gait cycle of the user's representation is composed of at least three different postures.

43. The method of claim 42, further comprising:

determining a footstep of the user in real time as the footstep occurs; and using said footstep to synchronize a head movement of the user's representation with said footstep; wherein the head movement comprises a cyclical rotation.

44. A method comprising:

determining a gait cadence of a user of a mobile or wearable device in real time as the gait cadence occurs; wherein the mobile or wearable device is carried by the user;

controlling, in real time as the gait cadence occurs, a user's representation in the mobile or wearable device with the determined gait cadence; and controlling an aspect of an application with the determined gait cadence; wherein the aspect is different from the user's representation.

45. The method of claim 44, further comprising:

determining a footstep of the user in real time as the footstep occurs; and using said footstep to synchronize a head movement of the user's representation with said footstep; wherein the head movement comprises a cyclical rotation.

46. A method comprising:

determining a gait cadence of a user of a mobile or wearable device in real time as the gait cadence occurs; wherein the mobile or wearable device is carried by the user; and controlling, in real time as the gait cadence occurs, a user's representation in the mobile or wearable device with the determined gait cadence; wherein the controlling comprises:

controlling a time length of a gait cycle of the user's representation with the determined gait cadence; wherein the gait cycle comprises at least three different postures.

47. The method of claim 46, further comprising:

determining a footstep of the user in real time as the footstep occurs; and using said footstep to synchronize a head movement of the user's representation with said footstep; wherein the head movement comprises a cyclical rotation.

48. A method comprising:

determining a gait cadence of a user of a mobile or wearable device in real time as the gait cadence occurs; wherein the mobile or wearable device is carried by the user; and controlling, in real time as the gait cadence occurs, a user's representation in the mobile or wearable device with the determined gait cadence; wherein the controlling comprises:

controlling a time length of a frame with the determined gait cadence.

49. The method of claim 48, wherein the time length of the frame is controlled by leveraging: the determined cadence, and a total number of frames contained in a gait cycle of the user's representation.

50. The method of claim 49, further comprising:

determining a footstep of the user in real time as the footstep occurs; and using said footstep to synchronize a head movement of the user's representation with said footstep; wherein the head movement comprises a cyclical rotation.

51. A method comprising:
determining a gait cadence of a user of a mobile or wearable device in real time as the gait cadence occurs; wherein the mobile or wearable device is carried by the user; and
controlling, in real time as the gait cadence occurs, a user's representation in the mobile or wearable device with the determined gait cadence; wherein the user's representation is composed of at least three movable parts; wherein the controlling comprises: controlling one or more attributes of three or more of said movable parts of the user's representation with the determined gait cadence.

52. The method of claim 51, further comprising:
determining a footstep of the user in real time as the footstep occurs; and
using said footstep to synchronize a head movement of the user's representation with said footstep; wherein the head movement comprises a cyclical rotation.

53. The method of claim 51, further comprising: controlling, in real time as the gait cadence of the user occurs, a gait cadence of the user's representation with the determined gait cadence of the user.

54. A method comprising:
determining a gait attribute of a user of a mobile or wearable device in real time as the gait attribute occurs; wherein the mobile or wearable device is carried by the user;
controlling, in real time as the gait attribute occurs, a user's representation in the mobile or wearable device with the determined gait attribute;
determining a length of a gait step of the user in real time as the gait step of the user occurs; and
controlling an aspect of an application in the mobile or wearable device with the determined length of the gait step of the user, wherein the aspect of the application is different from the user's representation.

55. The method of claim 54, wherein the aspect comprises elements different from the user's representation; wherein the user's representation may step on said elements.

56. A method comprising:
determining a gait related information of a user of a mobile or wearable device in real time as the gait related information occurs; wherein the mobile or wearable device is carried by the user;
controlling, in real time as the gait related information occurs, a user's representation in the mobile or wearable device with the determined gait related information; wherein the user's representation is composed of at least three movable parts;
determining a footstep of the user in real time as the footstep of the user occurs; and
controlling, in real time as the footstep of the user occurs, an element different from the user's representation by using said footstep of the user; wherein the user's representation steps on said element.

57. The method of claim 56, further comprising:
using said footstep of the user to synchronize a head movement of the user's representation with said footstep of the user; wherein the head movement comprises a cyclical rotation.

58. The method of claim 57, wherein the gait related information is selected from a set consisting of: a gait velocity of the user, a gait activity of the user, a gait cadence of the user, and a length of a gait step of the user; wherein the gait activity of the user is selected from a set consisting of: a walking activity, a jogging activity, and a running activity.

59. A method comprising:
determining a gait related information of a user of a mobile or wearable device in real time as the gait related information occurs; wherein the mobile or wearable device is carried by the user; wherein a user's representation in the mobile or wearable device is composed of at least three movable parts; and
controlling, in real time as the gait related information occurs, independently one or more attributes of at least two of said movable parts with the determined gait related information.

60. The method of claim 59, further comprising:
determining a footstep of the user in real time as the footstep occurs; and
using said footstep to synchronize a head movement of the user's representation with said footstep; wherein the head movement comprises a cyclical rotation.

61. The method of claim 60, wherein the gait related information is selected from a set consisting of: a gait velocity of the user, a gait activity of the user, a gait cadence of the user, and a length of a gait step of the user; wherein the gait activity of the user is selected from a set consisting of: a walking activity, a jogging activity, and a running activity.

62. A method comprising:
determining a gait related information of a user of a mobile or wearable device in real time as the gait related information of the user occurs; wherein the mobile or wearable device is carried by the user; wherein a user's representation in the mobile or wearable device is composed of at least three movable parts;
controlling, in real time as the gait related information of the user occurs, the user's representation with the determined gait related information of the user;
determining a footstep of the user in real time as the footstep of the user occurs;
determining a time instant of the determined footstep of the user; and
using the determined time instant to synchronize a stepping of the user's representation with the footstep of the user, by assigning a frame at which the user's representation is shown stepping to the determined time instant of the footstep of the user.

63. The method of claim 62, further comprising:
using said footstep of the user to: synchronize a head movement of the user's representation with said footstep of the user; wherein the head movement comprises a cyclical rotation.

64. The method of claim 63, wherein the gait related information of the user is selected from a set consisting of: a gait velocity of the user, a gait activity of the user, a gait cadence of the user, and a length of a gait step of the user; wherein the gait activity of the user is selected from a set consisting of: a walking activity, a jogging activity, and a running activity.

65. The method of claim 62, wherein the synchronizing the stepping of the user's representation with the footstep of the user comprises: determining a frame number of a frame which should be displayed, by using a determined time distance and a total number of frames contained in one gait cycle of the user's representation;

wherein the frame which should be displayed comprises the frame at which the user's representation is shown stepping.

66. A method comprising:
   determining a gait attribute of a user of a mobile or wearable device in real time as the gait attribute of the user occurs; wherein the mobile or wearable device is carried by the user;
   wherein a user's representation in the mobile or wearable device is composed of at least three movable parts; and
   controlling, in real time as the gait attribute of the user occurs, the user's representation with the determined gait attribute of the user; wherein the controlling comprises: selecting a file which contains at least three images by using the determined gait attribute.

67. The method of claim 66, wherein each one of said images shows a different posture of the user's representation.

68. A method comprising:
   determining a gait attribute of a user of a mobile or wearable device in real time as the gait attribute of the user occurs; wherein the mobile or wearable device is carried by the user;
   wherein a user's representation in the mobile or wearable device is composed of at least three movable parts;
   controlling, in real time as the gait attribute of the user occurs, the user's representation with the determined gait attribute of the user; and
   controlling a scaling of a representation with the determined gait attribute of the user, wherein the representation is different from the user's representation.

69. The method of claim 68, further comprising:
   determining a footstep of the user in real time as the footstep occurs; and
   using said footstep to synchronize a head movement of the user's representation with said footstep; wherein the head movement comprises a cyclical rotation.

70. The method of claim 69, wherein the gait attribute is selected from a set consisting of: a gait velocity of the user, a gait activity of the user, a gait cadence of the user, and a length of a gait step of the user; wherein the gait activity of the user is selected from a set consisting of: a walking activity, a jogging activity, and a running activity.

71. The method of claim 68, wherein the gait attribute of the user is determined with an update frequency greater than a step frequency of the user and less than a sampling rate of an accelerometer of the mobile or wearable device.

72. A method comprising:
   determining a gait attribute of a user of a mobile or wearable device in real time as the gait attribute of the user occurs; wherein the mobile or wearable device is carried by the user;
   wherein a user's representation in the mobile or wearable device is composed of at least three movable parts; and
   controlling, in real time as the gait attribute of the user occurs, the user's representation with the determined gait attribute of the user; wherein the controlling comprises: controlling a scaling of the user's representation with the determined gait attribute of the user.

73. The method of claim 72, further comprising:
   determining a footstep of the user in real time as the footstep occurs; and
   using said footstep to synchronize a head movement of the user's representation with said footstep; wherein the head movement comprises a cyclical rotation.

74. The method of claim 73, wherein the gait attribute is selected from a set consisting of: a gait velocity of the user, a gait activity of the user, a gait cadence of the user, and a length of a gait step of the user; wherein the gait activity of the user is selected from a set consisting of: a walking activity, a jogging activity, and a running activity.

75. The method of claim 72, wherein the gait attribute of the user is determined with an update frequency greater than an upper edge of a frequency band of a gait activity of the user and less than a sampling rate of an accelerometer of the mobile or wearable device.

76. The method of claim 72, wherein the gait attribute of the user is determined with an update frequency greater than a step frequency of the user and less than a sampling rate of an accelerometer of the mobile or wearable device.

77. The method of claim 72, wherein the gait attribute is a velocity; the method further comprising:
   determining a gait cadence of the user in real time as the gait cadence of the user occurs; and
   controlling, in real time as the gait cadence of the user occurs, one or more attributes of the user's representation by using the determined gait cadence of the user.

78. A method comprising:
   determining a gait attribute of a user of a mobile or wearable device in real time as the gait attribute of the user occurs; wherein the mobile or wearable device is carried by the user;
   wherein a user's representation in the mobile or wearable device is composed of at least three movable parts; and
   controlling, in real time as the gait attribute of the user occurs, the user's representation with the determined gait attribute of the user; wherein a number of frames spanning a gait cycle of the user's representation is less than forty and greater than three.

79. The method of claim 78, further comprising:
   determining a footstep of the user in real time as the footstep occurs; and
   using said footstep to synchronize a head movement of the user's representation with said footstep; wherein the head movement comprises a cyclical rotation.

80. The method of claim 79, wherein the gait attribute is selected from a set consisting of: a gait velocity of the user, a gait activity of the user, a gait cadence of the user, and a length of a gait step of the user; wherein the gait activity of the user is selected from a set consisting of: a walking activity, a jogging activity, and a running activity.

81. The method of claim 78, wherein the gait attribute of the user is determined with an update frequency greater than a step frequency of the user and less than a sampling rate of an accelerometer of the mobile or wearable device.

82. A method comprising:
   determining a gait related information of a user of a mobile or wearable device in real time as the gait related information of the user occurs; wherein the mobile or wearable device is carried by the user; wherein a user's representation in the mobile or wearable device is composed of at least three movable parts; and
   controlling an attribute of the user's representation with the determined gait related information; wherein the attribute varies, in real time as the gait related information occurs, with the determined gait related information by following a mathematical relationship which uses a multiplication.

83. The method of claim 82, further comprising:
   determining a footstep of the user in real time as the footstep occurs; and using said footstep to synchronize a head movement of the user's representation with said footstep; wherein the head movement comprises a cyclical rotation.

84. The method of claim 82, wherein the gait related information is selected from a set consisting of: a gait velocity of the user, a gait activity of the user, a gait cadence of the user, and a length of a gait step of the user; wherein the gait activity of the user is selected from a set consisting of: a walking activity, a jogging activity, and a running activity.

85. The method of claim 82, wherein the gait related information is determined with an update frequency greater than an upper edge of a frequency band of a gait activity of the user and less than a sampling rate of an accelerometer of the mobile or wearable device.

86. The method of claim 82, wherein the gait related information is determined with an update frequency greater than a step frequency of the user and less than a sampling rate of an accelerometer of the mobile or wearable device.

87. A method comprising:
determining a gait related information of a user of a mobile or wearable device in real time as the gait related information of the user occurs; wherein the mobile or wearable device is carried by the user; wherein a user's representation in the mobile or wearable device is composed of at least three movable parts; wherein the determining comprises leveraging an accelerometer; wherein the gait related information is determined with an update frequency greater than an upper edge of a frequency band of a gait activity of the user and less than a sampling rate of the accelerometer; and
controlling, in real time as the gait related information occurs, the user's representation with the determined gait related information.

88. The method of claim 87, further comprising:
determining a footstep of the user in real time as the footstep occurs; and
using said footstep to synchronize a head movement of the user's representation with said footstep; wherein the head movement comprises a cyclical rotation.

89. The method of claim 87, wherein the upper edge is 3 Hz.

90. The method of claim 87, wherein the upper edge is 8 Hz.

91. The method of claim 87, wherein the gait related information is selected from a set consisting of: a gait velocity of the user, the gait activity of the user, a gait cadence of the user, and a length of a gait step of the user; wherein the gait activity of the user is selected from a set consisting of: a walking activity, a jogging activity, and a running activity.

92. The method of claim 87, wherein the controlling is performed with an update frequency lower than a refresh rate of a screen of the mobile or wearable device and greater than the upper edge of the frequency band of the gait activity of the user.

93. A method comprising:
determining a gait related information of a user of a mobile or wearable device in real time as the gait related information of the user occurs; wherein the mobile or wearable device is carried by the user; wherein a user's representation in the mobile or wearable device is composed of at least three movable parts; wherein the determining comprises leveraging an accelerometer; and
controlling, in real time as the gait related information occurs, the user's representation with the determined gait related information; wherein the controlling is performed with an update frequency less than a refresh rate of a screen of the mobile or wearable device and greater than an upper edge of a frequency band of a gait activity of the user.

94. The method of claim 93, further comprising:
determining a footstep of the user in real time as the footstep occurs; and
using said footstep to synchronize a head movement of the user's representation with said footstep; wherein the head movement comprises a cyclical rotation.

95. The method of claim 93, wherein the upper edge is 3 Hz.

96. The method of claim 93, wherein the upper edge is 8 Hz.

97. The method of claim 93, wherein said update frequency is constant and less than a sampling rate of the accelerometer.

98. The method of claim 93, wherein said update frequency is constant and less than a sampling rate of the accelerometer; and wherein said sampling rate is variable.

99. The method of claim 93, wherein the gait related information is selected from a set consisting of: a gait velocity of the user, the gait activity of the user, a gait cadence of the user, and a length of a gait step of the user; wherein the gait activity of the user is selected from a set consisting of: a walking activity, a jogging activity, and a running activity.

100. A method comprising:
determining a gait related information of a user of a mobile or wearable device in real time as the gait related information of the user occurs; wherein the mobile or wearable device is carried by the user; wherein a user's representation in the mobile or wearable device is composed of at least three movable parts;
controlling, in real time as the gait related information occurs, the user's representation with the determined gait related information;
determining a footstep of the user in real time as the footstep occurs; and
using said footstep to synchronize a movement of at least one movable part of said at least three movable parts of the user's representation with the determined footstep; wherein the at least one movable part is above a hip of the user's representation.

101. The method of claim 100, wherein the at least one movable part comprises a head of the user's representation.

102. The method of claim 101, wherein the gait related information is selected from a set consisting of: a gait velocity of the user, a gait activity of the user, a gait cadence of the user, and a length of a gait step of the user;
wherein the gait activity of the user is selected from a set consisting of: a walking activity, a jogging activity, and a running activity.

103. The method of claim 101, wherein the movement of the at least one movable part comprises a cyclical rotation.

104. The method of claim 103, wherein the gait related information is selected from a set consisting of: a gait velocity of the user, a gait activity of the user, a gait cadence of the user, and a length of a gait step of the user; wherein the gait activity of the user is selected from a set consisting of: a walking activity, a jogging activity, and a running activity.

105. The method of claim 101, wherein the movement of the at least one movable part comprises two different cyclical rotations.

106. The method of claim 101, further comprising:
determining a time instant of the determined footstep; and
using the determined time instant to synchronize the movement of the at least one movable part with said footstep by: assigning a frame at which the user's representation's head is shown rotated with a maximum rotation angle of a cyclical rotation, to the determined time instant of the footstep of the user.

107. The method of claim 106, wherein the gait related information is selected from a set consisting of: a gait velocity of the user, a gait activity of the user, a gait cadence of the user, and a length of a gait step of the user; wherein the gait activity of the user is selected from a set consisting of: a walking activity, a jogging activity, and a running activity.

108. The method of claim 100, wherein the at least one movable part comprises a hair of the user's representation.

109. The method of claim 108, wherein a root of the hair is assigned a weight different from a weight assigned to a tip of the hair.

110. The method of claim 100, wherein the movement of the at least one movable part comprises a facial expression of the user's representation.

111. The method of claim 100, wherein the at least one movable part comprises a movable part of a face of the user's representation.

112. The method of claim 111, wherein the gait related information is selected from a set consisting of: a gait velocity of the user, a gait activity of the user, a gait cadence of the user, and a length of a gait step of the user;
wherein the gait activity of the user is selected from a set consisting of: a walking activity, a jogging activity, and a running activity.

113. The method of claim 100, wherein the at least one movable part comprises an eye of the user's representation.

114. The method of claim 100, wherein the at least one movable part comprises an eyebrow of the user's representation.

115. A method comprising:
determining a gait related information of a user of a mobile or wearable device in real time as the gait related information of the user occurs; wherein the mobile or wearable device is carried by the user; wherein a user's representation in the mobile or wearable device is composed of at least three movable parts;
controlling, in real time as the gait related information occurs, the user's representation with the determined gait related information;
determining a footstep of the user in real time as the footstep occurs; and
using said footstep to synchronize a rotation of at least one movable part of an upper body of the user's representation with the determined footstep; wherein the at least one movable part of the upper body of the user's representation is from the at least three movable parts of the user's representation.

116. The method of claim 115, wherein the gait related information is selected from a set consisting of: a gait velocity of the user, a gait activity of the user, a gait cadence of the user, and a length of a gait step of the user; wherein the gait activity of the user is selected from a set consisting of: a walking activity, a jogging activity, and a running activity.

117. A method comprising:
determining a gait related information of a user of a mobile or wearable device in real time as the gait related information of the user occurs; wherein the mobile or wearable device is carried by the user; wherein a user's representation in the mobile or wearable device is composed of at least three movable parts;
controlling, in real time as the gait related information occurs, the user's representation with the determined gait related information;
determining a footstep of the user in real time as the footstep occurs; and
using said footstep to synchronize a cyclical up and down movement of an upper body of the user's representation with the determined footstep.

118. The method of claim 117, wherein the gait related information is selected from a set consisting of: a gait velocity of the user, a gait activity of the user, a gait cadence of the user, and a length of a gait step of the user; wherein the gait activity of the user is selected from a set consisting of: a walking activity, a jogging activity, and a running activity.

119. A system comprising:
one or more processors; and
a processor-readable medium including instructions which, when executed by the one or more processors, cause the one or more processors to perform functions comprising:
determining a gait velocity of a user of a mobile or wearable device in real time as the gait velocity occurs; wherein the mobile or wearable device is carried by the user; and
controlling, in real time as the gait velocity occurs, a user's representation in the mobile or wearable device with the determined gait velocity; wherein the user's representation is composed of at least seventy movable parts; and wherein the controlling comprises:
controlling, in real time as the gait velocity occurs, one or more attributes of at least fifty of said movable parts of the user's representation with the determined gait velocity.

120. The system of claim 119, the functions further comprising:
determining a footstep of the user in real time as the footstep occurs; and
using said footstep to synchronize a head movement of the user's representation with said footstep; wherein the head movement comprises a cyclical rotation.

121. A system comprising:
one or more processors; and
a processor-readable medium including instructions which, when executed by the one or more processors, cause the one or more processors to perform functions comprising:
determining a gait velocity of a user of a mobile or wearable device in real time as the gait velocity occurs; wherein the mobile or wearable device is carried by the user;
controlling, in real time as the gait velocity occurs, a user's representation in the mobile or wearable device with the determined gait velocity; wherein the user's representation is composed of at least three movable parts; and
controlling, in real time as the gait velocity occurs, a position of a frame on a screen of the mobile or wearable device with the determined gait velocity.

122. The system of claim 121, the functions further comprising:
    determining a footstep of the user in real time as the footstep occurs; and
    using said footstep to synchronize a head movement of the user's representation with said footstep; wherein the head movement comprises a cyclical rotation.

123. The system of claim 121, wherein the gait velocity is determined with an update frequency greater than a step frequency of the user and less than a sampling rate of an accelerometer of the mobile or wearable device.

124. The system of claim 121, wherein the frame shows the user's representation.

125. The system of claim 121, wherein the frame shows a representation different from the user's representation.

126. A system comprising:
    one or more processors; and
    a processor-readable medium including instructions which, when executed by the one or more processors, cause the one or more processors to perform functions comprising:
        determining a gait velocity of a user of a mobile or wearable device in real time as the gait velocity occurs; wherein the mobile or wearable device is carried by the user; and
        controlling, in real time as the gait velocity occurs, a user's representation in the mobile or wearable device with the determined gait velocity; wherein the controlling comprises:
            controlling an attribute of the user's representation with the determined gait velocity;
            wherein the attribute varies with the determined gait velocity by following a mathematical relationship which relates the attribute and the determined gait velocity.

127. The system of claim 126, the functions further comprising:
    determining a footstep of the user in real time as the footstep occurs; and
    using said footstep to synchronize a head movement of the user's representation with said footstep; wherein the head movement comprises a cyclical rotation.

128. The system of claim 126, wherein the gait velocity is determined with an update frequency greater than a step frequency of the user and less than a sampling rate of an accelerometer of the mobile or wearable device.

129. The system of claim 126, wherein the attribute is different from a velocity.

130. The system of claim 126, wherein the mathematical relationship uses a multiplication.

131. The system of claim 126, wherein the user's representation is composed of at least three movable parts, the functions further comprising: controlling, in real time as the gait velocity occurs, an aspect of an application in the mobile or wearable device with the determined gait velocity; wherein the aspect of the application is different from the user's representation.

132. The system of claim 126, wherein the user's representation is composed of at least three movable parts, the functions further comprising: controlling, in real time as the gait velocity occurs, a representation with the determined gait velocity; wherein the representation is different from the user's representation.

133. The system of claim 126, the functions further comprising:
    determining a gait cadence of the user in real time as the gait cadence occurs; and
    controlling, in real time as the gait cadence occurs, one or more attributes of the user's representation with the determined gait cadence.

134. The system of claim 126, the functions further comprising:
    recognizing a gait activity of the user in real time as the gait activity occurs by leveraging a machine learning algorithm; and
    controlling a gait activity of the user's representation with the recognized gait activity of the user; wherein the gait activity of the user is recognized from a set comprising a walking activity and a running activity.

135. The system of claim 134, the functions further comprising:
    determining a footstep of the user in real time as the footstep occurs; and
    using said footstep to synchronize a head movement of the user's representation with said footstep; wherein the head movement comprises a cyclical rotation.

136. A system comprising:
    one or more processors; and
    a processor-readable medium including instructions which, when executed by the one or more processors, cause the one or more processors to perform functions comprising:
        determining a gait activity of a user of a mobile or wearable device in real time as the gait activity of the user occurs; wherein the mobile or wearable device is carried by the user; and
        controlling, in real time as the gait activity of the user occurs, a user's representation in the mobile or wearable device with the determined gait activity of the user; wherein the user's representation is composed of at least three movable parts;
        wherein the determining comprises: recognizing the gait activity of the user by leveraging a machine learning algorithm; and wherein the controlling comprises: controlling a gait activity of the user's representation with the recognized gait activity of the user; wherein the gait activity of the user is recognized from a set comprising: a walking activity, and a running activity.

137. The system of claim 136, the functions further comprising:
    determining a footstep of the user in real time as the footstep occurs; and
    using said footstep to synchronize a head movement of the user's representation with said footstep; wherein the head movement comprises a cyclical rotation.

138. The system of claim 136, wherein the gait activity of the user is determined with an update frequency greater than an upper edge of a frequency band of the gait activity of the user and less than a sampling rate of an accelerometer of the mobile or wearable device.

139. The system of claim 136, wherein the gait activity of the user is determined with an update frequency greater than a step frequency of the user and less than a sampling rate of an accelerometer of the mobile or wearable device.

140. The system of claim 136, the functions further comprising:
    determining a gait cadence of the user in real time as the gait cadence occurs; and
    controlling, in real time as the gait cadence occurs, one or more attributes of the user's representation by using the determined gait cadence.

141. The system of claim 140, the functions further comprising:
    determining a footstep of the user in real time as the footstep occurs; and
    using said footstep to synchronize a head movement of the user's representation with said footstep; wherein the head movement comprises a cyclical rotation.

142. The system of claim 136, the functions further comprising:
    determining a length of a gait step of the user in real time as the gait step of the user occurs; and
    controlling, in real time as the gait step of the user occurs, a length of a gait step of the user's representation with the determined length of the gait step of the user;
    wherein the mobile or wearable device is a smartphone.

143. The system of claim 142, the functions further comprising:
    determining a footstep of the user in real time as the footstep occurs; and
    using said footstep to synchronize a head movement of the user's representation with said footstep; wherein the head movement comprises a cyclical rotation.

144. The system of claim 136, the functions further comprising: controlling, in real time as the gait activity of the user occurs, an aspect of an application in the mobile or wearable device with the determined gait activity of the user; wherein the aspect of the application is different from the user's representation.

145. A system comprising:
    one or more processors; and
    a processor-readable medium including instructions which, when executed by the one or more processors, cause the one or more processors to perform functions comprising:
        determining a length of a gait step of a user of a mobile or wearable device in real time as the gait step of the user occurs; wherein the mobile or wearable device is carried by the user;
        determining, by using the determined length of the gait step of the user, a distance travelled by the user; and
        controlling, in real time as the gait step of the user occurs, a user's representation in the mobile or wearable device with the determined length of the gait step of the user;
        wherein the user performs at least a complete gait cycle comprising the gait step of the user and another gait step of the user; wherein the controlling comprises: controlling a length of a gait step of the user's representation with the determined length of the gait step of the user.

146. The system of claim 145, the functions further comprising:
    determining a footstep of the user in real time as the footstep occurs; and
    using said footstep to synchronize a head movement of the user's representation with said footstep; wherein the head movement comprises a cyclical rotation.

147. A system comprising:
    one or more processors; and
    a processor-readable medium including instructions which, when executed by the one or more processors, cause the one or more processors to perform functions comprising:
        determining a length of a gait step of a user of a mobile or wearable device in real time as the gait step of the user occurs; wherein the mobile or wearable device is carried by the user; and
        controlling, in real time as the gait step of the user occurs, a user's representation in the mobile or wearable device with the determined length of the gait step of the user;
        wherein the user performs a gait activity selected from a set consisting of: a walking activity, a jogging activity, and a running activity; wherein the controlling comprises: controlling a length of a gait step of the user's representation with the determined length of the gait step of the user.

148. The system of claim 147, the functions further comprising:
    determining a footstep of the user in real time as the footstep occurs; and
    using said footstep to synchronize a head movement of the user's representation with said footstep; wherein the head movement comprises a cyclical rotation.

149. The system of claim 148, wherein the mobile or wearable device is a wearable device worn on a wrist of the user.

150. The system of claim 148, wherein the mobile or wearable device is a wearable device worn: on a face of the user, and/or on a head of the user.

151. A system comprising:
    one or more processors; and
    a processor-readable medium including instructions which, when executed by the one or more processors, cause the one or more processors to perform functions comprising:
        determining a length of a gait step of a user of a mobile or wearable device in real time as the gait step of the user occurs; wherein the mobile or wearable device is carried by the user; and
        controlling, in real time as the gait step of the user occurs, a user's representation in the mobile or wearable device with the determined length of the gait step of the user;
        wherein the user travels from a place to a different place; wherein the controlling comprises: controlling a length of a gait step of the user's representation with the determined length of the gait step of the user.

152. The system of claim 151, the functions further comprising:
    determining a footstep of the user in real time as the footstep occurs; and
    using said footstep to synchronize a head movement of the user's representation with said footstep; wherein the head movement comprises a cyclical rotation.

153. A system comprising:
    one or more processors; and
    a processor-readable medium including instructions which, when executed by the one or more processors, cause the one or more processors to perform functions comprising:
        determining a length of a gait step of a user of a mobile or wearable device in real time as the gait step of the user occurs; wherein the mobile or wearable device is carried by the user; and
        controlling, in real time as the gait step of the user occurs, a user's representation in the mobile or wearable device with the determined length of the gait step of the user;
        wherein the mobile or wearable device is a smartphone; wherein the controlling comprises:

controlling a length of a gait step of the user's representation with the determined length of the gait step of the user.

154. The system of claim 153, the functions further comprising:
determining a footstep of the user in real time as the footstep occurs; and
using said footstep to synchronize a head movement of the user's representation with said footstep; wherein the head movement comprises a cyclical rotation.

155. A system comprising:
one or more processors; and
a processor-readable medium including instructions which, when executed by the one or more processors, cause the one or more processors to perform functions comprising:
determining a length of a gait step of a user of a mobile or wearable device in real time as the gait step of the user occurs; wherein the mobile or wearable device is carried by the user; and
controlling, in real time as the gait step of the user occurs, a user's representation in the mobile or wearable device with the determined length of the gait step of the user;
wherein a first gait cycle comprising the gait step of the user and another gait step of the user, is emulated by the user's representation with a second gait cycle of two gait steps of the user's representation in real time as the first gait cycle occurs.

156. The system of claim 155, the functions further comprising:
determining a footstep of the user in real time as the footstep occurs; and
using said footstep to synchronize a head movement of the user's representation with said footstep; wherein the head movement comprises a cyclical rotation.

157. The system of claim 155, wherein the second gait cycle comprises at least 3 different postures.

158. The system of claim 155, wherein a length of at least one of the two gait steps of the user's representation, is controlled with the determined length of the gait step of the user.

159. A system comprising:
one or more processors; and
a processor-readable medium including instructions which, when executed by the one or more processors, cause the one or more processors to perform functions comprising:
determining a gait cadence of a user of a mobile or wearable device in real time as the gait cadence occurs; wherein the mobile or wearable device is carried by the user; and
controlling, in real time as the gait cadence occurs, a user's representation in the mobile or wearable device with the determined gait cadence;
wherein the controlling comprises: selecting a frame by using the determined cadence.

160. The system of claim 159, wherein the frame shows a posture of the user's representation; wherein a gait cycle of the user's representation is composed of at least three different postures.

161. The system of claim 160, the functions further comprising:
determining a footstep of the user in real time as the footstep occurs; and
using said footstep to synchronize a head movement of the user's representation with said footstep; wherein the head movement comprises a cyclical rotation.

162. A system comprising:
one or more processors; and
a processor-readable medium including instructions which, when executed by the one or more processors, cause the one or more processors to perform functions comprising:
determining a gait cadence of a user of a mobile or wearable device in real time as the gait cadence occurs; wherein the mobile or wearable device is carried by the user;
controlling, in real time as the gait cadence occurs, a user's representation in the mobile or wearable device with the determined gait cadence; and
controlling an aspect of an application with the determined gait cadence; wherein the aspect is different from the user's representation.

163. The system of claim 162, the functions further comprising:
determining a footstep of the user in real time as the footstep occurs; and
using said footstep to synchronize a head movement of the user's representation with said footstep; wherein the head movement comprises a cyclical rotation.

164. A system comprising:
one or more processors; and
a processor-readable medium including instructions which, when executed by the one or more processors, cause the one or more processors to perform functions comprising:
determining a gait cadence of a user of a mobile or wearable device in real time as the gait cadence occurs; wherein the mobile or wearable device is carried by the user; and
controlling, in real time as the gait cadence occurs, a user's representation in the mobile or wearable device with the determined gait cadence; wherein the controlling comprises:
controlling a time length of a gait cycle of the user's representation with the determined gait cadence; wherein the gait cycle comprises at least three different postures.

165. The system of claim 164, the functions further comprising:
determining a footstep of the user in real time as the footstep occurs; and
using said footstep to synchronize a head movement of the user's representation with said footstep; wherein the head movement comprises a cyclical rotation.

166. A system comprising:
one or more processors; and
a processor-readable medium including instructions which, when executed by the one or more processors, cause the one or more processors to perform functions comprising:
determining a gait cadence of a user of a mobile or wearable device in real time as the gait cadence occurs; wherein the mobile or wearable device is carried by the user; and
controlling, in real time as the gait cadence occurs, a user's representation in the mobile or wearable device with the determined gait cadence; wherein the controlling comprises:
controlling a time length of a frame with the determined gait cadence.

167. The system of claim 166, wherein the time length of the frame is controlled by leveraging: the determined cadence, and a total number of frames contained in a gait cycle of the user's representation.

168. The system of claim 167, the functions further comprising:
dentifying a footstep of the user in real time as the footstep occurs; and
using said footstep to synchronize a head movement of the user's representation with said footstep; wherein the head movement comprises a cyclical rotation.

169. A system comprising:
one or more processors; and
a processor-readable medium including instructions which, when executed by the one or more processors, cause the one or more processors to perform functions comprising:
determining a gait cadence of a user of a mobile or wearable device in real time as the gait cadence occurs; wherein the mobile or wearable device is carried by the user; and
controlling, in real time as the gait cadence occurs, a user's representation in the mobile or wearable device with the determined gait cadence; wherein the user's representation is composed of at least three movable parts; wherein the controlling comprises: controlling one or more attributes of three or more of said movable parts of the user's representation with the determined gait cadence.

170. The system of claim 169, the functions further comprising:
determining a footstep of the user in real time as the footstep occurs; and
using said footstep to synchronize a head movement of the user's representation with said footstep; wherein the head movement comprises a cyclical rotation.

171. The system of claim 169, the functions further comprising: controlling, in real time as the gait cadence of the user occurs, a gait cadence of the user's representation with the determined gait cadence of the user.

172. A system comprising:
one or more processors; and
a processor-readable medium including instructions which, when executed by the one or more processors, cause the one or more processors to perform functions comprising:
determining a gait attribute of a user of a mobile or wearable device in real time as the gait attribute occurs; wherein the mobile or wearable device is carried by the user;
controlling, in real time as the gait attribute occurs, a user's representation in the mobile or wearable device with the determined gait attribute;
determining a length of a gait step of the user in real time as the gait step of the user occurs; and
controlling an aspect of an application in the mobile or wearable device with the determined length of the gait step of the user, wherein the aspect of the application is different from the user's representation.

173. The system of claim 172, wherein the aspect comprises elements different from the user's representation; wherein the user's representation may step on said elements.

174. A system comprising:
one or more processors; and
a processor-readable medium including instructions which, when executed by the one or more processors, cause the one or more processors to perform functions comprising:
determining a gait related information of a user of a mobile or wearable device in real time as the gait related information occurs; wherein the mobile or wearable device is carried by the user;
controlling, in real time as the gait related information occurs, a user's representation in the mobile or wearable device with the determined gait related information; wherein the user's representation is composed of at least three movable parts;
determining a footstep of the user in real time as the footstep of the user occurs; and
controlling, in real time as the footstep of the user occurs, an element different from the user's representation by using said footstep of the user; wherein the user's representation steps on said element.

175. The system of claim 174, the functions further comprising:
using said footstep of the user to synchronize a head movement of the user's representation with said footstep of the user; wherein the head movement comprises a cyclical rotation.

176. The system of claim 175, wherein the gait related information is selected from a set consisting of: a gait velocity of the user, a gait activity of the user, a gait cadence of the user, and a length of a gait step of the user; wherein the gait activity of the user is selected from a set consisting of: a walking activity, a jogging activity, and a running activity.

177. A system comprising:
one or more processors; and
a processor-readable medium including instructions which, when executed by the one or more processors, cause the one or more processors to perform functions comprising:
determining a gait related information of a user of a mobile or wearable device in real time as the gait related information occurs; wherein the mobile or wearable device is carried by the user; wherein a user's representation in the mobile or wearable device is composed of at least three movable parts; and
controlling, in real time as the gait related information occurs, independently one or more attributes of at least two of said movable parts with the determined gait related information.

178. The system of claim 177, the functions further comprising:
determining a footstep of the user in real time as the footstep occurs; and
using said footstep to synchronize a head movement of the user's representation with said footstep; wherein the head movement comprises a cyclical rotation.

179. The system of claim 178, wherein the gait related information is selected from a set consisting of: a gait velocity of the user, a gait activity of the user, a gait cadence of the user, and a length of a gait step of the user; wherein the gait activity of the user is selected from a set consisting of: a walking activity, a jogging activity, and a running activity.

180. A system comprising:
one or more processors; and
a processor-readable medium including instructions which, when executed by the one or more processors, cause the one or more processors to perform functions comprising:
  determining a gait related information of a user of a mobile or wearable device in real time as the gait related information of the user occurs; wherein the mobile or wearable device is carried by the user; wherein a user's representation in the mobile or wearable device is composed of at least three movable parts;
  controlling, in real time as the gait related information of the user occurs, the user's representation with the determined gait related information of the user;
  determining a footstep of the user in real time as the footstep of the user occurs;
  determining a time instant of the determined footstep of the user; and
  using the determined time instant to synchronize a stepping of the user's representation with the footstep of the user, by assigning a frame at which the user's representation is shown stepping to the determined time instant of the footstep of the user.

181. The system of claim 180, the functions further comprising:
  using said footstep of the user to: synchronize a head movement of the user's representation with said footstep of the user; wherein the head movement comprises a cyclical rotation.

182. The system of claim 181, wherein the gait related information of the user is selected from a set consisting of: a gait velocity of the user, a gait activity of the user, a gait cadence of the user, and a length of a gait step of the user; wherein the gait activity of the user is selected from a set consisting of: a walking activity, a jogging activity, and a running activity.

183. The system of claim 180, wherein the synchronizing the stepping of the user's representation with the footstep of the user comprises: determining a frame number of a frame which should be displayed, by using a determined time distance and a total number of frames contained in one gait cycle of the user's representation; wherein the frame which should be displayed comprises the frame at which the user's representation is shown stepping.

184. A system comprising:
one or more processors; and
a processor-readable medium including instructions which, when executed by the one or more processors, cause the one or more processors to perform functions comprising:
  determining a gait attribute of a user of a mobile or wearable device in real time as the gait attribute of the user occurs; wherein the mobile or wearable device is carried by the user;
  wherein a user's representation in the mobile or wearable device is composed of at least three movable parts; and
  controlling, in real time as the gait attribute of the user occurs, the user's representation with the determined gait attribute of the user; wherein the controlling comprises: selecting a file which contains at least three images by using the determined gait attribute.

185. The system of claim 184, wherein each one of said images shows a different posture of the user's representation.

186. A system comprising:
one or more processors; and
a processor-readable medium including instructions which, when executed by the one or more processors, cause the one or more processors to perform functions comprising:
  determining a gait attribute of a user of a mobile or wearable device in real time as the gait attribute of the user occurs; wherein the mobile or wearable device is carried by the user;
  wherein a user's representation in the mobile or wearable device is composed of at least three movable parts;
  controlling, in real time as the gait attribute of the user occurs, the user's representation with the determined gait attribute of the user; and
  controlling a scaling of a representation with the determined gait attribute of the user, wherein the representation is different from the user's representation.

187. The system of claim 186, the functions further comprising:
  determining a footstep of the user in real time as the footstep occurs; and
  using said footstep to synchronize a head movement of the user's representation with said footstep; wherein the head movement comprises a cyclical rotation.

188. The system of claim 187, wherein the gait attribute is selected from a set consisting of: a gait velocity of the user, a gait activity of the user, a gait cadence of the user, and a length of a gait step of the user; wherein the gait activity of the user is selected from a set consisting of: a walking activity, a jogging activity, and a running activity.

189. The system of claim 186, wherein the gait attribute of the user is determined with an update frequency greater than a step frequency of the user and less than a sampling rate of an accelerometer of the mobile or wearable device.

190. A system comprising:
one or more processors; and
a processor-readable medium including instructions which, when executed by the one or more processors, cause the one or more processors to perform functions comprising:
  determining a gait attribute of a user of a mobile or wearable device in real time as the gait attribute of the user occurs; wherein the mobile or wearable device is carried by the user;
  wherein a user's representation in the mobile or wearable device is composed of at least three movable parts; and
  controlling, in real time as the gait attribute of the user occurs, the user's representation with the determined gait attribute of the user; wherein the controlling comprises: controlling a scaling of the user's representation with the determined gait attribute of the user.

191. The system of claim 190, the functions further comprising:
  determining a footstep of the user in real time as the footstep occurs; and
  using said footstep to synchronize a head movement of the user's representation with said footstep; wherein the head movement comprises a cyclical rotation.

192. The system of claim 191, wherein the gait attribute is selected from a set consisting of: a gait velocity of the user, a gait activity of the user, a gait cadence of the user, and a length of a gait step of the user; wherein the gait activity of the user is selected from a set consisting of: a walking activity, a jogging activity, and a running activity.

193. The system of claim 190, wherein the gait attribute of the user is determined with an update frequency greater than an upper edge of a frequency band of a gait activity of the user and less than a sampling rate of an accelerometer of the mobile or wearable device.

194. The system of claim 190, wherein the gait attribute of the user is determined with an update frequency greater than a step frequency of the user and less than a sampling rate of an accelerometer of the mobile or wearable device.

195. The system of claim 190, wherein the gait attribute is a velocity; the functions further comprising:
  determining a gait cadence of the user in real time as the gait cadence of the user occurs; and
  controlling, in real time as the gait cadence of the user occurs, one or more attributes of the user's representation by using the determined gait cadence of the user.

196. A system comprising:
  one or more processors; and
  a processor-readable medium including instructions which, when executed by the one or more processors, cause the one or more processors to perform functions comprising:
    determining a gait attribute of a user of a mobile or wearable device in real time as the gait attribute of the user occurs; wherein the mobile or wearable device is carried by the user;
    wherein a user's representation in the mobile or wearable device is composed of at least three movable parts; and
    controlling, in real time as the gait attribute of the user occurs, the user's representation with the determined gait attribute of the user; wherein a number of frames spanning a gait cycle of the user's representation is less than forty and greater than three.

197. The system of claim 196, the functions further comprising:
  determining a footstep of the user in real time as the footstep occurs; and
  using said footstep to synchronize a head movement of the user's representation with said footstep; wherein the head movement comprises a cyclical rotation.

198. The system of claim 197, wherein the gait attribute is selected from a set consisting of: a gait velocity of the user, a gait activity of the user, a gait cadence of the user, and a length of a gait step of the user; wherein the gait activity of the user is selected from a set consisting of: a walking activity, a jogging activity, and a running activity.

199. The system of claim 196, wherein the gait attribute of the user is determined with an update frequency greater than a step frequency of the user and less than a sampling rate of an accelerometer of the mobile or wearable device.

200. A system comprising:
  one or more processors; and
  a processor-readable medium including instructions which, when executed by the one or more processors, cause the one or more processors to perform functions comprising:
    determining a gait related information of a user of a mobile or wearable device in real time as the gait related information of the user occurs; wherein the mobile or wearable device is carried by the user;
    wherein a user's representation in the mobile or wearable device is composed of at least three movable parts; and
    controlling an attribute of the user's representation with the determined gait related information; wherein the attribute varies, in real time as the gait related information occurs, with the determined gait related information by following a mathematical relationship which uses a multiplication.

201. The system of claim 200, the functions further comprising:
  determining a footstep of the user in real time as the footstep occurs; and
  using said footstep to synchronize a head movement of the user's representation with said footstep; wherein the head movement comprises a cyclical rotation.

202. The system of claim 200, wherein the gait related information is selected from a set consisting of: a gait velocity of the user, a gait activity of the user, a gait cadence of the user, and a length of a gait step of the user; wherein the gait activity of the user is selected from a set consisting of: a walking activity, a jogging activity, and a running activity.

203. The system of claim 200, wherein the gait related information is determined with an update frequency greater than an upper edge of a frequency band of a gait activity of the user and less than a sampling rate of an accelerometer of the mobile or wearable device.

204. The system of claim 200, wherein the gait related information is determined with an update frequency greater than a step frequency of the user and less than a sampling rate of an accelerometer of the mobile or wearable device.

205. A system comprising:
  one or more processors; and
  a processor-readable medium including instructions which, when executed by the one or more processors, cause the one or more processors to perform functions comprising:
    determining a gait related information of a user of a mobile or wearable device in real time as the gait related information of the user occurs; wherein the mobile or wearable device is carried by the user; wherein a user's representation in the mobile or wearable device is composed of at least three movable parts; wherein the determining comprises leveraging an accelerometer; wherein the gait related information is determined with an update frequency greater than an upper edge of a frequency band of a gait activity of the user and less than a sampling rate of the accelerometer; and
    controlling, in real time as the gait related information occurs, the user's representation with the determined gait related information.

206. The system of claim 205, the functions further comprising:
  determining a footstep of the user in real time as the footstep occurs; and
  using said footstep to synchronize a head movement of the user's representation with said footstep; wherein the head movement comprises a cyclical rotation.

207. The system of claim 205, wherein the upper edge is 3 Hz.

208. The system of claim 205, wherein the upper edge is 8 Hz.

209. The system of claim 205, wherein the gait related information is selected from a set consisting of: a gait velocity of the user, the gait activity of the user, a gait cadence of the user, and a length of a gait step of the user;

wherein the gait activity of the user is selected from a set consisting of: a walking activity, a jogging activity, and a running activity.

210. The system of claim 205, wherein the controlling is performed with an update frequency lower than a refresh rate of a screen of the mobile or wearable device and greater than the upper edge of the frequency band of the gait activity of the user.

211. A system comprising:
one or more processors; and
a processor-readable medium including instructions which, when executed by the one or more processors, cause the one or more processors to perform functions comprising:
determining a gait related information of a user of a mobile or wearable device in real time as the gait related information of the user occurs; wherein the mobile or wearable device is carried by the user; wherein a user's representation in the mobile or wearable device is composed of at least three movable parts; wherein the determining comprises leveraging an accelerometer; and
controlling, in real time as the gait related information occurs, the user's representation with the determined gait related information; wherein the controlling is performed with an update frequency less than a refresh rate of a screen of the mobile or wearable device and greater than an upper edge of a frequency band of a gait activity of the user.

212. The system of claim 211, the functions further comprising:
determining a footstep of the user in real time as the footstep occurs; and
using said footstep to synchronize a head movement of the user's representation with said footstep; wherein the head movement comprises a cyclical rotation.

213. The system of claim 211, wherein the upper edge is 3 Hz.

214. The system of claim 211, wherein the upper edge is 8 Hz.

215. The system of claim 211, wherein said update frequency is constant and less than a sampling rate of the accelerometer.

216. The system of claim 211, wherein said update frequency is constant and less than a sampling rate of the accelerometer; and wherein said sampling rate is variable.

217. The system of claim 211, wherein the gait related information is selected from a set consisting of: a gait velocity of the user, the gait activity of the user, a gait cadence of the user, and a length of a gait step of the user; wherein the gait activity of the user is selected from a set consisting of: a walking activity, a jogging activity, and a running activity.

218. A system comprising:
one or more processors; and
a processor-readable medium including instructions which, when executed by the one or more processors, cause the one or more processors to perform functions comprising:
determining a gait related information of a user of a mobile or wearable device in real time as the gait related information of the user occurs; wherein the mobile or wearable device is carried by the user; wherein a user's representation in the mobile or wearable device is composed of at least three movable parts;
controlling, in real time as the gait related information occurs, the user's representation with the determined gait related information;
determining a footstep of the user in real time as the footstep occurs; and
using said footstep to synchronize a movement of at least one movable part of said at least three movable parts of the user's representation with the determined footstep; wherein the at least one movable part is above a hip of the user's representation.

219. The system of claim 218, wherein the at least one movable part comprises a head of the user's representation.

220. The system of claim 219, wherein the gait related information is selected from a set consisting of: a gait velocity of the user, a gait activity of the user, a gait cadence of the user, and a length of a gait step of the user; wherein the gait activity of the user is selected from a set consisting of: a walking activity, a jogging activity, and a running activity.

221. The system of claim 219, wherein the movement of the at least one movable part comprises a cyclical rotation.

222. The system of claim 221, wherein the gait related information is selected from a set consisting of: a gait velocity of the user, a gait activity of the user, a gait cadence of the user, and a length of a gait step of the user;
wherein the gait activity of the user is selected from a set consisting of: a walking activity, a jogging activity, and a running activity.

223. The system of claim 219, wherein the movement of the at least one movable part comprises two different cyclical rotations.

224. The system of claim 219, the functions further comprising:
determining a time instant of the determined footstep; and
using the determined time instant to synchronize the movement of the at least one movable part with said footstep by: assigning a frame at which the user's representation's head is shown rotated with a maximum rotation angle of a cyclical rotation, to the determined time instant of the footstep of the user.

225. The system of claim 224, wherein the gait related information is selected from a set consisting of: a gait velocity of the user, a gait activity of the user, a gait cadence of the user, and a length of a gait step of the user;
wherein the gait activity of the user is selected from a set consisting of: a walking activity, a jogging activity, and a running activity.

226. The system of claim 218, wherein the at least one movable part comprises a hair of the user's representation.

227. The system of claim 226, wherein a root of the hair is assigned a weight different from a weight assigned to a tip of the hair.

228. The system of claim 218, wherein the movement of the at least one movable part comprises a facial expression of the user's representation.

229. The system of claim 218, wherein the at least one movable part comprises a movable part of a face of the user's representation.

230. The system of claim 229, wherein the gait related information is selected from a set consisting of: a gait velocity of the user, a gait activity of the user, a gait cadence of the user, and a length of a gait step of the user; wherein the gait activity of the user is selected from a set consisting of: a walking activity, a jogging activity, and a running activity.

231. The system of claim 218, wherein the at least one movable part comprises an eye of the user's representation.

232. The system of claim 218, wherein the at least one movable part comprises an eyebrow of the user's representation.

233. A system comprising:
one or more processors; and
a processor-readable medium including instructions which, when executed by the one or more processors, cause the one or more processors to perform functions comprising:
determining a gait related information of a user of a mobile or wearable device in real time as the gait related information of the user occurs; wherein the mobile or wearable device is carried by the user; wherein a user's representation in the mobile or wearable device is composed of at least three movable parts;
controlling, in real time as the gait related information occurs, the user's representation with the determined gait related information;
determining a footstep of the user in real time as the footstep occurs; and
using said footstep to synchronize a rotation of at least one movable part of an upper body of the user's representation with the determined footstep; wherein the at least one movable part of the upper body of the user's representation is from the at least three movable parts of the user's representation.

234. The system of claim 233, wherein the gait related information is selected from a set consisting of: a gait velocity of the user, a gait activity of the user, a gait cadence of the user, and a length of a gait step of the user; wherein the gait activity of the user is selected from a set consisting of: a walking activity, a jogging activity, and a running activity.

235. A system comprising:
one or more processors; and
a processor-readable medium including instructions which, when executed by the one or more processors, cause the one or more processors to perform functions comprising:
determining a gait related information of a user of a mobile or wearable device in real time as the gait related information of the user occurs; wherein the mobile or wearable device is carried by the user; wherein a user's representation in the mobile or wearable device is composed of at least three movable parts;
controlling, in real time as the gait related information occurs, the user's representation with the determined gait related information;
determining a footstep of the user in real time as the footstep occurs; and
using said footstep to synchronize a cyclical up and down movement of an upper body of the user's representation with the determined footstep.

236. The system of claim 235, wherein the gait related information is selected from a set consisting of: a gait velocity of the user, a gait activity of the user, a gait cadence of the user, and a length of a gait step of the user; wherein the gait activity of the user is selected from a set consisting of: a walking activity, a jogging activity, and a running activity.

237. A non-transitory processor-readable medium including instructions which, when executed by one or more processors, cause the one or more processors to perform functions comprising:
determining a gait velocity of a user of a mobile or wearable device in real time as the gait velocity occurs; wherein the mobile or wearable device is carried by the user; and
controlling, in real time as the gait velocity occurs, a user's representation in the mobile or wearable device with the determined gait velocity; wherein the user's representation is composed of at least seventy movable parts; and wherein the controlling comprises:
controlling, in real time as the gait velocity occurs, one or more attributes of at least fifty of said movable parts of the user's representation with the determined gait velocity.

238. The non-transitory processor-readable medium of claim 237, the functions further comprising:
determining a footstep of the user in real time as the footstep occurs; and
using said footstep to synchronize a head movement of the user's representation with said footstep; wherein the head movement comprises a cyclical rotation.

239. A non-transitory processor-readable medium including instructions which, when executed by one or more processors, cause the one or more processors to perform functions comprising:
determining a gait velocity of a user of a mobile or wearable device in real time as the gait velocity occurs; wherein the mobile or wearable device is carried by the user;
controlling, in real time as the gait velocity occurs, a user's representation in the mobile or wearable device with the determined gait velocity; wherein the user's representation is composed of at least three movable parts; and
controlling, in real time as the gait velocity occurs, a position of a frame on a screen of the mobile or wearable device with the determined gait velocity.

240. The non-transitory processor-readable medium of claim 239, the functions further comprising:
determining a footstep of the user in real time as the footstep occurs; and
using said footstep to synchronize a head movement of the user's representation with said footstep; wherein the head movement comprises a cyclical rotation.

241. The non-transitory processor-readable medium of claim 239, wherein the gait velocity is determined with an update frequency greater than a step frequency of the user and less than a sampling rate of an accelerometer of the mobile or wearable device.

242. The non-transitory processor-readable medium of claim 239, wherein the frame shows the user's representation.

243. The non-transitory processor-readable medium of claim 239, wherein the frame shows a representation different from the user's representation.

244. A non-transitory processor-readable medium including instructions which, when executed by one or more processors, cause the one or more processors to perform functions comprising:
determining a gait velocity of a user of a mobile or wearable device in real time as the gait velocity occurs; wherein the mobile or wearable device is carried by the user; and
controlling, in real time as the gait velocity occurs, a user's representation in the mobile or wearable device with the determined gait velocity; wherein the controlling comprises:

controlling an attribute of the user's representation with the determined gait velocity;
wherein the attribute varies with the determined gait velocity by following a mathematical relationship which relates the attribute and the determined gait velocity.

245. The non-transitory processor-readable medium of claim 244, the functions further comprising:
determining a footstep of the user in real time as the footstep occurs; and
using said footstep to synchronize a head movement of the user's representation with said footstep; wherein the head movement comprises a cyclical rotation.

246. The non-transitory processor-readable medium of claim 244, wherein the gait velocity is determined with an update frequency greater than a step frequency of the user and less than a sampling rate of an accelerometer of the mobile or wearable device.

247. The non-transitory processor-readable medium of claim 244, wherein the attribute is different from a velocity.

248. The non-transitory processor-readable medium of claim 244, wherein the mathematical relationship uses a multiplication.

249. The non-transitory processor-readable medium of claim 244, wherein the user's representation is composed of at least three movable parts, the functions further comprising:
controlling, in real time as the gait velocity occurs, an aspect of an application in the mobile or wearable device with the determined gait velocity; wherein the aspect of the application is different from the user's representation.

250. The non-transitory processor-readable medium of claim 244, wherein the user's representation is composed of at least three movable parts, the functions further comprising:
controlling, in real time as the gait velocity occurs, a representation with the determined gait velocity; wherein the representation is different from the user's representation.

251. The non-transitory processor-readable medium of claim 244, the functions further comprising:
determining a gait cadence of the user in real time as the gait cadence occurs; and
controlling, in real time as the gait cadence occurs, one or more attributes of the user's representation with the determined gait cadence.

252. The non-transitory processor-readable medium of claim 244, the functions further comprising:
recognizing a gait activity of the user in real time as the gait activity occurs by leveraging a machine learning algorithm; and
controlling a gait activity of the user's representation with the recognized gait activity of the user; wherein the gait activity of the user is recognized from a set comprising a walking activity and a running activity.

253. The non-transitory processor-readable medium of claim 252, the functions further comprising:
determining a footstep of the user in real time as the footstep occurs; and
using said footstep to synchronize a head movement of the user's representation with said footstep; wherein the head movement comprises a cyclical rotation.

254. A non-transitory processor-readable medium including instructions which, when executed by one or more processors, cause the one or more processors to perform functions comprising:
determining a gait activity of a user of a mobile or wearable device in real time as the gait activity of the user occurs; wherein the mobile or wearable device is carried by the user; and
controlling, in real time as the gait activity of the user occurs, a user's representation in the mobile or wearable device with the determined gait activity of the user; wherein the user's representation is composed of at least three movable parts;
wherein the determining comprises: recognizing the gait activity of the user by leveraging a machine learning algorithm; and wherein the controlling comprises: controlling a gait activity of the user's representation with the recognized gait activity of the user; wherein the gait activity of the user is recognized from a set comprising: a walking activity, and a running activity.

255. The non-transitory processor-readable medium of claim 254, the functions further comprising:
determining a footstep of the user in real time as the footstep occurs; and
using said footstep to synchronize a head movement of the user's representation with said footstep; wherein the head movement comprises a cyclical rotation.

256. The non-transitory processor-readable medium of claim 254, wherein the gait activity of the user is determined with an update frequency greater than an upper edge of a frequency band of the gait activity of the user and less than a sampling rate of an accelerometer of the mobile or wearable device.

257. The non-transitory processor-readable medium of claim 254, wherein the gait activity of the user is determined with an update frequency greater than a step frequency of the user and less than a sampling rate of an accelerometer of the mobile or wearable device.

258. The non-transitory processor-readable medium of claim 254, the functions further comprising:
determining a gait cadence of the user in real time as the gait cadence occurs; and
controlling, in real time as the gait cadence occurs, one or more attributes of the user's representation by using the determined gait cadence.

259. The non-transitory processor-readable medium of claim 258, the functions further comprising:
determining a footstep of the user in real time as the footstep occurs; and
using said footstep to synchronize a head movement of the user's representation with said footstep; wherein the head movement comprises a cyclical rotation.

260. The non-transitory processor-readable medium of claim 254, the functions further comprising:
determining a length of a gait step of the user in real time as the gait step of the user occurs; and
controlling, in real time as the gait step of the user occurs, a length of a gait step of the user's representation with the determined length of the gait step of the user; wherein the mobile or wearable device is a smartphone.

261. The non-transitory processor-readable medium of claim 260, the functions further comprising:
determining a footstep of the user in real time as the footstep occurs; and
using said footstep to synchronize a head movement of the user's representation with said footstep; wherein the head movement comprises a cyclical rotation.

262. The non-transitory processor-readable medium of claim 254, the functions further comprising: controlling, in real time as the gait activity of the user occurs, an aspect of an application in the mobile or wearable device with the determined gait activity of the user; wherein the aspect of the application is different from the user's representation.

263. A non-transitory processor-readable medium including instructions which, when executed by one or more processors, cause the one or more processors to perform functions comprising:
　determining a length of a gait step of a user of a mobile or wearable device in real time as the gait step of the user occurs; wherein the mobile or wearable device is carried by the user;
　determining, by using the determined length of the gait step of the user, a distance travelled by the user; and
　controlling, in real time as the gait step of the user occurs, a user's representation in the mobile or wearable device with the determined length of the gait step of the user;
　wherein the user performs at least a complete gait cycle comprising the gait step of the user and another gait step of the user; wherein the controlling comprises: controlling a length of a gait step of the user's representation with the determined length of the gait step of the user.

264. The non-transitory processor-readable medium of claim 263, the functions further comprising:
　determining a footstep of the user in real time as the footstep occurs; and
　using said footstep to synchronize a head movement of the user's representation with said footstep; wherein the head movement comprises a cyclical rotation.

265. A non-transitory processor-readable medium including instructions which, when executed by one or more processors, cause the one or more processors to perform functions comprising:
　determining a length of a gait step of a user of a mobile or wearable device in real time as the gait step of the user occurs; wherein the mobile or wearable device is carried by the user; and
　controlling, in real time as the gait step of the user occurs, a user's representation in the mobile or wearable device with the determined length of the gait step of the user;
　wherein the user performs a gait activity selected from a set consisting of: a walking activity, a jogging activity, and a running activity; wherein the controlling comprises: controlling a length of a gait step of the user's representation with the determined length of the gait step of the user.

266. The non-transitory processor-readable medium of claim 265, the functions further comprising:
　determining a footstep of the user in real time as the footstep occurs; and
　using said footstep to synchronize a head movement of the user's representation with said footstep; wherein the head movement comprises a cyclical rotation.

267. The non-transitory processor-readable medium of claim 266, wherein the mobile or wearable device is a wearable device worn on a wrist of the user.

268. The non-transitory processor-readable medium of claim 266, wherein the mobile or wearable device is a wearable device worn: on a face of the user, and/or on a head of the user.

269. A non-transitory processor-readable medium including instructions which, when executed by one or more processors, cause the one or more processors to perform functions comprising:
　determining a length of a gait step of a user of a mobile or wearable device in real time as the gait step of the user occurs; wherein the mobile or wearable device is carried by the user; and
　controlling, in real time as the gait step of the user occurs, a user's representation in the mobile or wearable device with the determined length of the gait step of the user;
　wherein the user travels from a place to a different place; wherein the controlling comprises:
　controlling a length of a gait step of the user's representation with the determined length of the gait step of the user.

270. The non-transitory processor-readable medium of claim 269, the functions further comprising:
　determining a footstep of the user in real time as the footstep occurs; and
　using said footstep to synchronize a head movement of the user's representation with said footstep; wherein the head movement comprises a cyclical rotation.

271. A non-transitory processor-readable medium including instructions which, when executed by one or more processors, cause the one or more processors to perform functions comprising:
　determining a length of a gait step of a user of a mobile or wearable device in real time as the gait step of the user occurs; wherein the mobile or wearable device is carried by the user; and
　controlling, in real time as the gait step of the user occurs, a user's representation in the mobile or wearable device with the determined length of the gait step of the user;
　wherein the mobile or wearable device is a smartphone; wherein the controlling comprises:
　controlling a length of a gait step of the user's representation with the determined length of the gait step of the user.

272. The non-transitory processor-readable medium of claim 271, the functions further comprising:
　determining a footstep of the user in real time as the footstep occurs; and
　using said footstep to synchronize a head movement of the user's representation with said footstep; wherein the head movement comprises a cyclical rotation.

273. A non-transitory processor-readable medium including instructions which, when executed by one or more processors, cause the one or more processors to perform functions comprising:
　determining a length of a gait step of a user of a mobile or wearable device in real time as the gait step of the user occurs; wherein the mobile or wearable device is carried by the user; and
　controlling, in real time as the gait step of the user occurs, a user's representation in the mobile or wearable device with the determined length of the gait step of the user;
　wherein a first gait cycle comprising the gait step of the user and another gait step of the user, is emulated by the user's representation with a second gait cycle of two gait steps of the user's representation in real time as the first gait cycle occurs.

274. The non-transitory processor-readable medium of claim 273, the functions further comprising:
　determining a footstep of the user in real time as the footstep occurs; and
　using said footstep to synchronize a head movement of the user's representation with said footstep; wherein the head movement comprises a cyclical rotation.

275. The non-transitory processor-readable medium of claim 273, wherein the second gait cycle comprises at least 3 different postures.

276. The non-transitory processor-readable medium of claim 273, wherein a length of at least one of the two gait steps of the user's representation, is controlled with the determined length of the gait step of the user.

277. A non-transitory processor-readable medium including instructions which, when executed by one or more processors, cause the one or more processors to perform functions comprising:
   determining a gait cadence of a user of a mobile or wearable device in real time as the gait cadence occurs; wherein the mobile or wearable device is carried by the user; and
   controlling, in real time as the gait cadence occurs, a user's representation in the mobile or wearable device with the determined gait cadence;
   wherein the controlling comprises: selecting a frame by using the determined cadence.

278. The non-transitory processor-readable medium of claim 277, wherein the frame shows a posture of the user's representation; wherein a gait cycle of the user's representation is composed of at least three different postures.

279. The non-transitory processor-readable medium of claim 278, the functions further comprising:
   determining a footstep of the user in real time as the footstep occurs; and
   using said footstep to synchronize a head movement of the user's representation with said footstep; wherein the head movement comprises a cyclical rotation.

280. A non-transitory processor-readable medium including instructions which, when executed by one or more processors, cause the one or more processors to perform functions comprising:
   determining a gait cadence of a user of a mobile or wearable device in real time as the gait cadence occurs; wherein the mobile or wearable device is carried by the user;
   controlling, in real time as the gait cadence occurs, a user's representation in the mobile or wearable device with the determined gait cadence; and
   controlling an aspect of an application with the determined gait cadence; wherein the aspect is different from the user's representation.

281. The non-transitory processor-readable medium of claim 280, the functions further comprising:
   determining a footstep of the user in real time as the footstep occurs; and
   using said footstep to synchronize a head movement of the user's representation with said footstep; wherein the head movement comprises a cyclical rotation.

282. A non-transitory processor-readable medium including instructions which, when executed by one or more processors, cause the one or more processors to perform functions comprising:
   determining a gait cadence of a user of a mobile or wearable device in real time as the gait cadence occurs; wherein the mobile or wearable device is carried by the user; and
   controlling, in real time as the gait cadence occurs, a user's representation in the mobile or wearable device with the determined gait cadence; wherein the controlling comprises:
   controlling a time length of a gait cycle of the user's representation with the determined gait cadence; wherein the gait cycle comprises at least three different postures.

283. The non-transitory processor-readable medium of claim 282, the functions further comprising:
   determining a footstep of the user in real time as the footstep occurs; and
   using said footstep to synchronize a head movement of the user's representation with said footstep; wherein the head movement comprises a cyclical rotation.

284. A non-transitory processor-readable medium including instructions which, when executed by one or more processors, cause the one or more processors to perform functions comprising:
   determining a gait cadence of a user of a mobile or wearable device in real time as the gait cadence occurs; wherein the mobile or wearable device is carried by the user; and
   controlling, in real time as the gait cadence occurs, a user's representation in the mobile or wearable device with the determined gait cadence; wherein the controlling comprises:
   controlling a time length of a frame with the determined gait cadence.

285. The non-transitory processor-readable medium of claim 284, wherein the time length of the frame is controlled by leveraging: the determined cadence, and a total number of frames contained in a gait cycle of the user's representation.

286. The non-transitory processor-readable medium of claim 285, the functions further comprising:
   determining a footstep of the user in real time as the footstep occurs; and
   using said footstep to synchronize a head movement of the user's representation with said footstep; wherein the head movement comprises a cyclical rotation.

287. A non-transitory processor-readable medium including instructions which, when executed by one or more processors, cause the one or more processors to perform functions comprising:
   determining a gait cadence of a user of a mobile or wearable device in real time as the gait cadence occurs; wherein the mobile or wearable device is carried by the user; and
   controlling, in real time as the gait cadence occurs, a user's representation in the mobile or wearable device with the determined gait cadence; wherein the user's representation is composed of at least three movable parts; wherein the controlling comprises: controlling one or more attributes of three or more of said movable parts of the user's representation with the determined gait cadence.

288. The non-transitory processor-readable medium of claim 287, the functions further comprising:
   determining a footstep of the user in real time as the footstep occurs; and
   using said footstep to synchronize a head movement of the user's representation with said footstep; wherein the head movement comprises a cyclical rotation.

289. The non-transitory processor-readable medium of claim 287, the functions further comprising: controlling, in real time as the gait cadence of the user occurs, a gait cadence of the user's representation with the determined gait cadence of the user.

290. A non-transitory processor-readable medium including instructions which, when executed by one or more processors, cause the one or more processors to perform functions comprising:
   determining a gait attribute of a user of a mobile or wearable device in real time as the gait attribute occurs; wherein the mobile or wearable device is carried by the user;

controlling, in real time as the gait attribute occurs, a user's representation in the mobile or wearable device with the determined gait attribute;

determining a length of a gait step of the user in real time as the gait step of the user occurs; and controlling an aspect of an application in the mobile or wearable device with the determined length of the gait step of the user, wherein the aspect of the application is different from the user's representation.

291. The non-transitory processor-readable medium of claim 290, wherein the aspect comprises elements different from the user's representation; wherein the user's representation may step on said elements.

292. A non-transitory processor-readable medium including instructions which, when executed by one or more processors, cause the one or more processors to perform functions comprising:

determining a gait related information of a user of a mobile or wearable device in real time as the gait related information occurs; wherein the mobile or wearable device is carried by the user;

controlling, in real time as the gait related information occurs, a user's representation in the mobile or wearable device with the determined gait related information; wherein the user's representation is composed of at least three movable parts;

determining a footstep of the user in real time as the footstep of the user occurs; and controlling, in real time as the footstep of the user occurs, an element different from the user's representation by using said footstep of the user; wherein the user's representation steps on said element.

293. The non-transitory processor-readable medium of claim 292, the functions further comprising:

using said footstep of the user to synchronize a head movement of the user's representation with said footstep of the user; wherein the head movement comprises a cyclical rotation.

294. The non-transitory processor-readable medium of claim 293, wherein the gait related information is selected from a set consisting of: a gait velocity of the user, a gait activity of the user, a gait cadence of the user, and a length of a gait step of the user;

wherein the gait activity of the user is selected from a set consisting of: a walking activity, a jogging activity, and a running activity.

295. A non-transitory processor-readable medium including instructions which, when executed by one or more processors, cause the one or more processors to perform functions comprising:

determining a gait related information of a user of a mobile or wearable device in real time as the gait related information occurs; wherein the mobile or wearable device is carried by the user; wherein a user's representation in the mobile or wearable device is composed of at least three movable parts; and controlling, in real time as the gait related information occurs, independently one or more attributes of at least two of said movable parts with the determined gait related information.

296. The non-transitory processor-readable medium of claim 295, the functions further comprising:

determining a footstep of the user in real time as the footstep occurs; and using said footstep to synchronize a head movement of the user's representation with said footstep; wherein the head movement comprises a cyclical rotation.

297. The non-transitory processor-readable medium of claim 296, wherein the gait related information is selected from a set consisting of: a gait velocity of the user, a gait activity of the user, a gait cadence of the user, and a length of a gait step of the user;

wherein the gait activity of the user is selected from a set consisting of: a walking activity, a jogging activity, and a running activity.

298. A non-transitory processor-readable medium including instructions which, when executed by one or more processors, cause the one or more processors to perform functions comprising:

determining a gait related information of a user of a mobile or wearable device in real time as the gait related information of the user occurs; wherein the mobile or wearable device is carried by the user; wherein a user's representation in the mobile or wearable device is composed of at least three movable parts;

controlling, in real time as the gait related information of the user occurs, the user's representation with the determined gait related information of the user;

determining a footstep of the user in real time as the footstep of the user occurs;

determining a time instant of the determined footstep of the user; and using the determined time instant to synchronize a stepping of the user's representation with the footstep of the user, by assigning a frame at which the user's representation is shown stepping to the determined time instant of the footstep of the user.

299. The non-transitory processor-readable medium of claim 298, the functions further comprising:

using said footstep of the user to: synchronize a head movement of the user's representation with said footstep of the user; wherein the head movement comprises a cyclical rotation.

300. The non-transitory processor-readable medium of claim 299, wherein the gait related information of the user is selected from a set consisting of: a gait velocity of the user, a gait activity of the user, a gait cadence of the user, and a length of a gait step of the user; wherein the gait activity of the user is selected from a set consisting of: a walking activity, a jogging activity, and a running activity.

301. The non-transitory processor-readable medium of claim 298, wherein the synchronizing the stepping of the user's representation with the footstep of the user comprises: determining a frame number of a frame which should be displayed, by using a determined time distance and a total number of frames contained in one gait cycle of the user's representation; wherein the frame which should be displayed comprises the frame at which the user's representation is shown stepping.

302. A non-transitory processor-readable medium including instructions which, when executed by one or more processors, cause the one or more processors to perform functions comprising:

determining a gait attribute of a user of a mobile or wearable device in real time as the gait attribute of the user occurs; wherein the mobile or wearable device is carried by the user;

wherein a user's representation in the mobile or wearable device is composed of at least three movable parts; and controlling, in real time as the gait attribute of the user occurs, the user's representation with the determined gait attribute of the user; wherein the controlling comprises: selecting a file which contains at least three images by using the determined gait attribute.

303. The non-transitory processor-readable medium of claim 302, wherein each one of said images shows a different posture of the user's representation.

304. A non-transitory processor-readable medium including instructions which, when executed by one or more processors, cause the one or more processors to perform functions comprising:
determining a gait attribute of a user of a mobile or wearable device in real time as the gait attribute of the user occurs; wherein the mobile or wearable device is carried by the user;
wherein a user's representation in the mobile or wearable device is composed of at least three movable parts;
controlling, in real time as the gait attribute of the user occurs, the user's representation with the determined gait attribute of the user; and
controlling a scaling of a representation with the determined gait attribute of the user, wherein the representation is different from the user's representation.

305. The non-transitory processor-readable medium of claim 304, the functions further comprising:
determining a footstep of the user in real time as the footstep occurs; and
using said footstep to synchronize a head movement of the user's representation with said footstep; wherein the head movement comprises a cyclical rotation.

306. The non-transitory processor-readable medium of claim 305, wherein the gait attribute is selected from a set consisting of: a gait velocity of the user, a gait activity of the user, a gait cadence of the user, and a length of a gait step of the user; wherein the gait activity of the user is selected from a set consisting of: a walking activity, a jogging activity, and a running activity.

307. The non-transitory processor-readable medium of claim 304, wherein the gait attribute of the user is determined with an update frequency greater than a step frequency of the user and less than a sampling rate of an accelerometer of the mobile or wearable device.

308. A non-transitory processor-readable medium including instructions which, when executed by one or more processors, cause the one or more processors to perform functions comprising:
determining a gait attribute of a user of a mobile or wearable device in real time as the gait attribute of the user occurs; wherein the mobile or wearable device is carried by the user;
wherein a user's representation in the mobile or wearable device is composed of at least three movable parts; and
controlling, in real time as the gait attribute of the user occurs, the user's representation with the determined gait attribute of the user; wherein the controlling comprises: controlling a scaling of the user's representation with the determined gait attribute of the user.

309. The non-transitory processor-readable medium of claim 308, the functions further comprising:
determining a footstep of the user in real time as the footstep occurs; and
using said footstep to synchronize a head movement of the user's representation with said footstep; wherein the head movement comprises a cyclical rotation.

310. The non-transitory processor-readable medium of claim 309, wherein the gait attribute is selected from a set consisting of: a gait velocity of the user, a gait activity of the user, a gait cadence of the user, and a length of a gait step of the user; wherein the gait activity of the user is selected from a set consisting of: a walking activity, a jogging activity, and a running activity.

311. The non-transitory processor-readable medium of claim 308, wherein the gait attribute of the user is determined with an update frequency greater than an upper edge of a frequency band of a gait activity of the user and less than a sampling rate of an accelerometer of the mobile or wearable device.

312. The non-transitory processor-readable medium of claim 308, wherein the gait attribute of the user is determined with an update frequency greater than a step frequency of the user and less than a sampling rate of an accelerometer of the mobile or wearable device.

313. The non-transitory processor-readable medium of claim 308, wherein the gait attribute is a velocity; the functions further comprising:
determining a gait cadence of the user in real time as the gait cadence of the user occurs; and
controlling, in real time as the gait cadence of the user occurs, one or more attributes of the user's representation by using the determined gait cadence of the user.

314. A non-transitory processor-readable medium including instructions which, when executed by one or more processors, cause the one or more processors to perform functions comprising:
determining a gait attribute of a user of a mobile or wearable device in real time as the gait attribute of the user occurs; wherein the mobile or wearable device is carried by the user;
wherein a user's representation in the mobile or wearable device is composed of at least three movable parts; and
controlling, in real time as the gait attribute of the user occurs, the user's representation with the determined gait attribute of the user; wherein a number of frames spanning a gait cycle of the user's representation is less than forty and greater than three.

315. The non-transitory processor-readable medium of claim 314, the functions further comprising:
determining a footstep of the user in real time as the footstep occurs; and
using said footstep to synchronize a head movement of the user's representation with said footstep; wherein the head movement comprises a cyclical rotation.

316. The non-transitory processor-readable medium of claim 315, wherein the gait attribute is selected from a set consisting of: a gait velocity of the user, a gait activity of the user, a gait cadence of the user, and a length of a gait step of the user; wherein the gait activity of the user is selected from a set consisting of: a walking activity, a jogging activity, and a running activity.

317. The non-transitory processor-readable medium of claim 314, wherein the gait attribute of the user is determined with an update frequency greater than a step frequency of the user and less than a sampling rate of an accelerometer of the mobile or wearable device.

318. A non-transitory processor-readable medium including instructions which, when executed by one or more processors, cause the one or more processors to perform functions comprising:
determining a gait related information of a user of a mobile or wearable device in real time as the gait related information of the user occurs; wherein the mobile or wearable device is carried by the user; wherein a user's representation in the mobile or wearable device is composed of at least three movable parts; and
controlling an attribute of the user's representation with the determined gait related information; wherein the attribute varies, in real time as the gait related information occurs, with the determined gait related information by following a mathematical relationship which uses a multiplication.

319. The non-transitory processor-readable medium of claim 318, the functions further comprising:
  determining a footstep of the user in real time as the footstep occurs; and
  using said footstep to synchronize a head movement of the user's representation with said footstep; wherein the head movement comprises a cyclical rotation.

320. The non-transitory processor-readable medium of claim 318, wherein the gait related information is selected from a set consisting of: a gait velocity of the user, a gait activity of the user, a gait cadence of the user, and a length of a gait step of the user;
  wherein the gait activity of the user is selected from a set consisting of: a walking activity, a jogging activity, and a running activity.

321. The non-transitory processor-readable medium of claim 318, wherein the gait related information is determined with an update frequency greater than an upper edge of a frequency band of a gait activity of the user and less than a sampling rate of an accelerometer of the mobile or wearable device.

322. The non-transitory processor-readable medium of claim 318, wherein the gait related information is determined with an update frequency greater than a step frequency of the user and less than a sampling rate of an accelerometer of the mobile or wearable device.

323. A non-transitory processor-readable medium including instructions which, when executed by one or more processors, cause the one or more processors to perform functions comprising:
  determining a gait related information of a user of a mobile or wearable device in real time as the gait related information of the user occurs; wherein the mobile or wearable device is carried by the user; wherein a user's representation in the mobile or wearable device is composed of at least three movable parts; wherein the determining comprises leveraging an accelerometer; wherein the gait related information is determined with an update frequency greater than an upper edge of a frequency band of a gait activity of the user and less than a sampling rate of the accelerometer; and
  controlling, in real time as the gait related information occurs, the user's representation with the determined gait related information.

324. The non-transitory processor-readable medium of claim 323, the functions further comprising:
  determining a footstep of the user in real time as the footstep occurs; and
  using said footstep to synchronize a head movement of the user's representation with said footstep; wherein the head movement comprises a cyclical rotation.

325. The non-transitory processor-readable medium of claim 323, wherein the upper edge is 3 Hz.

326. The non-transitory processor-readable medium of claim 323, wherein the upper edge is 8 Hz.

327. The non-transitory processor-readable medium of claim 323, wherein the gait related information is selected from a set consisting of: a gait velocity of the user, the gait activity of the user, a gait cadence of the user, and a length of a gait step of the user;
  wherein the gait activity of the user is selected from a set consisting of: a walking activity, a jogging activity, and a running activity.

328. The non-transitory processor-readable medium of claim 323, wherein the controlling is performed with an update frequency lower than a refresh rate of a screen of the mobile or wearable device and greater than the upper edge of the frequency band of the gait activity of the user.

329. A non-transitory processor-readable medium including instructions which, when executed by one or more processors, cause the one or more processors to perform functions comprising:
  determining a gait related information of a user of a mobile or wearable device in real time as the gait related information of the user occurs; wherein the mobile or wearable device is carried by the user; wherein a user's representation in the mobile or wearable device is composed of at least three movable parts; wherein the determining comprises leveraging an accelerometer; and
  controlling, in real time as the gait related information occurs, the user's representation with the determined gait related information; wherein the controlling is performed with an update frequency less than a refresh rate of a screen of the mobile or wearable device and greater than an upper edge of a frequency band of a gait activity of the user.

330. The non-transitory processor-readable medium of claim 329, the functions further comprising:
  determining a footstep of the user in real time as the footstep occurs; and
  using said footstep to synchronize a head movement of the user's representation with said footstep; wherein the head movement comprises a cyclical rotation.

331. The non-transitory processor-readable medium of claim 329, wherein the upper edge is 3 Hz.

332. The non-transitory processor-readable medium of claim 329, wherein the upper edge is 8 Hz.

333. The non-transitory processor-readable medium of claim 329, wherein said update frequency is constant and less than a sampling rate of the accelerometer.

334. The non-transitory processor-readable medium of claim 329, wherein said update frequency is constant and less than a sampling rate of the accelerometer; and
  wherein said sampling rate is variable.

335. The non-transitory processor-readable medium of claim 329, wherein the gait related information is selected from a set consisting of: a gait velocity of the user, the gait activity of the user, a gait cadence of the user, and a length of a gait step of the user;
  wherein the gait activity of the user is selected from a set consisting of: a walking activity, a jogging activity, and a running activity.

336. A non-transitory processor-readable medium including instructions which, when executed by one or more processors, cause the one or more processors to perform functions comprising:
  determining a gait related information of a user of a mobile or wearable device in real time as the gait related information of the user occurs; wherein the mobile or wearable device is carried by the user; wherein a user's representation in the mobile or wearable device is composed of at least three movable parts;
  controlling, in real time as the gait related information occurs, the user's representation with the determined gait related information;
  determining a footstep of the user in real time as the footstep occurs; and
  using said footstep to synchronize a movement of at least one movable part of said at least three movable parts of the user's representation with the determined footstep; wherein the at least one movable part is above a hip of the user's representation.

337. The non-transitory processor-readable medium of claim 336, wherein the at least one movable part comprises a head of the user's representation.

338. The non-transitory processor-readable medium of claim 337, wherein the gait related information is selected from a set consisting of: a gait velocity of the user, a gait activity of the user, a gait cadence of the user, and a length of a gait step of the user; wherein the gait activity of the user is selected from a set consisting of: a walking activity, a jogging activity, and a running activity.

339. The non-transitory processor-readable medium of claim 337, wherein the movement of the at least one movable part comprises a cyclical rotation.

340. The non-transitory processor-readable medium of claim 339, wherein the gait related information is selected from a set consisting of: a gait velocity of the user, a gait activity of the user, a gait cadence of the user, and a length of a gait step of the user; wherein the gait activity of the user is selected from a set consisting of: a walking activity, a jogging activity, and a running activity.

341. The non-transitory processor-readable medium of claim 337, wherein the movement of the at least one movable part comprises two different cyclical rotations.

342. The non-transitory processor-readable medium of claim 337, the functions further comprising:
determining a time instant of the determined footstep; and
using the determined time instant to synchronize the movement of the at least one movable part with said footstep by: assigning a frame at which the user's representation's head is shown rotated with a maximum rotation angle of a cyclical rotation, to the determined time instant of the footstep of the user.

343. The non-transitory processor-readable medium of claim 342, wherein the gait related information is selected from a set consisting of: a gait velocity of the user, a gait activity of the user, a gait cadence of the user, and a length of a gait step of the user; wherein the gait activity of the user is selected from a set consisting of: a walking activity, a jogging activity, and a running activity.

344. The non-transitory processor-readable medium of claim 336, wherein the at least one movable part comprises a hair of the user's representation.

345. The non-transitory processor-readable medium of claim 344, wherein a root of the hair is assigned a weight different from a weight assigned to a tip of the hair.

346. The non-transitory processor-readable medium of claim 336, wherein the movement of the at least one movable part comprises a facial expression of the user's representation.

347. The non-transitory processor-readable medium of claim 336, wherein the at least one movable part comprises a movable part of a face of the user's representation.

348. The non-transitory processor-readable medium of claim 347, wherein the gait related information is selected from a set consisting of: a gait velocity of the user, a gait activity of the user, a gait cadence of the user, and a length of a gait step of the user; wherein the gait activity of the user is selected from a set consisting of: a walking activity, a jogging activity, and a running activity.

349. The non-transitory processor-readable medium of claim 336, wherein the at least one movable part comprises an eye of the user's representation.

350. The non-transitory processor-readable medium of claim 336, wherein the at least one movable part comprises an eyebrow of the user's representation.

351. A non-transitory processor-readable medium including instructions which, when executed by one or more processors, cause the one or more processors to perform functions comprising:
determining a gait related information of a user of a mobile or wearable device in real time as the gait related information of the user occurs; wherein the mobile or wearable device is carried by the user; wherein a user's representation in the mobile or wearable device is composed of at least three movable parts;
controlling, in real time as the gait related information occurs, the user's representation with the determined gait related information;
determining a footstep of the user in real time as the footstep occurs; and
using said footstep to synchronize a rotation of at least one movable part of an upper body of the user's representation with the determined footstep; wherein the at least one movable part of the upper body of the user's representation is from the at least three movable parts of the user's representation.

352. The non-transitory processor-readable medium of claim 351, wherein the gait related information is selected from a set consisting of: a gait velocity of the user, a gait activity of the user, a gait cadence of the user, and a length of a gait step of the user;
wherein the gait activity of the user is selected from a set consisting of: a walking activity, a jogging activity, and a running activity.

353. A non-transitory processor-readable medium including instructions which, when executed by one or more processors, cause the one or more processors to perform functions comprising:
determining a gait related information of a user of a mobile or wearable device in real time as the gait related information of the user occurs; wherein the mobile or wearable device is carried by the user; wherein a user's representation in the mobile or wearable device is composed of at least three movable parts;
controlling, in real time as the gait related information occurs, the user's representation with the determined gait related information;
determining a footstep of the user in real time as the footstep occurs; and
using said footstep to synchronize a cyclical up and down movement of an upper body of the user's representation with the determined footstep.

354. The non-transitory processor-readable medium of claim 353, wherein the gait related information is selected from a set consisting of: a gait velocity of the user, a gait activity of the user, a gait cadence of the user, and a length of a gait step of the user;
wherein the gait activity of the user is selected from a set consisting of: a walking activity, a jogging activity, and a running activity.

* * * * *